United States Patent
Irudayaraj et al.

(10) Patent No.: US 11,821,892 B2
(45) Date of Patent: Nov. 21, 2023

(54) NANOBUBBLES

(71) Applicant: Purdue Research Foundation, West Lafayette, IN (US)

(72) Inventors: Joseph Irudayaraj, Champaign, IL (US); Pushpak Bhandari, Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 448 days.

(21) Appl. No.: 16/851,130

(22) Filed: Apr. 17, 2020

(65) Prior Publication Data

US 2020/0249221 A1 Aug. 6, 2020

Related U.S. Application Data

(60) Division of application No. 15/914,293, filed on Mar. 7, 2018, now Pat. No. 10,670,581, which is a continuation-in-part of application No. 14/873,208, filed on Oct. 2, 2015, now Pat. No. 9,968,692.

(60) Provisional application No. 62/147,267, filed on Apr. 14, 2015, provisional application No. 62/075,496, filed on Nov. 5, 2014, provisional application No. 62/058,793, filed on Oct. 2, 2014.

(51) Int. Cl.

| | |
|---|---|
| *G01N 33/50* | (2006.01) |
| *A61K 49/22* | (2006.01) |
| *A61K 47/69* | (2017.01) |
| *A61K 47/61* | (2017.01) |
| *A61K 31/407* | (2006.01) |
| *A61K 41/00* | (2020.01) |
| *A61K 9/50* | (2006.01) |
| *A61K 47/54* | (2017.01) |
| *A61M 37/00* | (2006.01) |
| *G01N 21/31* | (2006.01) |
| *A61P 35/00* | (2006.01) |
| *G01N 21/64* | (2006.01) |

(52) U.S. Cl.
CPC ....... *G01N 33/5008* (2013.01); *A61K 9/5047* (2013.01); *A61K 31/407* (2013.01); *A61K 41/00* (2013.01); *A61K 41/0028* (2013.01); *A61K 47/54* (2017.08); *A61K 47/61* (2017.08); *A61K 47/6925* (2017.08); *A61K 49/223* (2013.01); *A61M 37/0092* (2013.01); *A61P 35/00* (2018.01); *G01N 21/31* (2013.01); *A61M 2210/1085* (2013.01); *G01N 21/6428* (2013.01); *G01N 21/6456* (2013.01); *G01N 2021/6439* (2013.01)

(58) Field of Classification Search
None
See application file for complete search history.

(56) References Cited

U.S. PATENT DOCUMENTS

| | | | |
|---|---|---|---|
| 7,338,451 | B2 | 3/2008 | Tsuzuki |
| 2007/0059248 | A1 | 3/2007 | Unger et al. |
| 2012/0034170 | A1 | 2/2012 | Ottoboni et al. |
| 2013/0041311 | A1 | 2/2013 | Kohane et al. |
| 2016/0166716 | A1* | 6/2016 | Irudayaraj .......... A61K 41/0028 424/499 |

OTHER PUBLICATIONS

Chang, L., et al., "Pharmacokinetics of quercetin-loaded nanodroplets with ultrasound activation and their use for bioimaging", Int. J. Nanomedicine, pp. 3031-3042 (Year: 2015).*
Porten, S. P., et al., "Intravesical chemotherapy in non-muscle-invasive bladder cancer", Indian J. Urology, pp. 297-303 (Year: 2015).*
Iannuccelli, V. et al., "Effect of the loading method on the drug release from cross-linked carboxymethylcellulose beads," J. Contr. Release, 1993, pp. 13-20.
Wu, H. et al., "Acoustic Characterization and Pharamacokinetic Analyses of New Nanobubble Ulrasound Contrast Agents," Ultrasound. Med. Biol., 2013, pp. 2137-2146.
Sharpiro, M. G., et al., Biogenic gas nanostructures as ultrasonic molecular reporters. Nature Nanotechnology, 2014, 9, 311-316.
Goldberg, A.D., et al., Epigenetics: A Landscape Takes Shape. Cell, 2007, 128, 635-638.
Chen, J., et al., Fluorescence Lifetime Cross Correlation Spectroscopy Resolves EGFR and Antagonist Interaction in ivLe Cells. Anal. Chem. 2010, 82, 6415-6421.
Gonzalo, S., Epigenetic alterations in aging. J. Appl. Physiol. 109: 586-597, 2010.
Formenti, F., et al., Regulation of human metabolism by hypoxiainducible factor. Proc. Natl. Acad. Sci. USA, 2010, 107, 12722-12727.
Maxwell, P.H., et al., The tumour suppressor proteinVHL targets hypoxia-inducible factors for oxygen-dependent proteolysis. Nature, 1999, 399, 271-275.
Wang, G.L., et al., Hypoxia-Inducible Factor 1 is a Basic-Helix-Loop-Helix-PAS Heterodimer Regulated by O2 Tension. Proc. Natl. Acad. Sci. USA, 1995, 92, 5510-5514.
Ema, M. et al., A novel bHLH-PAS factor with close sequence similarity to hypoxia-inducible factor 1a regulates the VEGF expression and is potentially involved in lung and vascular development. Proc. Natl. Acad. Sci. USA, vol. 94, pp. 4273-4278, Apr. 1997.
Tsakalozou, E., et al., Combination Effects of Docetaxel and Doxorubicin in Hormone-Refractory Prostate Cancer Cells. Biochemistry Research International, vol. 2012, Article ID 832059, 10 pages, doi: 10.1155/2012/832059.
Chen, J., et al., Quantitative Investigation of Compartmentalized Dynamics of ErbB2 Targeting Gold Nanorods in Live Cells by Single Molecule Spectroscopy. ACS Nano 2009, vol. 3, 4071-4079.

(Continued)

Primary Examiner — Michael G. Hartley
Assistant Examiner — Lance W Rider
(74) Attorney, Agent, or Firm — Purdue Research Foundation

(57) ABSTRACT

The present invention provides oxygenized nanobubbles and their uses in imaging and cancer treatment when combined with therapeutic drugs and precise ultrasound beam steering.

6 Claims, 35 Drawing Sheets

(56) References Cited

OTHER PUBLICATIONS

Mackler, N.J., et al., Drug Insight: use of docetaxel in prostate and urothelial cancers. Nature Clinical Practice Urology, 2005, vol. 2, 92-100.

Zhang, X.H., et al., Nanobubbles at the Interface between Water and a Hydrophobic Solid. Langmuir 2008, 24, 4756-4764.

Habich, A., et al., Do Stable Nanobubbles Exist in Mixtures of Organic Solvents and Water? J. Phys. Chem. B 2010, 114, 6962-6967.

Zhao, Y., et al., Potential and problems in ultrasound-responsive drug delivery systems. International Journal of Nanomedicine, 2013:8 1621-1633.

Horie, S. et al., Development of Localized Gene Delivery Using a Dual-Intensity Ultrasound System in the Bladder. Ultrasound in Med. & Biol., vol. 36, No. 11, pp. 1867-1875, 2010.

Fan, X., et al., Experimental investigation of the penetration of ultrasound nanobubbles in a gastric cancer xenograft. Nanotechnology 24 (2013) 325102 (10pp) doi:10.1088/0957-4484/24/32/325102.

Yin, T., et al., Tumor-penetrating codelivery of siRNA and paclitaxel with ultrasound-responsive nanobubbles hetero-assembled from polymeric micelles and liposomes. Biomaterials 35 (2014) 5932-5943.

Huang, H., et al., A Multitheragnostic Nanobubble System to Induce Blood-Brain Barrier Disruption with Magnetically Guided Focused Ultrasound. Adv. Mater. 2015, 27, 655-661.

Rapoport, N.Y., et al., Controlled and targeted tumor chemotherapy by ultrasound-activated nanoemulsions/microbubbles. Journal of Controlled Release 138 (2009) 268-276.

Mohan, P., et al., Doxorubicin as a Molecular Nanotheranostic Agent: Effect of Doxorubicin Encapsulation in Micelles or Nanoemulsions on the Ultrasound-Mediated Intracellular Delivery and Nuclear Trafficking. Molecular Pharmaceutics, 2010, vol. 7, 1959-1973.

Wang, C., et al., Gold Nanorod/Fe3O4 Nanoparticle "Nano-Pearl-Necklaces" for Simultaneous Targeting, Dual-Mode Imaging, and Photothermal Ablation of Cancer Cells. Angew. Chem. Int. Ed. 2009, 48, 2759-2763.

Teicher, B.A. et al., "RSR13: Effecs on Tumor Oxygenation and Response to Therapy", Drug Dev. Res., pp. 1-11 (Year: 1996).

Dai, Y. et al., "Impact of Hypoxia on the Metastatic Potential of Human Prostate Cancer Cells", Int. J. Rad. Onc. Biol. Phys., pp. 521-528 (Year: 2011).

Mortimer, M. et al., "Potential of Hyperspectral Imaging Microscopy for Semi-quantitative Analysis of Nanoparticle Uptake by Protozoa", Envir. Sci. Tech., pp. 8760-8767 and S1-S16 (Year: 2014).

Cavalli, R. et al., "Preparation and characterization of dextran nanobubbles for oxygen delivery", Int. J. Pharm., pp. 160-165 (Year: 2009).

* cited by examiner

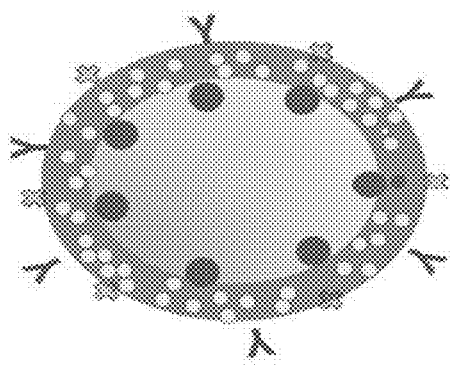
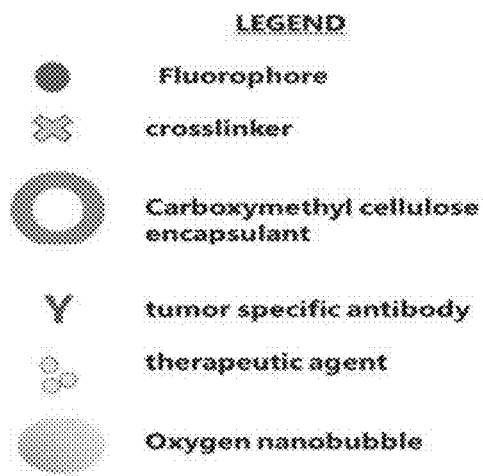
FIG. 1

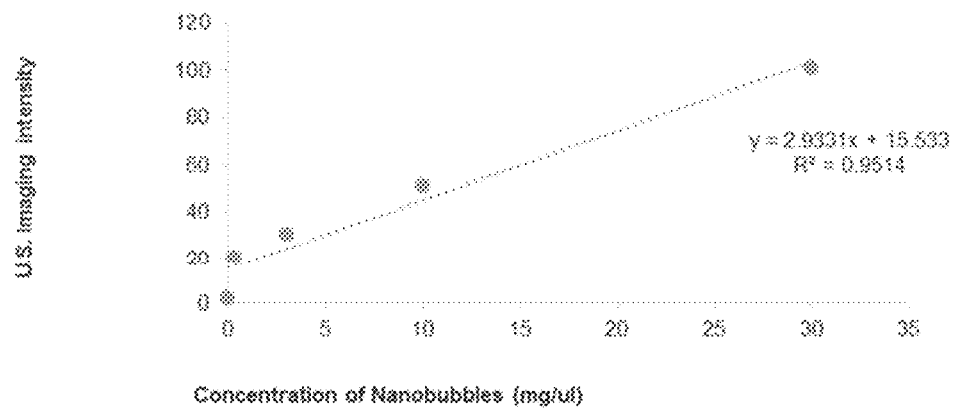
FIG. 8
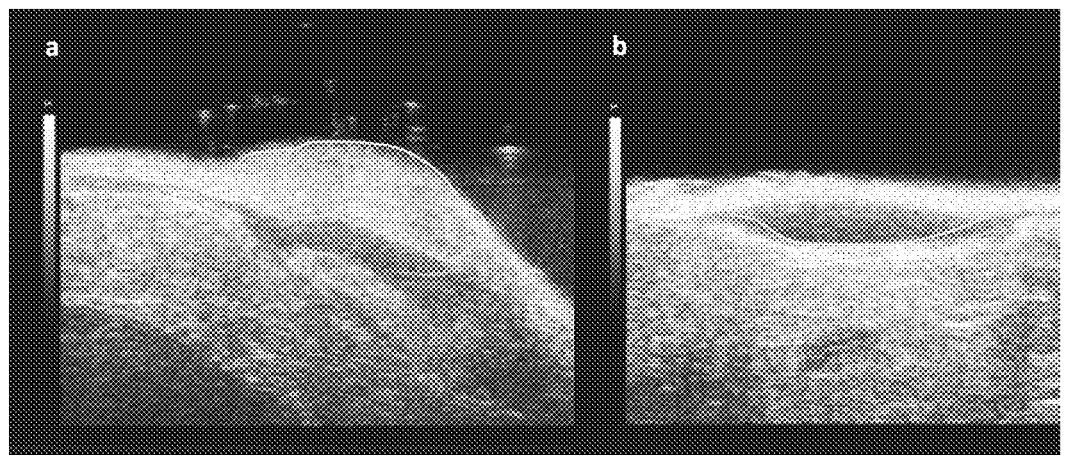
FIGS. 9A-9B
FIG. 9

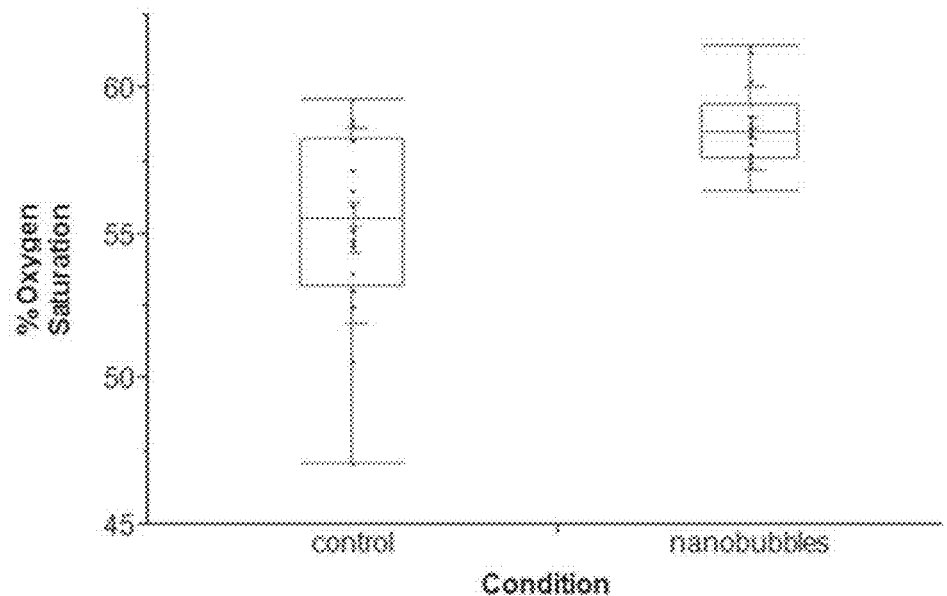
FIG. 20
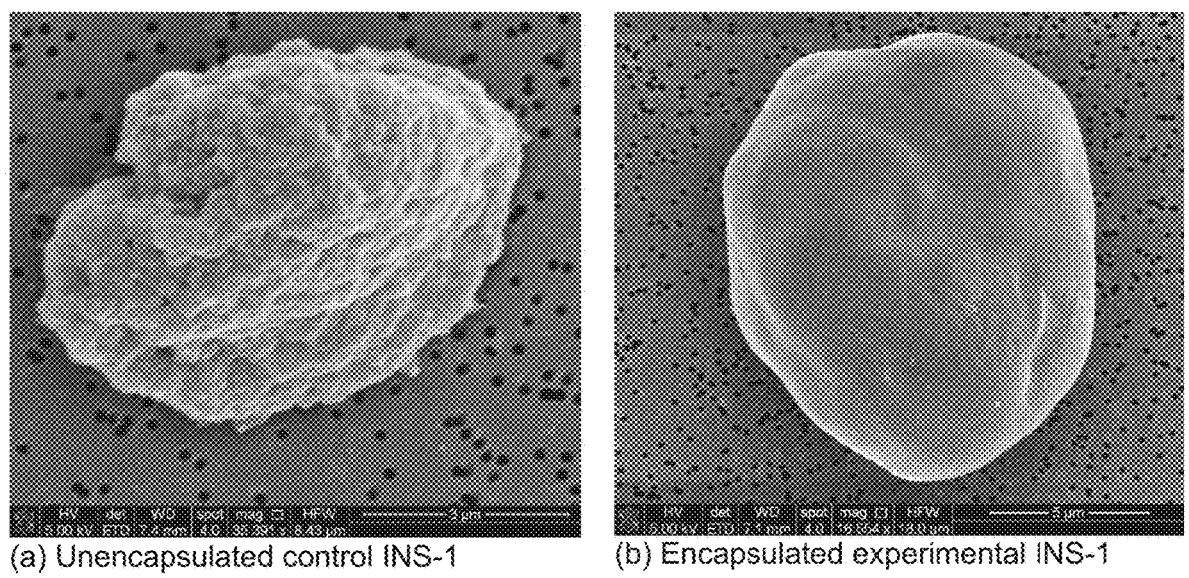
(a) Unencapsulated control INS-1   (b) Encapsulated experimental INS-1
FIGS. 21A-21B
FIG. 21

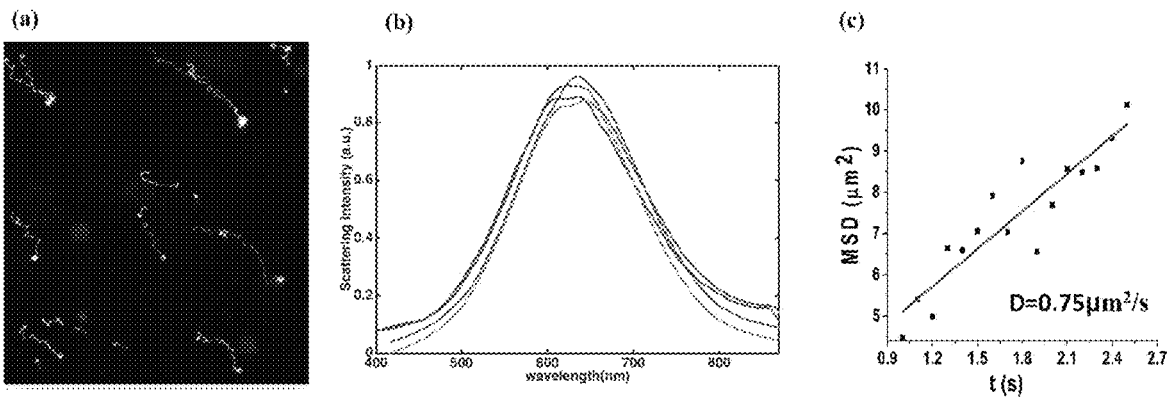
FIGS. 27A, 27B, 27C
FIG. 27
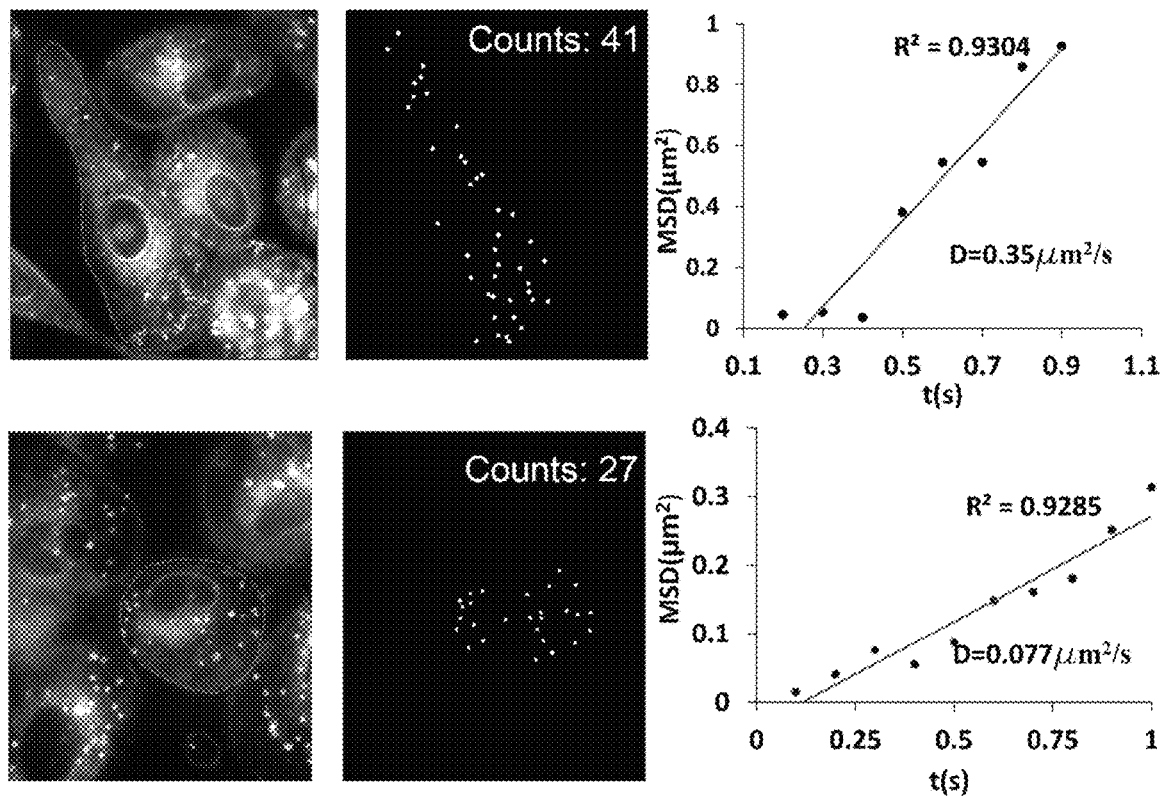
FIG. 28A  FIG. 28B  FIG. 28C
FIG. 28

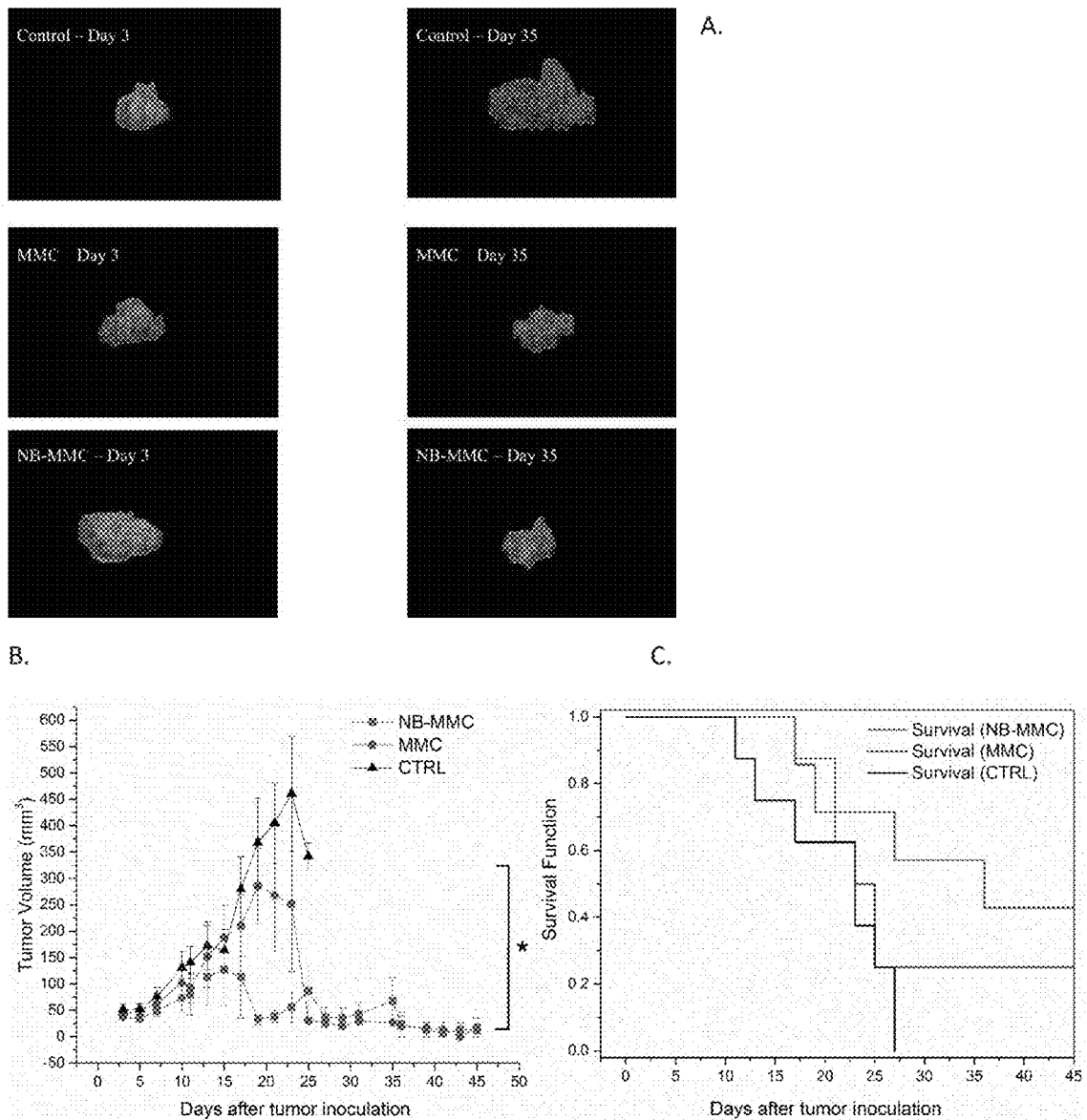
FIG. 43 A-C

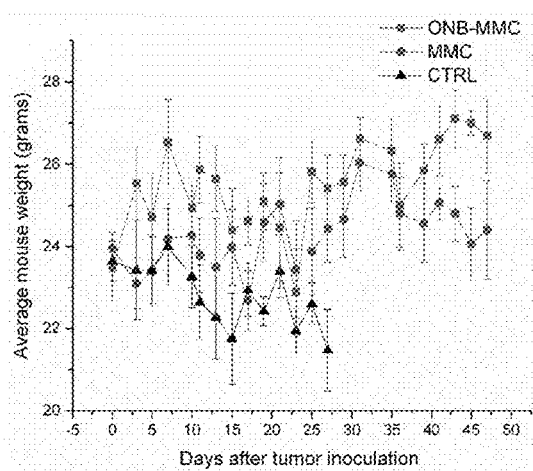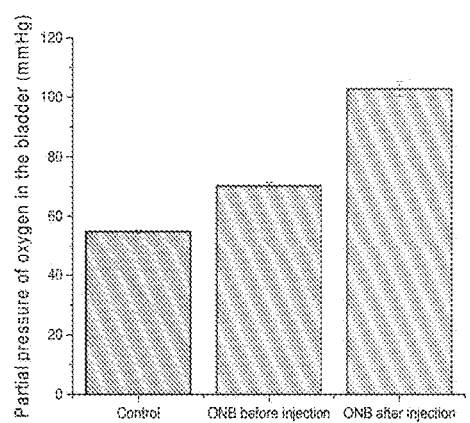
FIG. 43 D-E

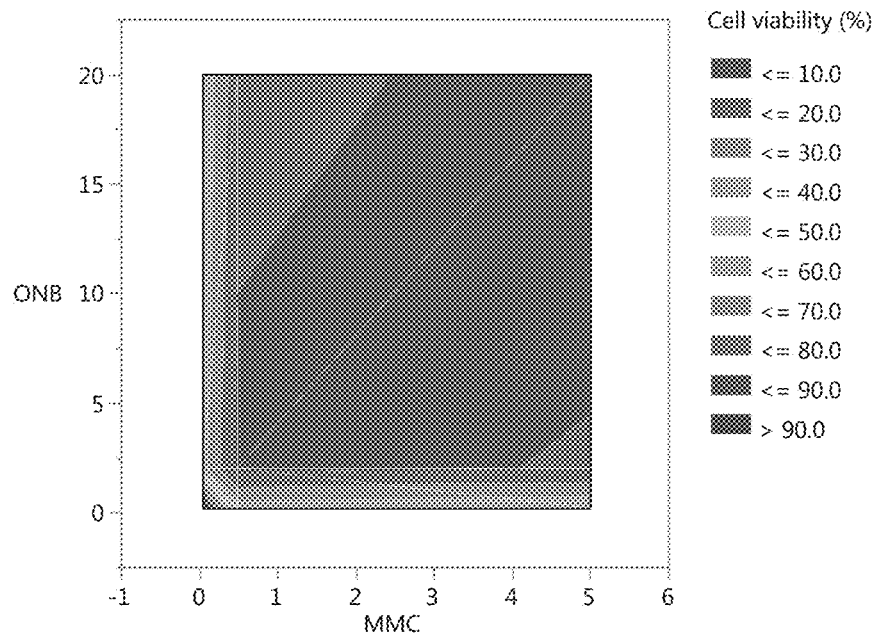
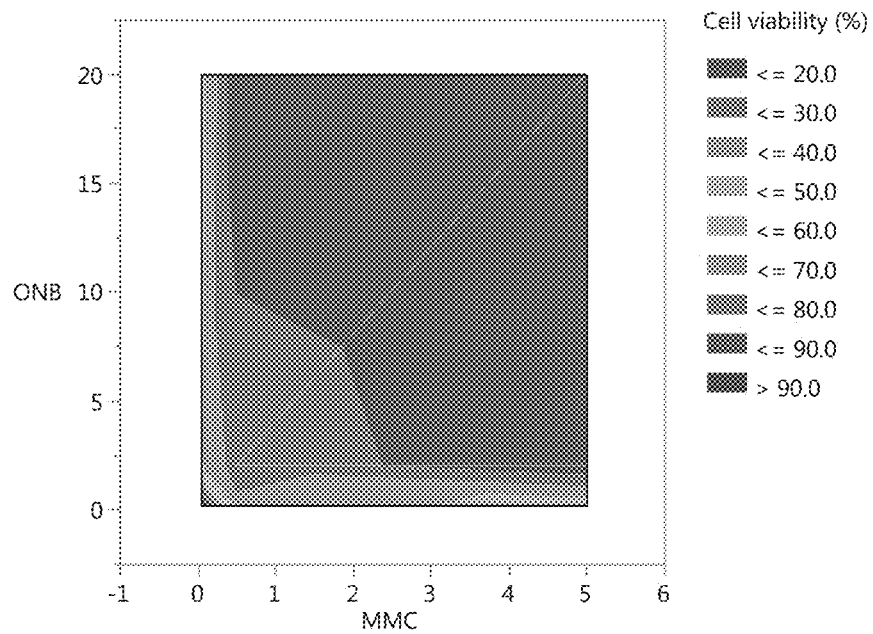
FIG. 47

NANOBUBBLES

CROSS REFERENCE

This application is a Divisional of U.S. application Ser. No. 15/914,293, filed Mar. 7, 2018, now U.S. Pat. No. 10,670,581, which is a Continuation-in-Part of U.S. application Ser. No. 14/873,208, filed on Oct. 2, 2015, now U.S. Pat. No. 9,968,692, which claims the priority of U.S. provisional application No. 62/147,267, filed on Apr. 14, 2015, U.S. provisional application No. 62/075,496, filed on Nov. 5, 2014 and U.S. provisional application No. 62/058,793, filed on Oct. 2, 2014. The contents of which are hereby expressly incorporated herein by reference in their entireties.

GOVERNMENT RIGHTS

This invention was made with government support under CA023168 awarded by the National Institutes of Health. The government has certain rights in the invention.

FIELD OF INVENTION

This disclosure generally relates to the make and use of oxygen nanobubble (ONB) in a single cell/tissue. Particularly, precise localization and tracking of single ONBs is provided based on hyperspectral dark-field microscope (HSDFM).

BACKGROUND

This section introduces aspects that may help facilitate a better understanding of the disclosure. Accordingly, these statements are to be read in this light and are not to be understood as admissions about what is or is not prior art.

Ultrasound is a valuable diagnostic imaging technique for studying various areas of the body, including, for example, the vasculature, such as tissue microvasculature. Ultrasound provides certain advantages over other diagnostic techniques. For example, diagnostic techniques involving nuclear medicine and X-rays generally involve exposure of the patient to ionizing electron radiation. Such radiation can cause damage to subcellular material, including deoxyribonucleic acid (DNA), ribonucleic acid (RNA) and proteins. Ultrasound does not involve such potentially damaging radiation. In addition, ultrasound is relatively inexpensive relative to other diagnostic techniques, including CT and MRI, which require elaborate and expensive equipment.

Ultrasound involves the exposure of a patient to sound waves. Generally, the sound waves dissipate due to absorption by body tissue, penetrate through the tissue or reflect off of the tissue. The reflection of sound waves off of tissue, generally referred to as backscatter or reflectivity, forms the basis for developing an ultrasound image. In this connection, sound waves reflect differentially from different body tissues. This differential reflection is due to various factors, including the constituents and the density of the particular tissue being observed.

Ultrasound involves the detection of the differentially reflected waves, generally with a transducer that can detect sound waves having a frequency of one megahertz (MHZ) to ten MHZ. The detected waves can be integrated into an image which is quantitated and the quantitated waves converted into an image of the tissue being studied.

Ultrasound contrast agents are used to enhance the signal when imaging a patient using ultrasound. One interesting way to produce an ultrasound image is with a microbubble. Microbubbles are described as sphere or sphere-like ranging in size of greater than one micrometer, but smaller than one millimeter. Generally they are hollow with a gas core and vibrate when a sonic energy field is applied. The wave frequency emitted from the vibrating microbubble helps to produce an ultrasound image.

Another interesting use of a microbubble is to deliver a pharmaceutical agent to a tissue within the body. By encapsulating a pharmaceutical agent in a microbubble made up of a shell the pharmaceutical agent is delivered to a location prior to coming into contact with the cells and proteins which may alter its function, bioavailability, or concentration.

However, a drawback to the microbubbles and even nanobubbles currently known in the art is that they are too large and cumbersome for imaging or delivery of a therapeutic. What is needed is a smaller delivery mechanism that can travel into smaller vasculature and cross barriers between tissues and cells. More specifically it would be desirable to have a nanobubble that is small enough for imaging or delivery of a therapeutic. It would be further desirable if the nanobubble could be directed to the desired tissue and then have a therapeutic delivered at a specific time and place.

SUMMARY OF THE INVENTION

In one aspect of the present invention there is provided a nanobubble comprising a continuous outer shell, the outer shell comprising a cross-linked polymeric material, an inner wall of the continuous outer shell and a hollow core within the continuous outer shell. The nanobubble may be less than 250 nm in diameter. In a further aspect of the invention, the cross-linked polymeric material is a cellulose-based material.

In another aspect of the present invention, the outer shell may further comprise a fluorophore, a pharmaceutical, a biomolecule, a ligand, contrast imaging agents, antibodies, lipids, protein receptors, aptamers or combinations thereof. The hollow core may be filled with a solid, a liquid, a gas or combinations thereof.

In another aspect of the present invention, the exemplified oxygen nanobubble is applied in hyperspectral dark-field microscope and used as contrast-generating imaging agent to image dynamic events of nano-probes and biomolecules at the single cell level, within cellular microenvironment, cytoplasm, as well as the nucleus.

In another aspect of the present invention, exemplified oxygen nanobubbles are propelled and precisely guided in vivo to the tumor by an ultrasound beam. Such precise ultrasound beam steering of oxygen nanobubbles enhances the efficacy of mitomycin-C, resulting in significantly lower tumor progression rates while using a about 50% lower concentration of chemotherapeutic drug.

In another aspect of the present invention, an exemplified oxygen nanobubble drug encapsulation system reverses hypoxia through targeted oxygen delivery.

These and other features, aspects and advantages of the present invention will become better understood with reference to the following figures, associated descriptions and claims.

BRIEF DESCRIPTION OF THE FIGURES

FIG. 1 is an illustrative graphic of one embodiment of a nanobubble incorporating at least one antibody and a therapeutic agent within the outer shell, and a fluorophore and oxygen encapsulated in the hollow inner core of the nanobubble;

FIG. 8 is a graph illustrating the mean ultrasound (U.S.) imaging intensity increases upon increase in nanobubble concentration;

FIG. 9 shows two images the first on the left (FIG. 9A) shows unburst oxygen bubbles after they were injected subcutaneously under the dermis of a mouse, and the second picture on the right (FIG. 9B) shows a dark spot where saline was injected subcutaneously under the dermis of a mouse;

FIG. 20 is a graph depicting the increase in the oxygen levels in the cell culture media in case of the nanobubble treated sample is significant when compared against the control sample;

FIG. 21 is two electron microscopy images of an islet cell (INS-1) where on the left (FIG. 21A) the cell is unencapsulated and the cell on the right (FIG. 21B) is encapsulated by an outer shell consisting of carboxymethyl cellulose and oxygen but not limited to these materials;

FIG. 27 Illustration of single nanobubble (400 nm) tracking in vitro. (FIG. 27A) The trajectories of each ONBs are tracked by linking nanobubble positions in each time frame in the image stacks. (FIG. 27B) Normalized scattering spectras of 400 nm ONBs in PCR cells using HSDFI (n=4). (FIG. 27C) Mean square displacement versus time. The diffusion coefficient of 400 nm ONBs in PBS is calculated based on linear fitting of mean square displacement with mean square displacement equation.

FIG. 28 Precise quantification and tracking of ONBs with different diameters (400 nm (top) and 800 nm (bottom)). The left columns show the trajectories of each ONB in single PC3 cell (FIG. 28A). The middle column shows the quantification results of ONBs in cell after two hours of incubation with ONBs (FIG. 28B), while the right column shows the diffusion coefficient of single ONB based on fitting of the mean square displacement (FIG. 28C).

FIG. 30 Quantitative detection of 400 nm ONBs in subcutaneously implanted Mb49 bladder cancer tissue in mice.

TABLE 1

Full factorial design for synthesis of 400 nm and 800 nm nanobubbles.

| No. | Optimization variable | Value | Code | Optimized parameters |
|---|---|---|---|---|
| 1. | Crosslinker concentration | 0.1% | −1 | 0.1% for 400 nm |
|  |  | 0.5% | 0 | 0.8% for 800 nm |
|  |  | 1% | 1 |  |
| 2. | CMC concentration | 0.1% | −1 | 0.1% for 400 nm |
|  |  | 0.5% | 0 | 1% for 800 nm |
|  |  | 1% | 1 |  |
| 3. | Ultrasound Power | 20% | −1 | Not significant |
|  |  | 50% | 0 |  |
|  |  | 100% | 1 |  |

Figures 31A, 31B, 31C, 31D:
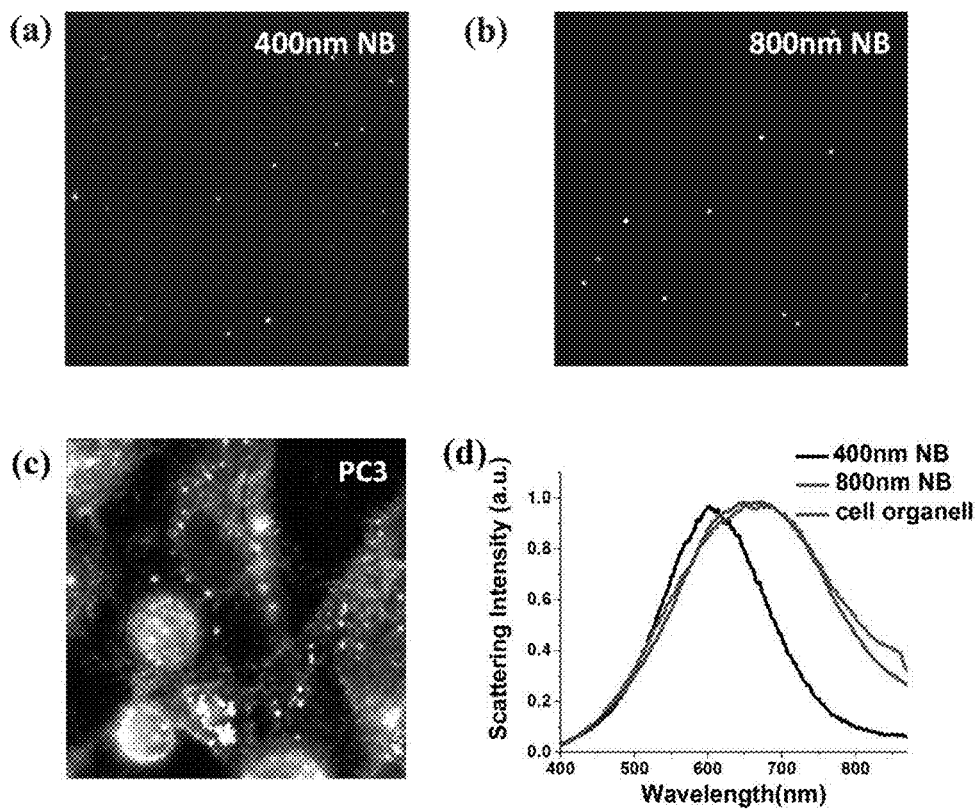

FIG. 31: Dark-field optical images of nanobubble with different size (FIGS. 31A-B) and PC3 cell without nanobubble (FIG. 31C). Spectra of nanobubbles and cell organelle in PC3 cell were extracted from hyperspectral data (FIG. 31D).

Figures 32A, 32B:
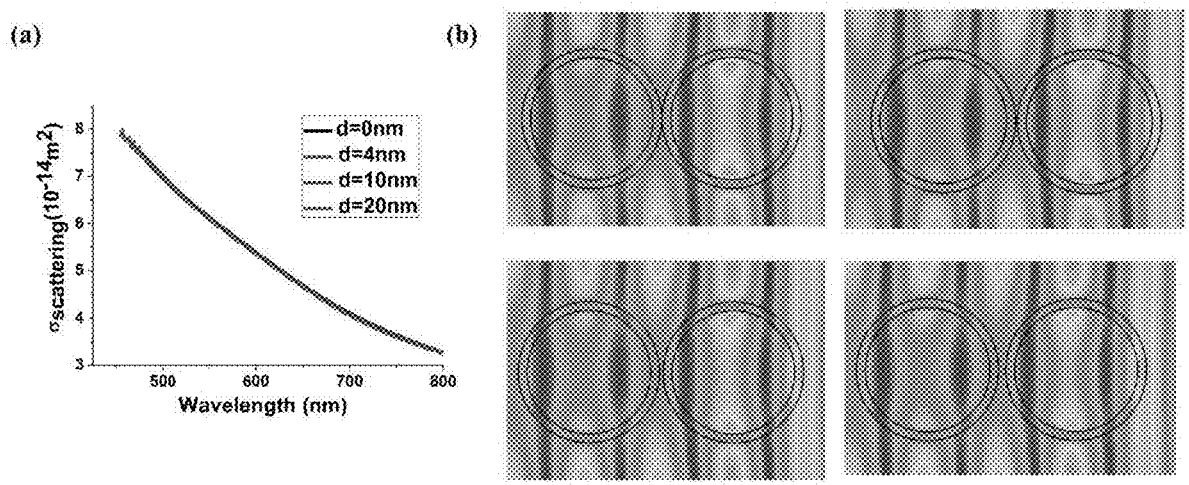

FIG. 32: The simulated far-field scattering with CST studio suite 2014 software. (FIG. 32A) Far-field scattering cross section of nanobubble dimer with different gap distance. (FIG. 32B) Electronic field intensity distribution with difference gap distance at 545 THz. A plane wave incident source with linear polarization in the range of 330 to 660 THz was used for calculation.

Figures 33A, 33B, 33C:
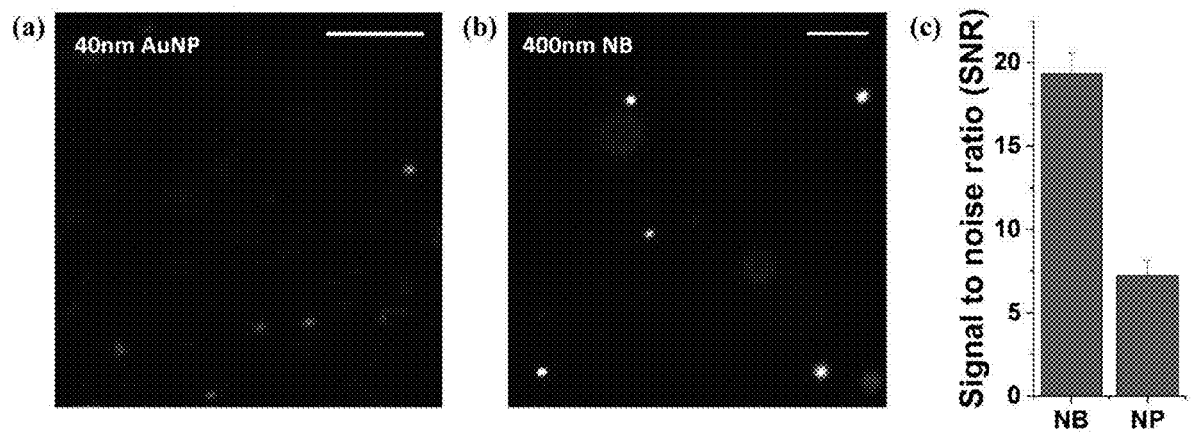

FIG. 33: Dark-field optical images of 40 nm AuNp (FIG. 33A) and 400 nm oxygen nanobubble (FIG. 33B) in vitro. ONBs have a significantly higher signal to noise (SNR) ratio compared to AuNp (FIG. 33C).

Figure 34:
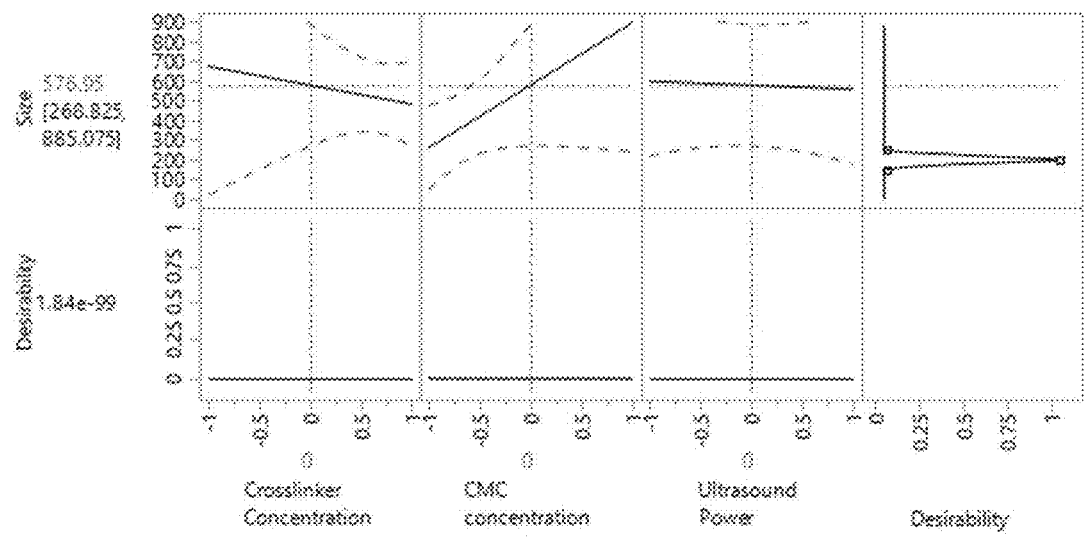

FIG. 34: Prediction profile for the optimization of nanobubble size. Crosslinker and CMC concentration were significant in influencing the size of nanobubbles.

Figure 35:
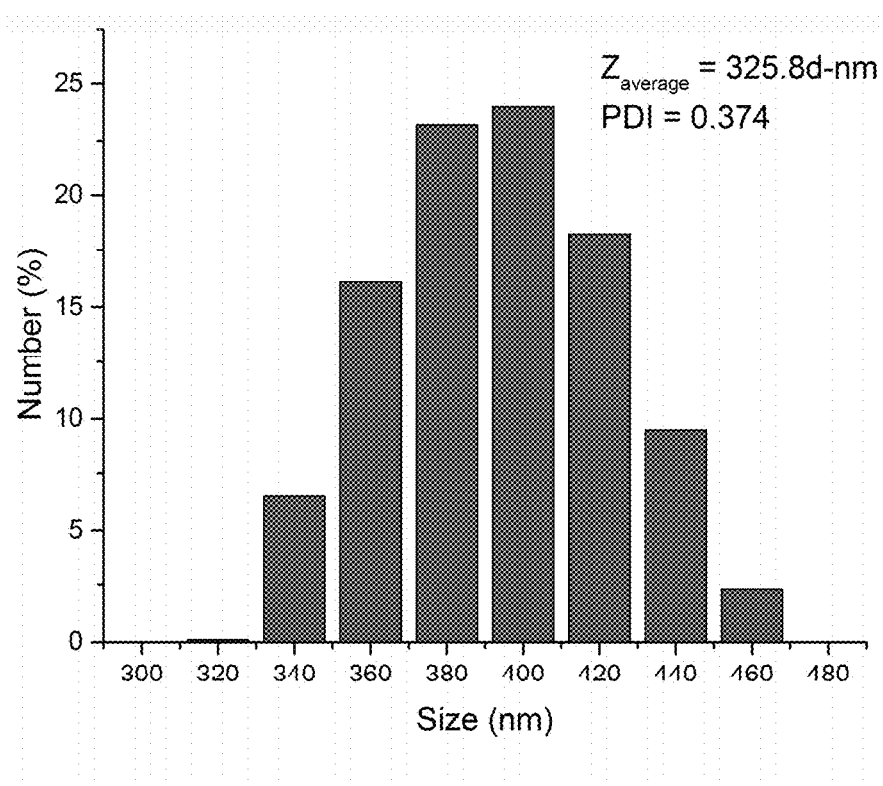

FIG. 35: DLS size distribution for 400 nm nanobubbles

Figure 36:
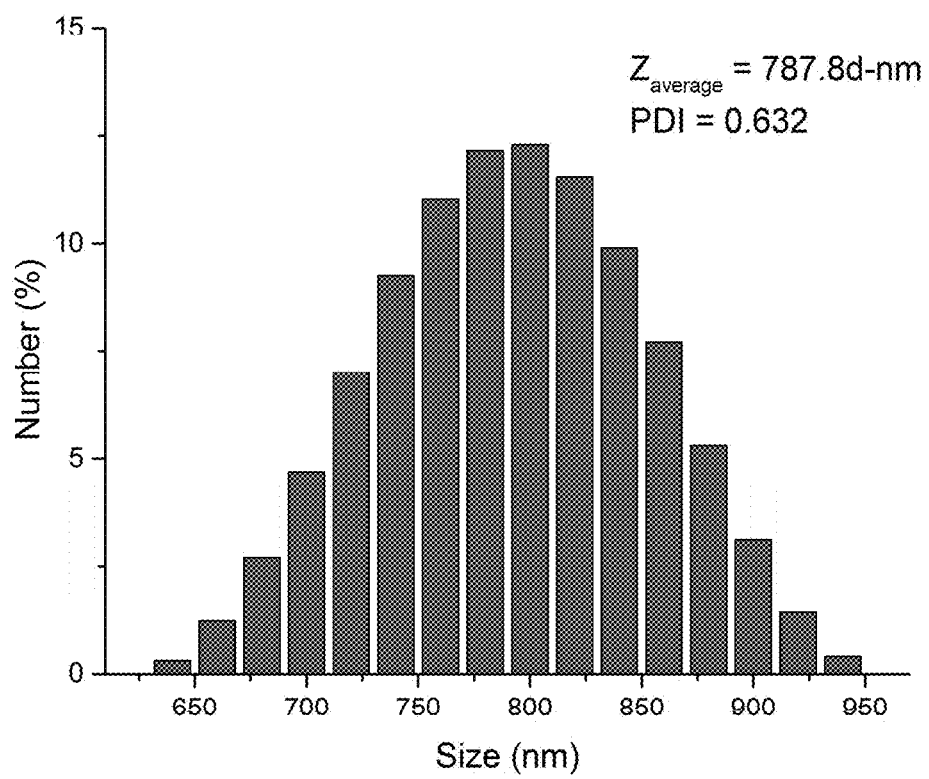

FIG. 36: DLS size distribution for 800 nm nanobubbles

Figure 37:
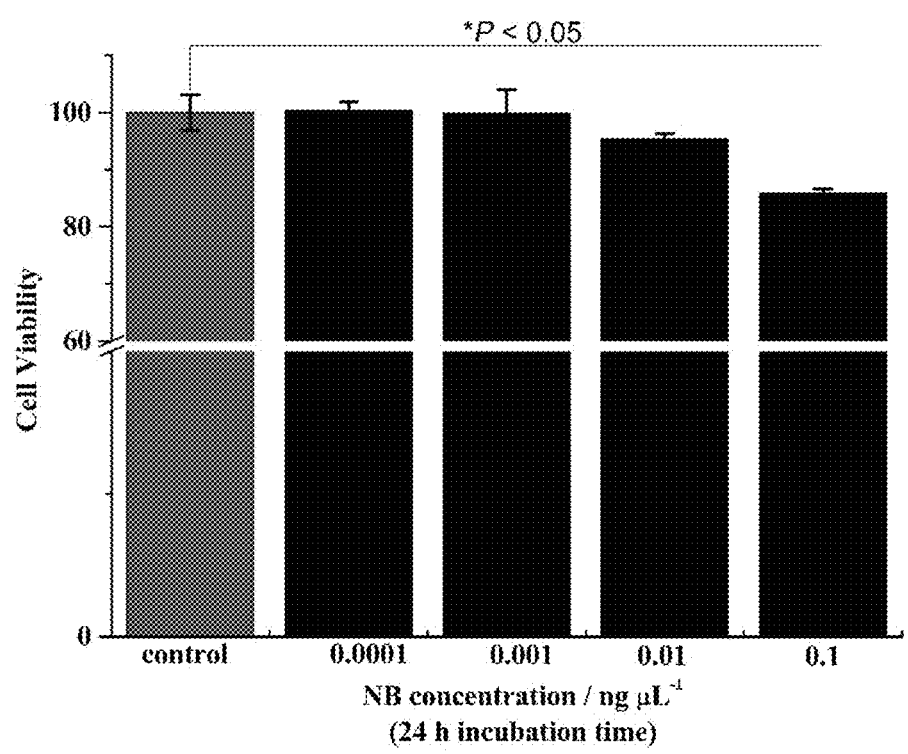

FIG. 37: Therapeutic potential of ONB for PC3 cell line with 24 h incubation time.

Figure 38:
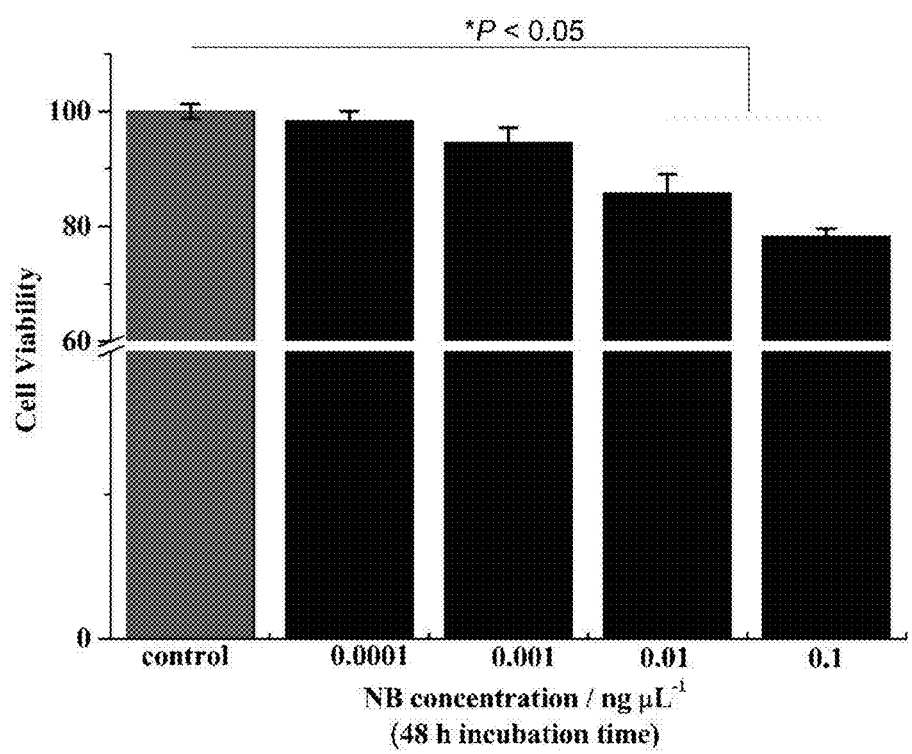

FIG. 38: Therapeutic potential of ONB for PC3 cell line with 48 h incubation time.

Figure 39:
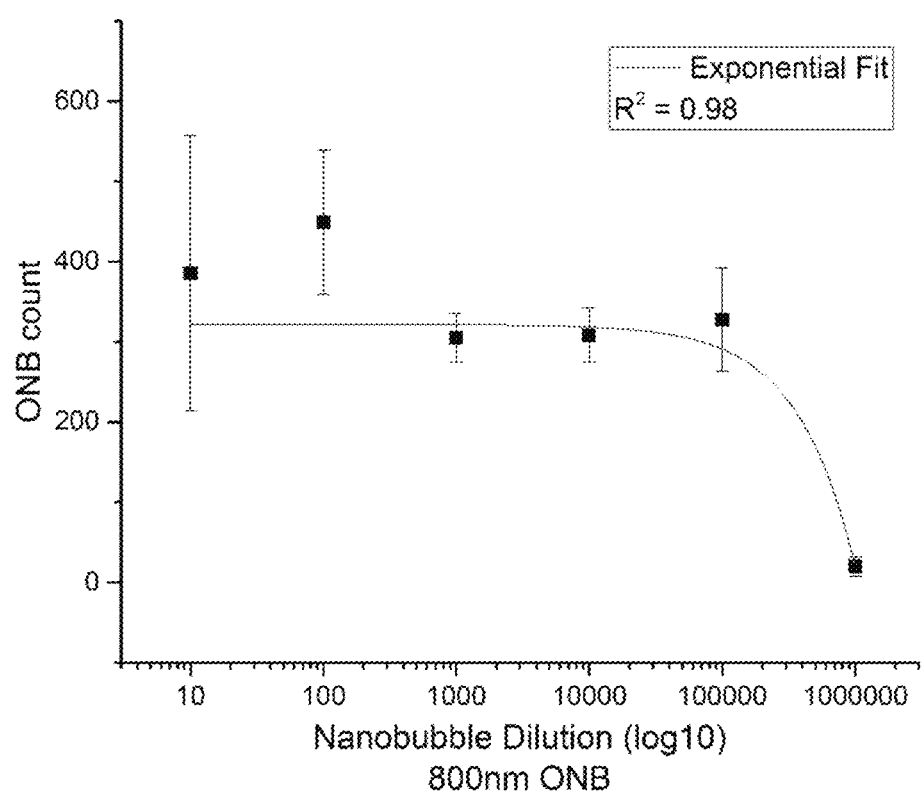

FIG. 39: 400 nm nanobubble quantification using dark-field imaging for in vitro assays.

Figure 40:
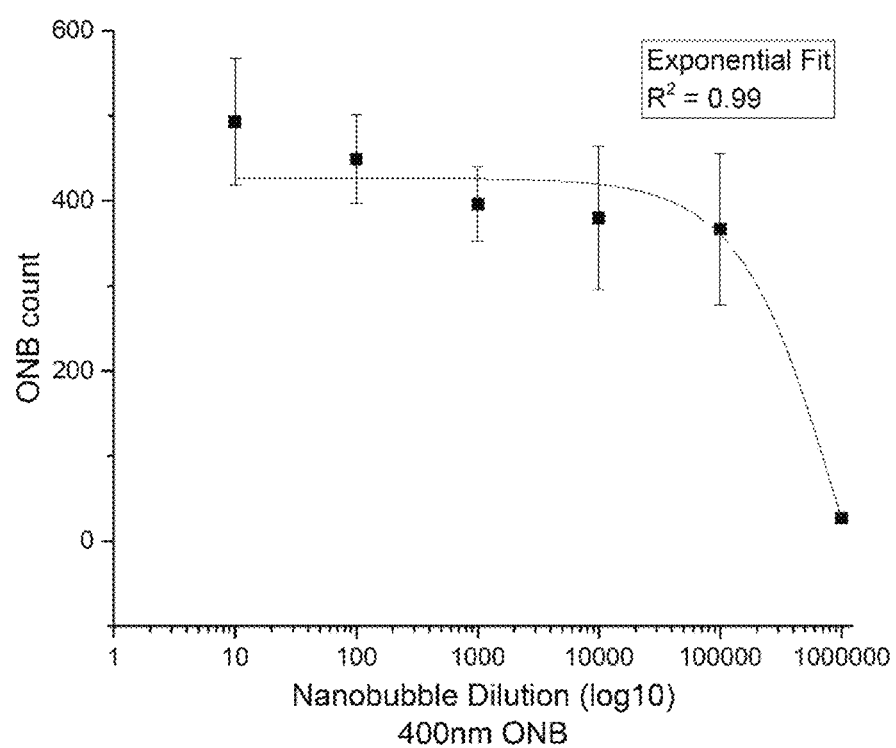

FIG. 40: 800 nm nanobubble quantification using dark-field imaging for in vitro assays.

Figures 41A, 41B, 41C:
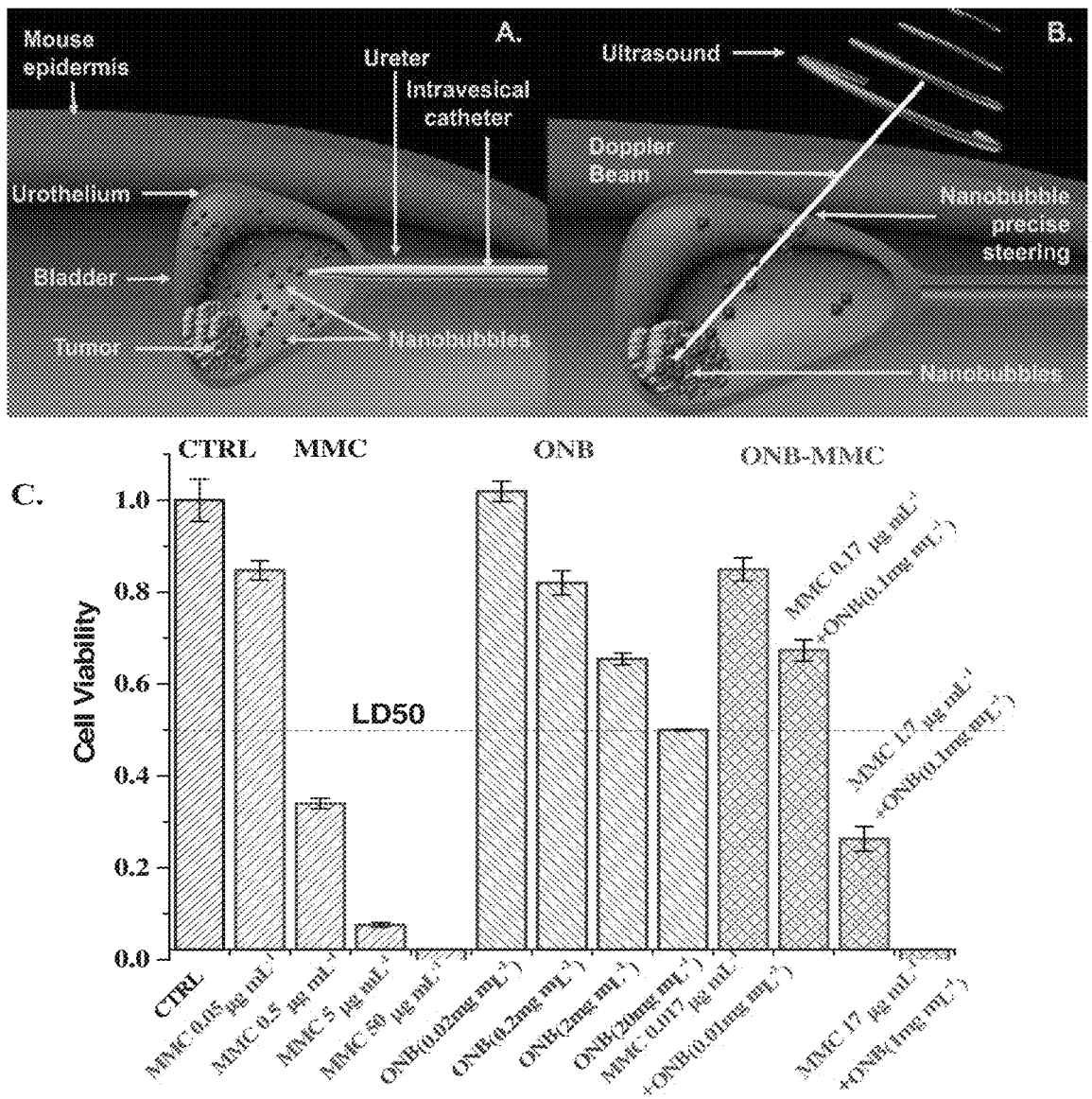

FIG. 41. Schematic of intravesical treatment in mice bladder cancer. (FIG. 41A) Therapy introduced into the bladder by intravesical catheter. (FIG. 41B) Precise localization of mitomycin-C loaded ONBs (in blue color) to the hypoxic tumor microenvironment using Doppler ultrasound steering with simultaneous B-mode US imaging. (Not to scale). (FIG. 41C) Oxygen nanobubbles can halve the dose of MMC required with enhanced therapeutic efficacy, in vitro. Cell viability measured using MTT assay for different conditions of CTRL, MMC, ONB, and ONB-MMC.

Figures 42A, 42B, 42C, 42D:
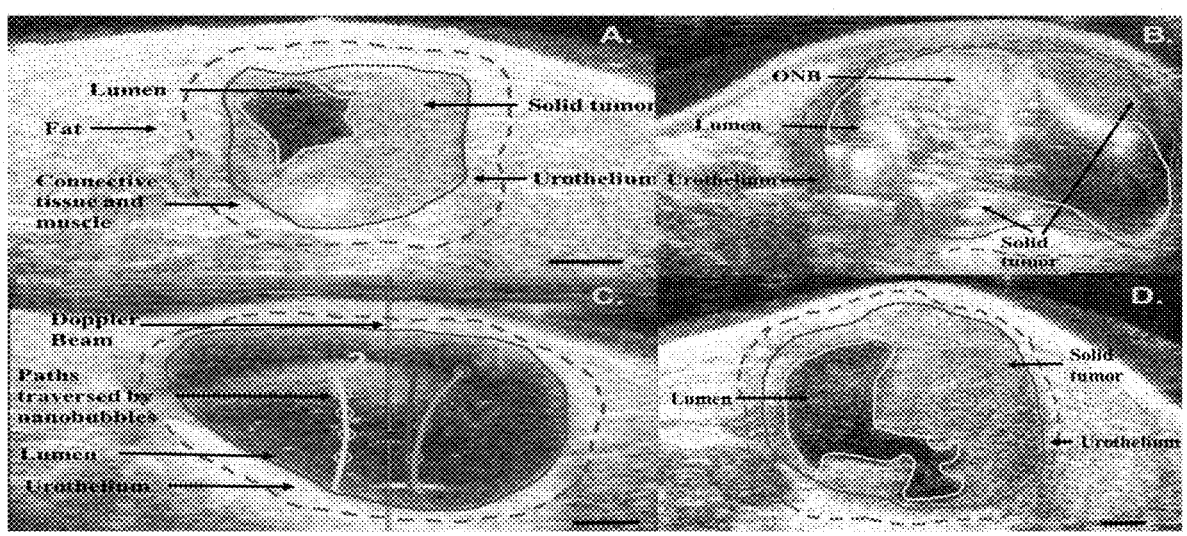

FIG. 42: Precise steering of nanobubbles to the urothelium tumor after bladder instillation in mouse models. (FIG. 42A) B-mode ultrasound image of mouse bladder (dotted blue outline) showing tumor (blue outline) and bladder lumen (yellow outline). (FIG. 42B) Bladder injected with ONBs significantly enhance ultrasound contrast. (FIG. 42C) Nanobubbles are propelled (trajectories for selected three ONB streams are highlighted) along the DUB at 0° angle relative to the transducer. (FIG. 42D) Day 10 B-mode ultrasound image showing moderate regression in tumor size.

FIG. 43. Ultrasound beam guiding of ONBs enhances therapeutic efficacy of MMC and reduces toxicity of treatment. (FIG. 43A) Reconstructed 3-D images of intravesical tumor for control (CTRL), MMC and ONB groups on day 3 and day 35. (FIG. 43B) Kaplan Meier survival curves for CTRL, MMC and ONB groups (n=8 mice per group). (FIG. 43C) Tumor volume dynamics for CTRL, MMC and ONB groups (n=8 mice per group). (FIG. 43D) Mice weight dynamics for CTRL, MMC and ONB groups (n=8 mice per group) (FIG. 43E). Partial pressure of oxygen in the CTRL group, ONB group after 48 h of injections and ONB group after 0 h injection (n=10).

Figures 44A, 44B:
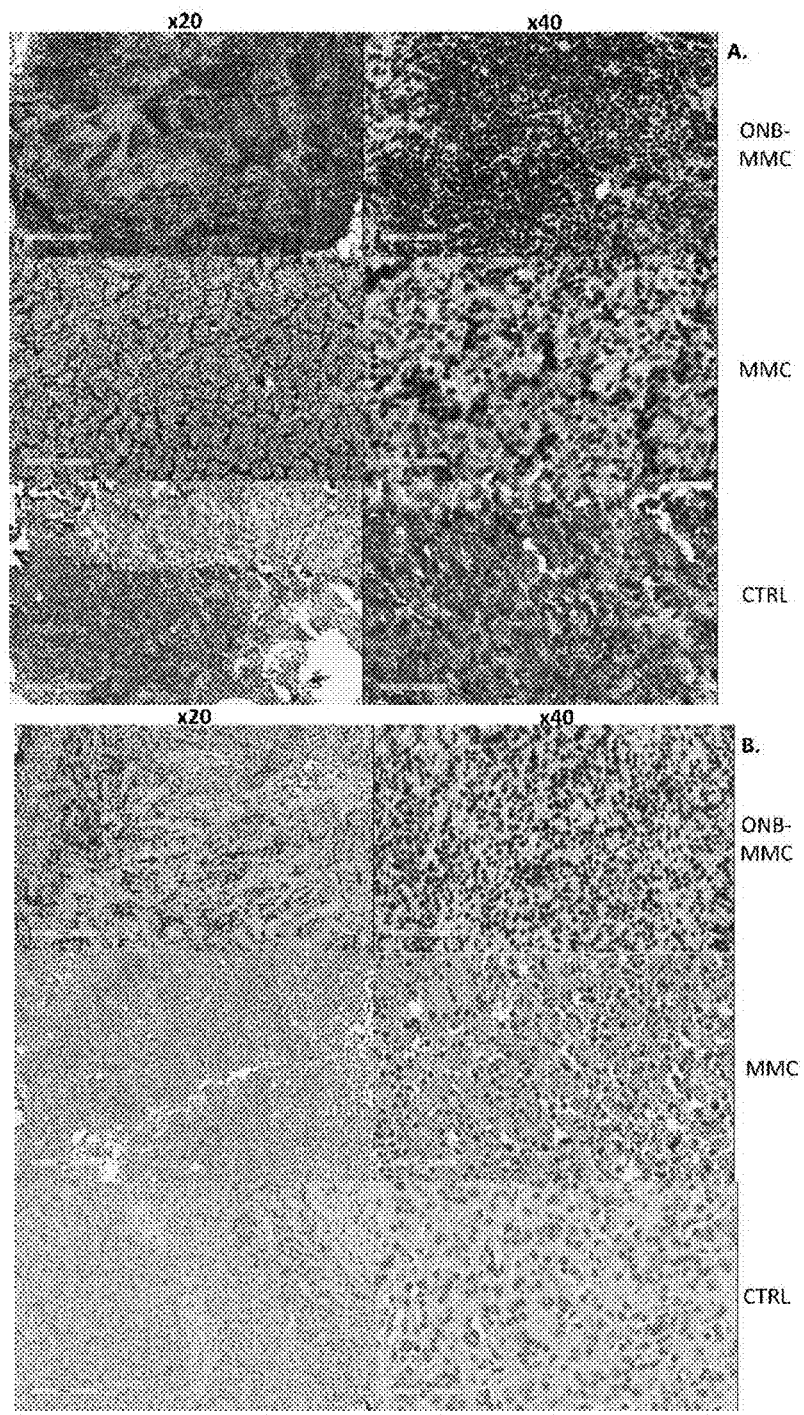

FIG. 44. Immunohistochemistry staining pattern of hypoxic morphology markers. Microscopic images of mouse bladder with MB49 tumors treated with saline (CTRL), MMC only, or ONB-MMC (magnification left panel ×20, scale bar=200 µm; right panel ×40, scale bar=100 µm): (FIG. 44A) Strong HIF-1 expression is observed in control tumors and weak positive expression in ONB treated tumors (brown cytoplasmic staining). (FIG. 44B) Representative IHC images show that VEGF expression levels were significantly lower in ONB-MMC treated groups compared to CTRL or MMC groups (P<0.05).

Figures 45A, 45B, 45C, 45D:
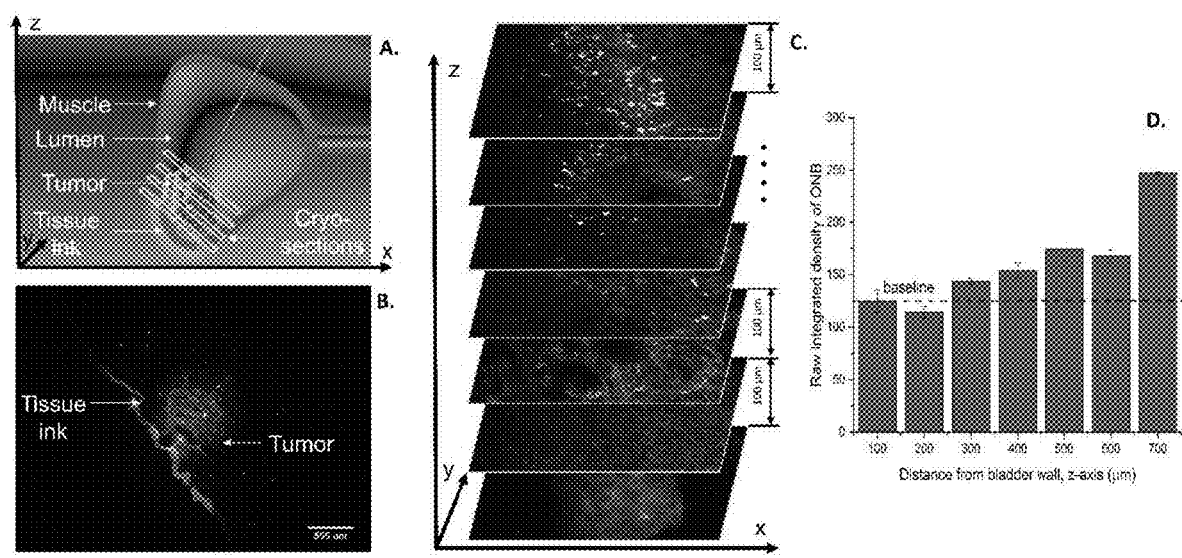

FIG. 45. Nanobubbles can be localized up to 500 µm inside the tumor using beam steering. (FIG. 45A) Schematic of bladder tumor stained with tissue ink during dissection to maintain orientation and cryosectioned using a cryotome. (FIG. 45B) Dark-field image showing tissue ink used for maintaining sample orientation and bladder tumor. Image obtained at ×10 magnification. Scale bar=500 µm. (FIG. 45C). Representative dark-field images showing localization of ONBs (bright spots) up to a depth of 500 µm inside the tumor. Cryosections were obtained at intervals of 100 µm and thickness of tissue sections was 10 µm. Bottom image (z-axis) represents bladder wall whereas top-most image represents the outer layer of tumor wherein ONBs penetrate using the Doppler beam. (FIG. 45D) Raw integrated density of ONBs shows significant accumulation of ONBs up to 300 µm from the bladder wall (500 µm from tumor periphery). Baseline represents background signal obtained from CTRL mouse bladder. The amount of ONBs decreases with distance from the tumor periphery.

Figure 46A:
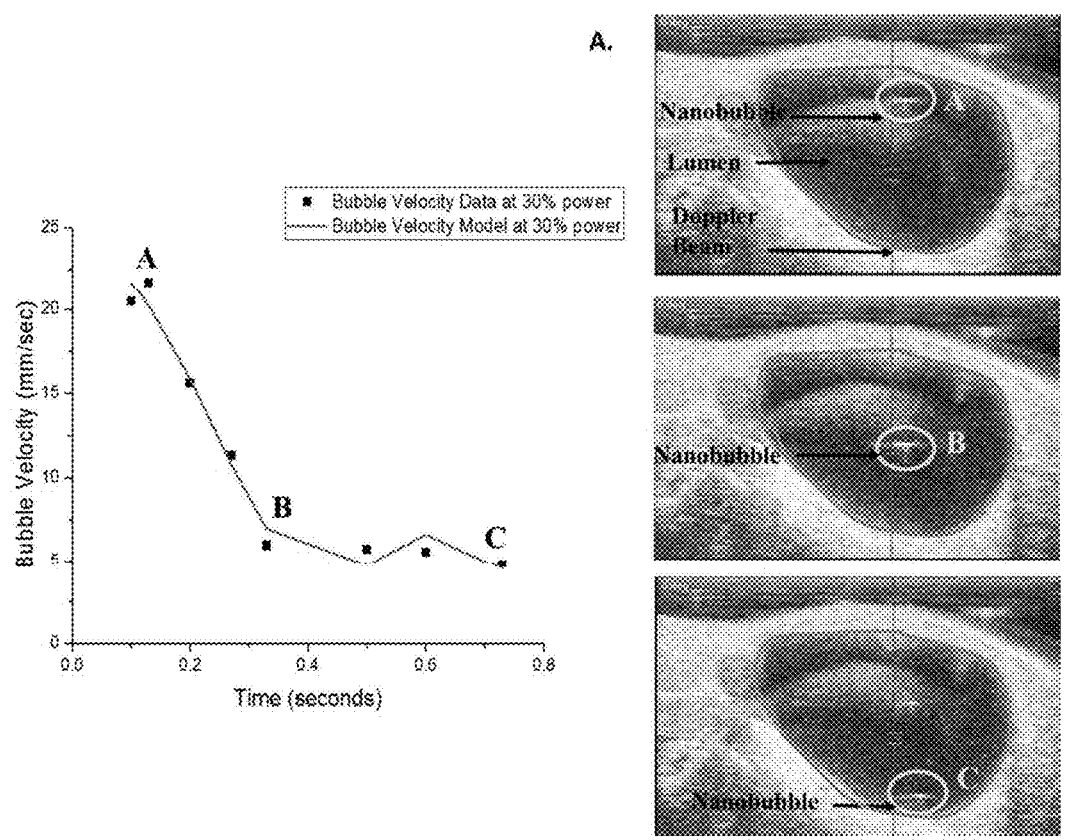
Figure 46:
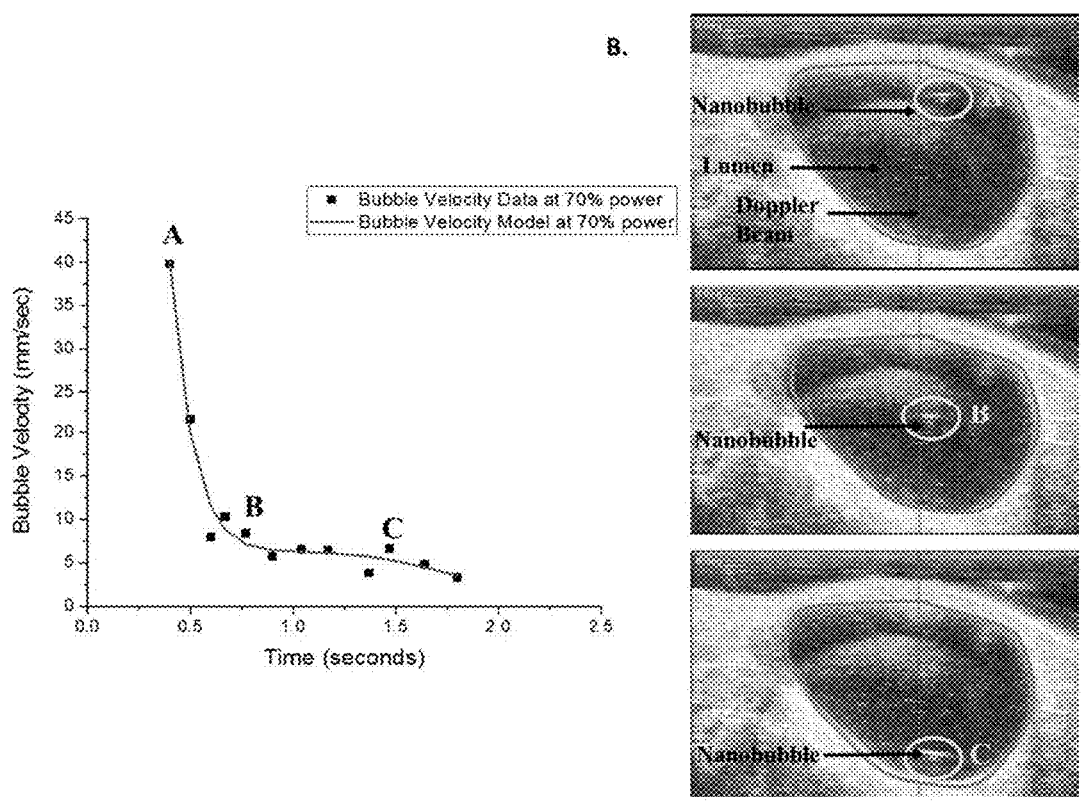
Figure 46:
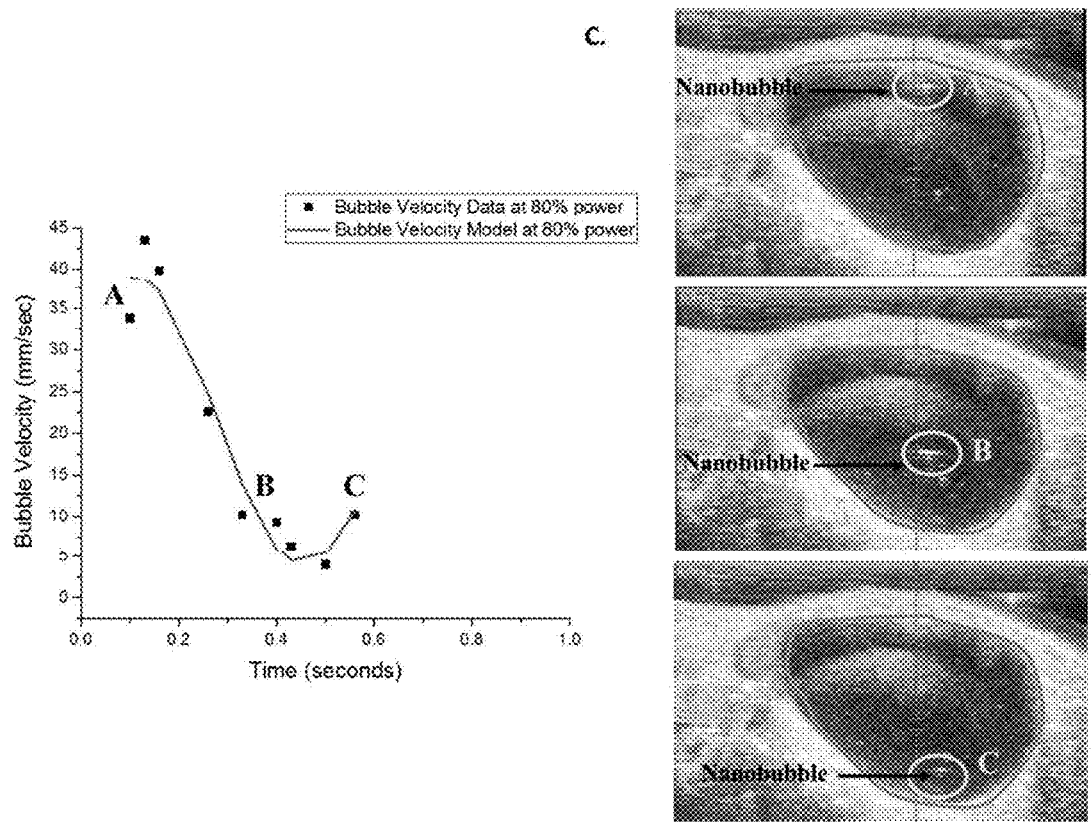

FIG. 46. Nanobubbles can be propelled at desired velocities by tuning the ultrasound Doppler beam power as predicted by the theoretical model. Nanobubble velocity data (black squares) and model (red line) for 30% (FIG. 46A), 70% (FIG. 46B), and 80% (FIG. 46C) ultrasound beam power. Points A, B, and C indicates the bubble's position at a given time.

FIG. 47: Contour plot for cell viability (%) with beam steering (top) and without steering (bottom). Ultrasound Doppler beam significantly reduced cell viability when ONB-MMC were both at medium concentrations.

Figure 48:
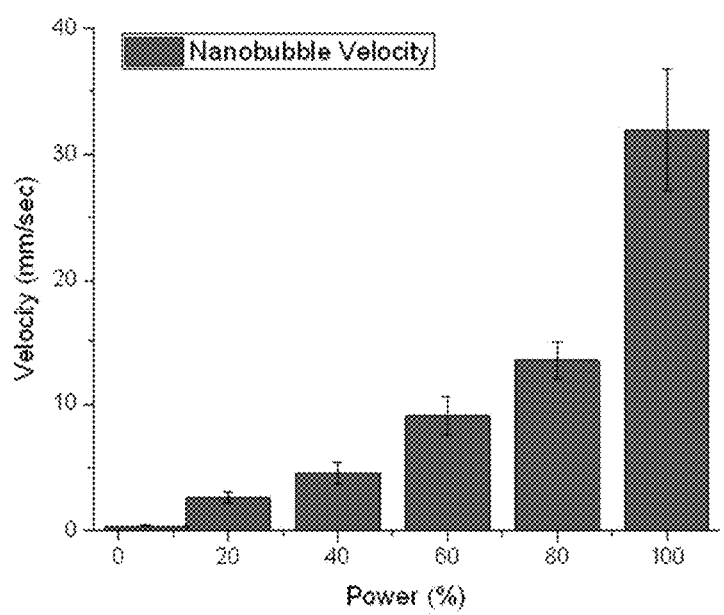

FIG. 48: ONB velocity increases with increase in ultrasound beam power.

TABLE 2

Factorial design to optimize in vitro parameters for MB49 cell viability.

| Parameter | Range | | Results |
|---|---|---|---|
| MMC | 0.05 µg/mL | Low | Significant |
| | 0.5 µg/mL | Medium | |
| | 5 µg/mL | High | |
| ONB | 0.2 mg/mL | Low | Significant |
| | 2 mg/mL | Medium | |
| | 20 mg/mL | High | |
| Beam steering | OFF | Low | Significant when ONB- |
| | ON | High | MMC are both at medium concentration |
| Cell Viability (Y) | 0-100% | | |

TABLE 3

Results of factorial design of experiments to identify significant parameters influencing nanobubble velocity. Utrasound beam frequency and power were significant in changing the velocity of ONB.

| Parameter | Estimate | F ratio | Prob > F |
|---|---|---|---|
| Intercept | 26.71 | 0.00 | 1 |
| ONB Size | 0 | 2.93 | 0.16 |
| Beam frequency | −1.03 | 45.69 | 0.001 |
| Beam power | 0.654 | 18.45 | 0.007 |
| Beam angle | 0 | 0.35 | 0.587 |

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

A novel composition is described. A nanobubble having a continuous outershell, an inner wall of the continuous outer shell, and a hollow core. In certain aspects the composition is a hollow, sphere or sphere-like shaped nanobubble ranging in size of about 10 nm diameter to about 250 nm diameter across. In certain aspects the hollow core of the nanobubble comprises biomolecules, liquids, small molecules, imaging agents, ultrasound contrast agents, or gases. In certain aspects the nanobubble is configured to image at least one cell, configured to deliver cargo to at least one cell, or configured to deliver a gas to at least one cell. In certain aspects the nanobubble is targeted to a specific cell or tissue. In certain aspects the nanobubble is configured to burst during a specific or range of frequencies provided by sound waves.

By "tissue" refers generally to specialized cells which may perform a particular function. It should be understood that the term "tissue," as used herein, may refer to an individual cell or a plurality or aggregate of cells, for example, membranes or organs. The term "tissue" also includes reference to an abnormal cell or a plurality of abnormal cells. Exemplary tissues include, for example, myocardial tissue (also referred to as heart tissue or myocardium), including myocardial cells and cardiomyocites, membranous tissues, including endothelium and epithelium, laminae, connective tissue, including interstitial tissue, and tumors.

By "patient" refers to mammals, including humans, mouse, dog, cat, cow, pig, or horse.

By "internal region of a patient" and "region of interest" refer to the entire patient or to a particular area or portion of the patient. Internal regions of a patient and regions of interest may include, for example, areas being imaged with diagnostic imaging and/or areas being treated with a bioactive agent. Exemplary of such areas include, for example, the heart region, including myocardial tissue, as well as other bodily tissues, including the vasculature and circulatory system and cancerous tissue. The phrase "vasculature," as used herein, denotes the blood vessels in the body or in an organ or part of the body.

By "effective therapeutic amount" refers to an amount of a small molecule or biomolecule that is able to ameliorate, inhibit proliferation, reduce proliferation, or increase proliferation depending on the desired effect, type of molecule used, and concentration.

By "biomolecule" refers to substances which are capable of exerting a biological effect in vitro and/or in vivo. The bioactive agents may be neutral or positively or negatively charged. Examples of suitable bioactive agents include diagnostic agents, pharmaceuticals, drugs, synthetic organic molecules, proteins, peptides, vitamins, steroids and genetic material, including aptamers, nucleosides, nucleotides and polynucleotides.

By "biocompatible" refers to materials which are generally not injurious to biological functions and which will not result in any degree of unacceptable toxicity, including allergenic responses and disease states.

By "receptor" refers to a molecular structure within a cell or on the surface of the cell which is generally characterized by the selective binding of a specific substance. Exemplary receptors include, for example, cell-surface receptors for peptide hormones, neurotransmitters, antigens, complement fragments, and immunoglobulins and cytoplasmic receptors for steroid hormones. An exemplary receptor within the context of the present invention is the glycoprotein GPIIbIIIa, which is a platelet integrin.

By "small molecule" or "pharmaceutical" or "drug" refers to any therapeutic or prophylactic agent which may be used in the treatment (including the prevention, diagnosis, alleviation, or cure) of a malady, affliction, disease or injury in a patient. Therapeutically useful peptides, polypeptides and polynucleotides may be included within the meaning of the term small molecule pharmaceutical or drug.

By "targeting agent" refers to refers to any material or substance which may promote targeting of tissues and/or receptors in vivo or in vitro with the compositions of the present invention. The targeting agent may be synthetic, semi-synthetic, or naturally-occurring. Materials or substances which may serve as targeting agents include, for example, proteins, including antibodies, glycoproteins and lectins, peptides, polypeptides, saccharides, including mono- and polysaccharides, vitamins, steroids, steroid analogs, hormones, cofactors, bioactive agents, and genetic material, including nucleosides, nucleotides and polynucleotides.

By "burst frequency" refers to the frequency or frequency range required to rupture the outer shell of the nanobubble to expose the cargo or inner contents within the hollow core to the outside environment, wherein the outside environment is in vivo or in vitro.

By "polymer" refers to molecules formed from the chemical union of two or more repeating units. Accordingly, included within the term "polymer" may be, for example, dimers, trimers and oligomers. The polymer may be synthetic, naturally-occurring or semisynthetic.

By "tumor" or "tumor cells" refers to an aggregate of abnormal cells and/or tissue which may be associated with diseased states that are characterized by uncontrolled cell proliferation. The disease states may involve a variety of cell types, including, for example, endothelial, epithelial and myocardial cells. Included among the disease states are neoplasms, cancer, leukemia and restenosis injuries.

By "power or intensity" refers to the sound power and sound intensity, which are well defined in the field of physics. Briefly sound power is the amount of energy produced over a given period of time from a mechanical motion such as vibration. Sound intensity is related to sound power in that it describes the sound power over a given physical area.

The composition of a nanobubble may comprise an outer shell of a polymer material. This polymer material is chosen from the group consisting of sodium carboxymethyl cellulose (NaCMC), cellulosic materials, polyethylene glycol (PEG), chitosan, sodium hyaluronate, poly(lactic-co-glycolic acid, polystyrene, hydrogels, superdisintegrants, pharmaceutical excipients, sodium starch glycolate, poly (vinyl pyrrolidone), microcrystalline cellulose, hydroxypropylmethyl cellulose, HPMC phthalate, oxycellulose, sodium stearyl fumarate, alpha cellulose, pre gelatinized starch, starch acetate, albumin, dextran, or chitosan. The outer shell of a polymer material is cross-linked. General ways to crosslink include chemical means, photo-reactive means, thermal means, pH means, electron beam exposure, gamma radiation, UV radiation, oxidative crosslinking, or photochemical all of which are known to those of ordinary skill in the art. The continuous outershell of the nanobubble may include pores generated by the polymer material, the cross-links, or both.

The outer shell of the nanobubble may also comprise fluorophores, small molecules such as pharmaceuticals, biomolecules such as growth factors, glucose, steroids, ligands for targeting such as prostate-specific membrane antigen PSMA or folate, sticky molecules, ultrasound contrast imaging agents, antibodies in whole or in part, lipids, protein receptors, or aptamers such as an oligonucleic acids or peptide molecules. These additional elements may be added as single additions or in combinations on a single nanobubble. For example, a nanobubble may comprise an outer shell material including a targeting ligand and a small molecule. The nanobubble may comprise an outer shell material and an antibody. The purpose of these additional elements are for various applications including imaging, targeting, treating, or causing a molecular response to at least one cell or tissue.

The hollow core of the nanobubble will have about the same diameter as the nanobubble itself. The hollow core may comprise cargo of a solid, liquid or gas for various applications. Additional elements described previously, fluorophores, small molecules such as pharmaceuticals, biomolecules such as growth factors, glucose, steroids, ligands for targeting such as prostate-specific membrane antigen PSMA or folate, sticky molecules, antibodies in whole or in part, ultrasound contrast imaging agents, lipids, protein receptors, or aptamers such as an oligonucleic acids or peptide molecules, may be bound to the inner wall of the outer shell and directed towards the hollow core of the nanobubble. The additional elements in the hollow core may be free-floating, or unattached to the inner wall of the outer shell of the nanobubble. The hollow core may comprise a gas including but not limited to oxygen, nitrogen, carbon dioxide, plasma, perfluorocarbons, perfluorohexane, or tetradecafluorohexane. The hollow core of the nanobubble may comprise a liquid including but not limited to water, contrast imaging agents, saline solution, perfluorocarbon, fluorinated liquids, liquid drug formulations, nitric oxide, chemical oxygen generators, or oxygen release compounds.

The nanobubble may be configured carry a cargo of solid, liquid, or gas. A means for carrying cargo is described and illustrated in example 1 and 2 of this application. The nanobubble may be configured to carry a combination of cargo including ratios of at least two solid:solid, solid:liquid, solid:gas, liquid:liquid, liquid:gas, gas:gas, or solid:liquid:gas. The nanobubble's cargo is only limited by the amount of cargo that can fit into the available space in the hollow core of the nanobubble.

The nanobubble may be configured to burst under certain conditions. In one aspect the nanobubble is configured to burst at a given frequency or power or intensity of sound wave or any external form of energy source such that the nanobubbles resonate and burst. The frequency or power or intensity at which the nanobubble bursts may be tuned and is controlled in part by the polymer material and number and type of cross links. For example, by increasing the number of cross-links comprising the outershell of the nanobubble may increase the burst frequency required to burst the nanobubble. In another aspect the size of the nanobubbles can be tuned to initiate bursting at different frequencies or power or intensity. Thus multi-modal drug release is possible where timely and sequential release can be programmed and a plurality of nanobubbles tuned to release a plurality of drugs only upon excitation by that frequency or power or intensity. One of skill in the art will recognize that different applications will require different burst frequencies or power or intensity. As a non-limiting example, the nanobubble may be configured to burst at 1.1 MHz over a range of about 0.01 to about 1,100 mv/cm$^3$, wherein 50 percent (%) of the nanobubbles configured to burst in this range will burst at about 70 mv/cm$^3$. In another non-limiting example, the nanobubble may be configured to burst at 2.2 MHz over a range of about 0.01 to about 400 mv/cm$^3$, wherein 50% of the nanobubbles configured to burst at this frequency will burst at about 30 mv/cm$^3$. A plurality of nanobubbles may be generated to burst at different frequencies depending on the application. This heterogenous mix of nanobubbles may be delivered to a mammal or patient at or about the same time or at different times.

The nanobubbles may be delivered in vitro or in vivo. Methods of delivering the nanobubbles will be understood to those of skill in the art. Methods of delivery include but are not limited to, injection, inhalation, intravascular, intradermal, catheter, injection into a port, oral delivery, or transmucosal. The nanobubbles may delivered with an acceptable pharmaceutical carrier including but not limited to saline, of which is well known in the art.

In certain applications, the nanobubbles may be configured to deliver oxygen to at least one cell, group of cells, or tissue. The amount of oxygen carried in a nanobubble is dependent on the nanobubble's size but may range in concentration from about 20,000 to 200,000 ppm. If the nanobubble comprises pores, some of the oxygen will diffuse out from the inner core and through the continuous outer shell. These nanobubbles configured to carry oxygen may be delivered by any of the previously described mechanisms.

Nanobubbles comprised to carry oxygen may be used as contrast imaging agents or as a therapeutic. See below examples 1 through 3. If the nanobubble is used to deliver oxygen as a contrast agent, it may be provided in combination with other known contrast imaging agents. The combination may be delivered in a single nanobubble, in separate nanobubbles, or an oxygen comprising nanobubble and a contrast imaging agent not associated with a nanobubble. The oxygen comprising nanobubble may also include targeting agents to direct the nanobubble to a specific cell or tissue type of interest. Targeting agents are well known to those of skill in the art and include but are not limited to EGF, VEGF, PSMA, antibodies in whole or in part, or folate.

Nanobubbles configured to carry oxygen and be used as a therapeutic may be delivered in combination with other therapeutics. The combination of therapeutics may be delivered in a single nanobubble, separate nanobubbles, or an oxygen comprising nanobubble and a therapeutic not associated with a nanobubble. The nanobubble configured to carry oxygen in combination or not with a therapeutic will be configured to burst at a specific frequency to burst the nanobubble and fully deliver its cargo contents to the surrounding cells or tissue. The oxygen comprising nanobubble for use as a therapeutic may be targeted using a targeting molecule. Targeting agents are well known to those of skill in the art and include but are not limited to EGF, VEGF, PSMA, antibodies in whole or in part, or folate. In certain aspects the nanobubble comprising oxygen as a therapeutic will not have a targeting agent and instead will be delivered to a diseased cell, such as cancer, through "leaky vasculature" through a phenomenon known as enhanced permeability and retention (EPR). This phenomenon is well known in the art and is taken advantage of by many in the cancer therapeutic space.

Example 1 Method of Producing Nanobubbles

Our approach was to cross link a sodium carboxymethyl cellulose (NaCMC) hydrogel (FMC Biopolymer) while encapsulating the oxygen nanobubbles inside the gel using a layer-by-layer (LBL) approach. Carboxymethyl cellulose is a FDA-approved pharmaceutical excipient that is non-cytotoxic and inexpensive, and possesses large drug-loading capacity and robust chemistry. Briefly, sodium carboxymethyl cellulose (Ac-Di-Sol, FMC Biopolymer, Philadelphia, PA) was dissolved in nanopure water to form a 0.1% (w/v) gel and homogenized and saturated with oxygen gas (UHP grade). The oxygen inlet was connected with an air nozzle (Nano Super Air Nozzle 1110SS, EXAIR Corporation) and a 20 nm membrane filter (Emflon II, Pall Corporation) to help generate oxygen nanobubbles. Further, the carboxymethyl cellulose solution was sonicated simultaneously with a probe horn (Cell Disruptor, Ultrasonic Power Corporation) and a bath sonicator (Model 2210, Branson Ultrasonics) since ultrasonic energy helps sonic compression of oxygen microbubbles to produce oxygen nanobubbles in the solution. 1% aluminium chloride ($AlCl_3$) cross linking agent was added to form the encapsulation structure under continuous ultrasonication. Aluminium chloride is a trivalent crosslinker and helps decrease the drug release rate compared to bivalent crosslinkers. Aluminium chloride also serves as a strong electrolyte and increases the electrostatic repulsive force to balance out the size reduction forces of the nanobubble, thus stabilizing the nanobubble. The pH of the resulting nanobubble suspension was neutralized to pH 7 using 0.1% ammonium hydroxide ($NH_4OH$) solution added dropwise.

Figures 2A, 2B:
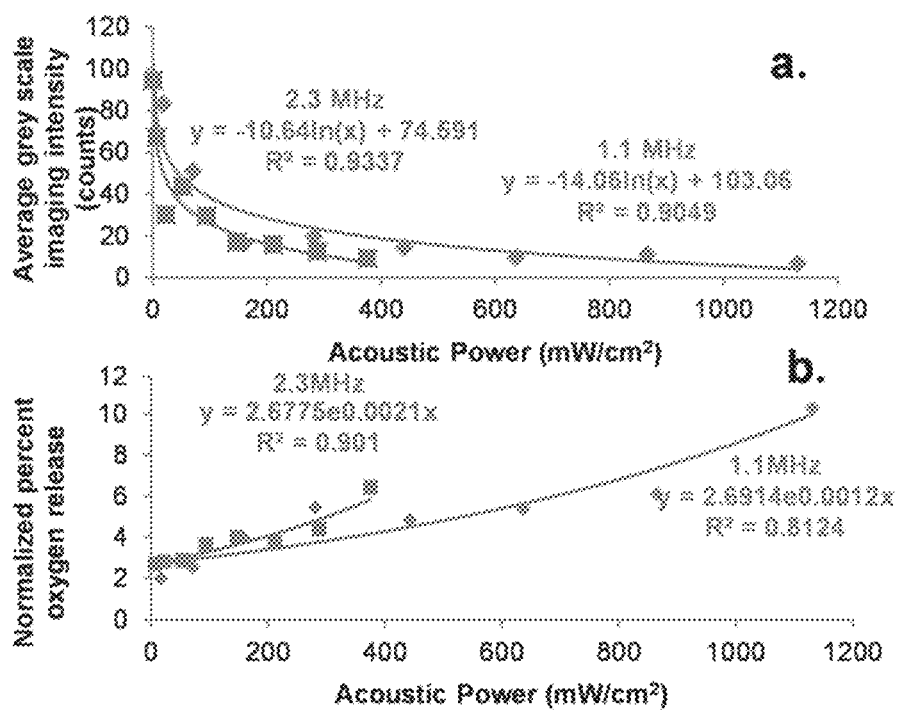
FIG. 2A is a graph showing ultrasound imaging intensity upon external ultrasound triggering of the nanobubbles at 1.1 MHz and 2.3 MHz, wherein the mean ultrasound imaging intensity decreases logarithmically and average oxygen release increases exponentially ($R^2 > 0.80$) at both frequencies.
FIG. 2B is a graph showing oxygen release upon external ultrasound triggering of the nanobubbles at 1.1 MHz and 2.3 MHz, wherein the mean ultrasound imaging intensity decreases logarithmically and average oxygen release increases exponentially ($R^2 > 0.80$) at both frequencies.
Figure 3:
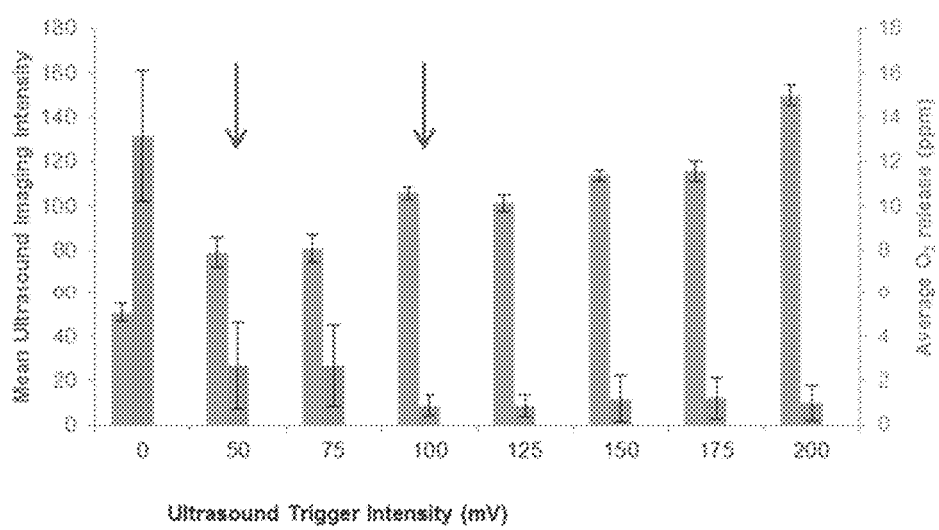
FIG. 3 is a graph showing ultrasound imaging intensity and oxygen release upon a longitudinal ultrasound trigger of the nanobubbles, where in the mean ultrasound imaging intensity decreases and average oxygen release increases significantly (*$p < 0.001$) at external ultrasound trigger intensities of 50 and 100 millivolts (mV) (arrows)
Figure 4:
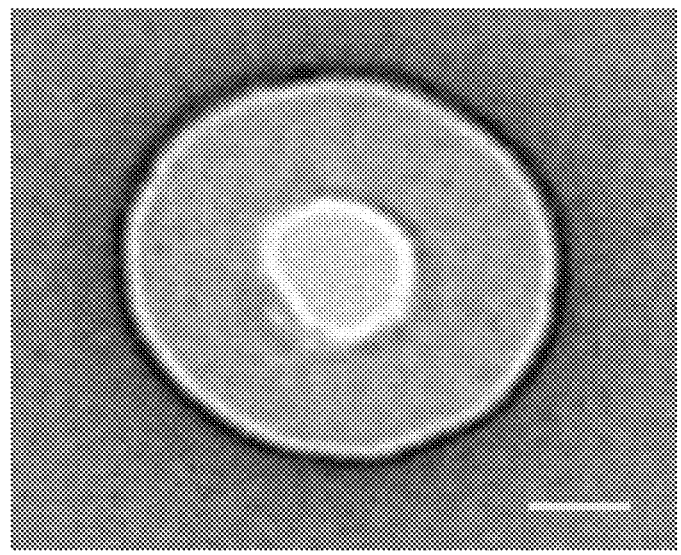
FIG. 4 is a transmission electron microscopy image of a nanobubble with an oxygen compartment in the inner core and surrounded by a cellulosic outer shell, wherein the scale bar equals 50 nanometers (nm)
Figure 5:
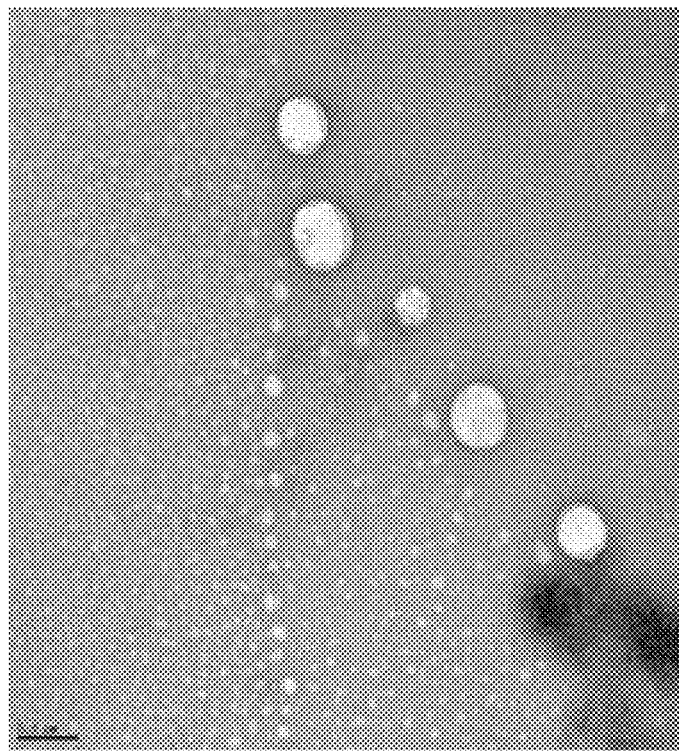
FIG. 5 is a transmission electron microscopy of nanobubbles showing size distribution of 20-200 nm, wherein the scale bar equals 100 nanometers (nm)
Figure 6:
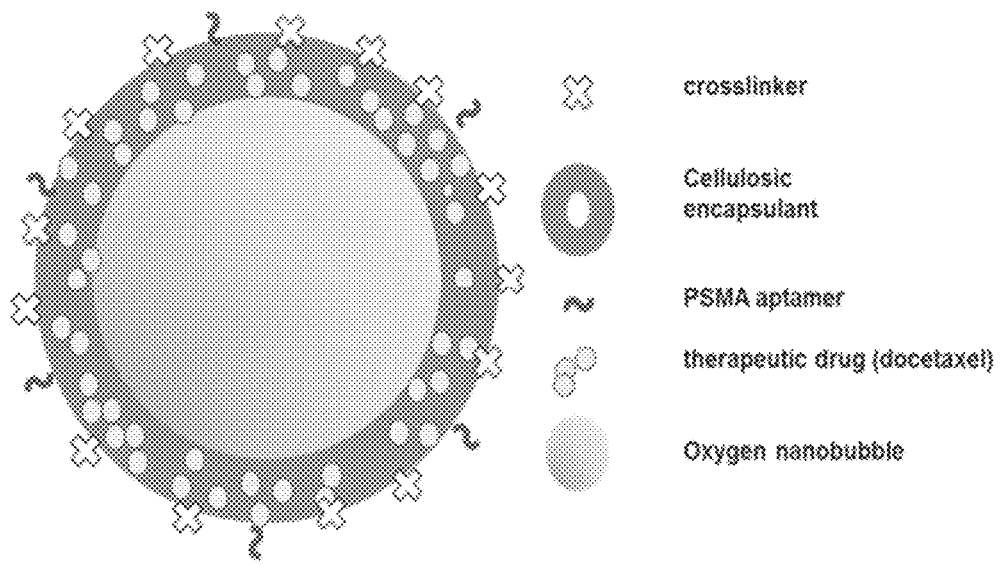
FIG. 6 is a graphic representation of one embodiment of a nanobubble incorporating a therapeutic drug and a targeting agent in a crosslinked, cellulosic outer shell, and a hollow inner core comprising oxygen.
Figure 7:
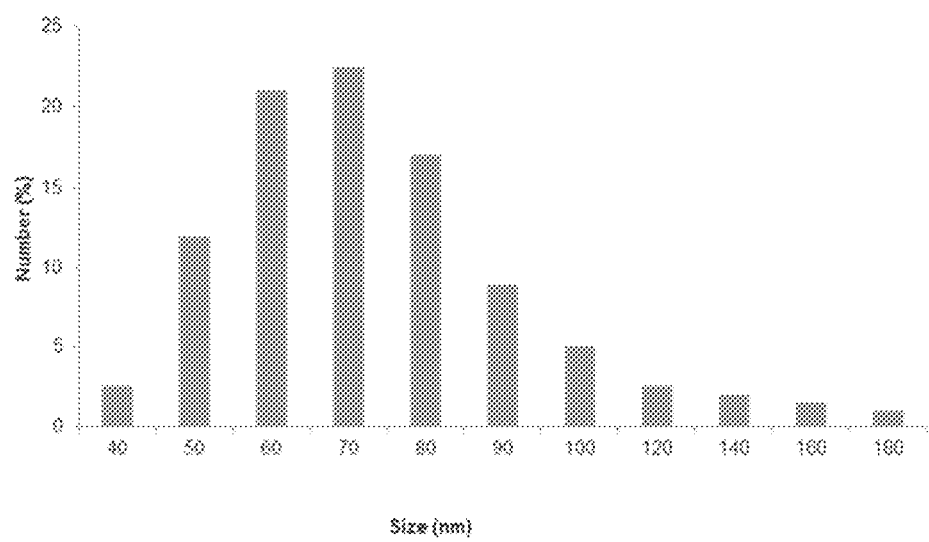
FIG. 7 is a graph showing the range of diameters or sizes of the nanobubbles produced during several experiments, with the most common size ranging between 60 and 80 nm.
Figure 10:
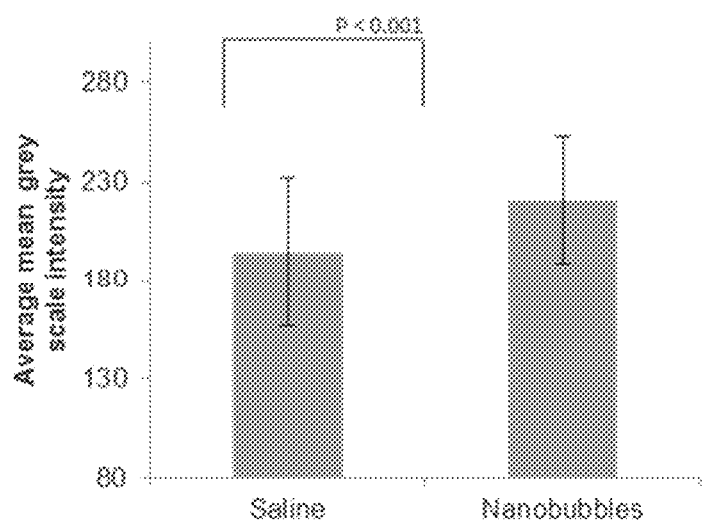
FIG. 10 is a graph showing the averaged mean grey scale intensity within the region of interest corresponding to the injected solutions (i.e. nanobubbles or saline), and note that there is significant difference between the two images suggesting a strong ultrasound contrast generated in vivo using the nanobubbles.
Figure 11:
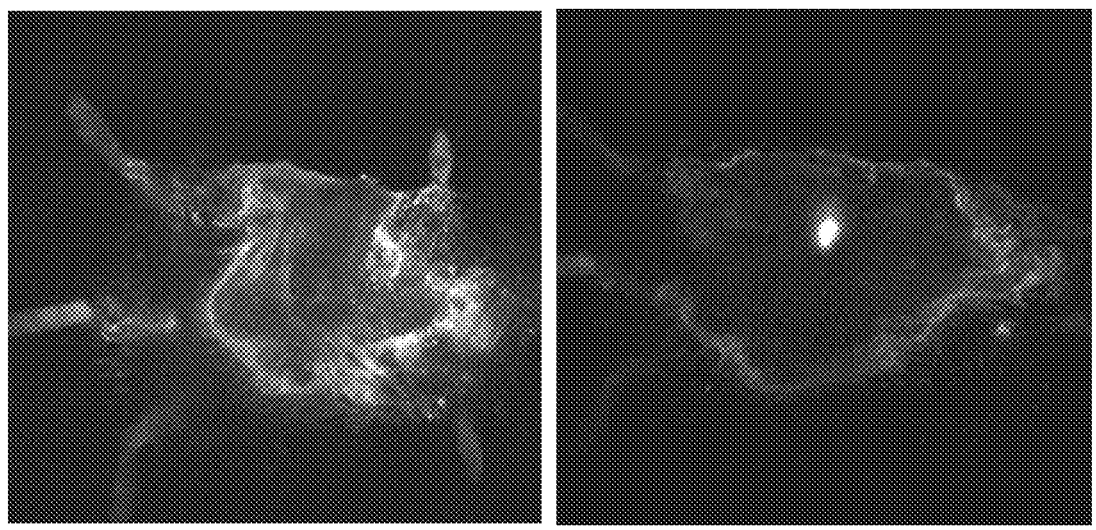
FIG. 11 shows two images with the one on the right showing the autofluorescence of a mouse's whole body after being injected with saline, and the image on the left showing the autofluorescence of a mouse's whole body upon being injected subcutaneously with nanobubbles, thus illustrating significant fluorescence intensity enhancement and nanobubble localization.
Figure 12:
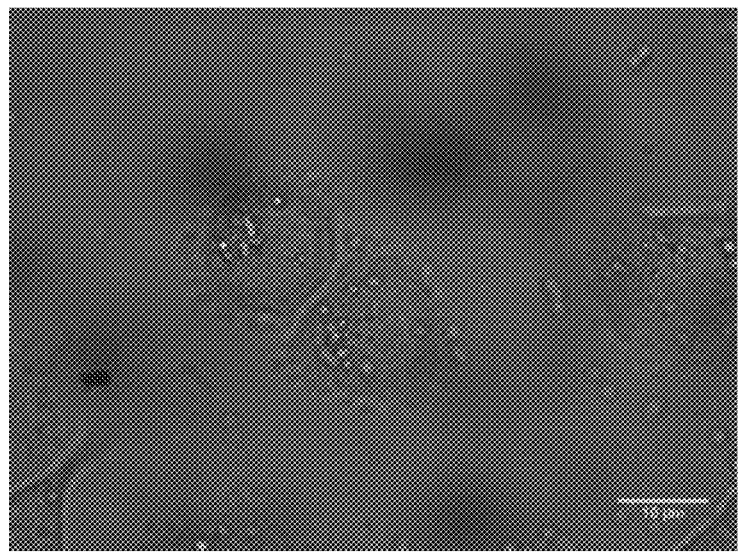
FIG. 12 is a bright field microscope image of HeLa cells that have taken up nanobubbles comprising oxygen and a fluorescence molecule FitC.
Figure 13:
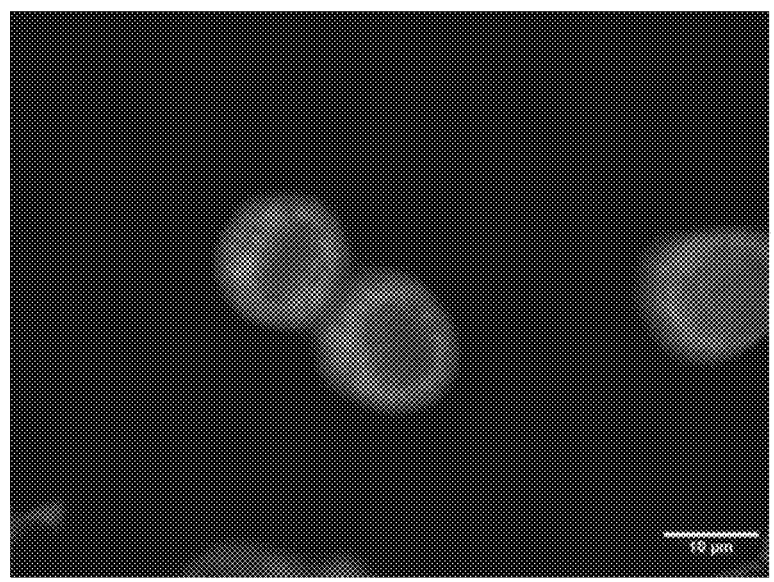
FIG. 13 is an epifluorescence microscope image (488 nm emission rays) of HeLa cells which have taken up nanobubbles comprising oxygen and FitC, and the location of the fluorescent molecules signifies the localized position of the nanobubbles.
Figure 14:
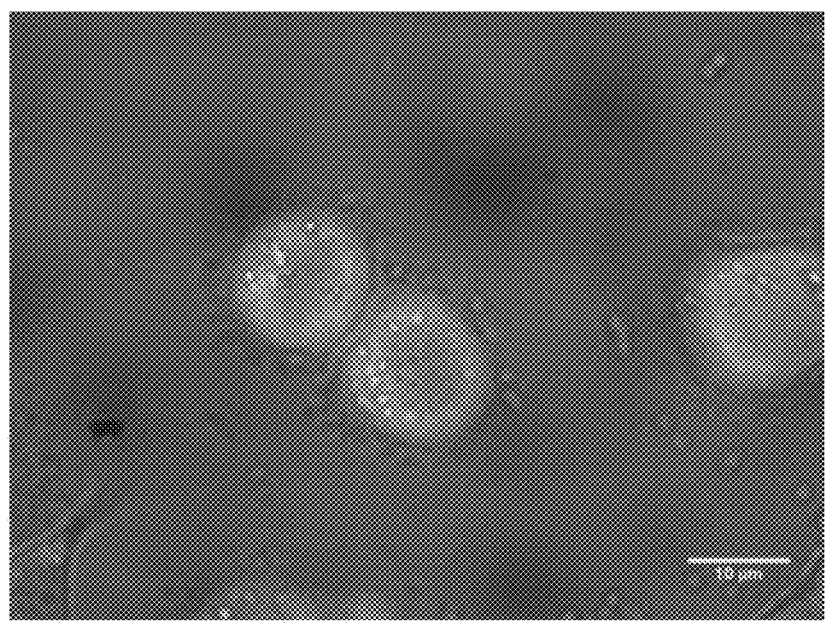
FIG. 14 is a superimposition of the bright field and the fluorescent images, wherein the fluorescent signal is strongest over the position of the cells, and thus it is concluded that the nanobubbles have been taken up by the cells thereby concentrating inside the cells.
Figure 15:
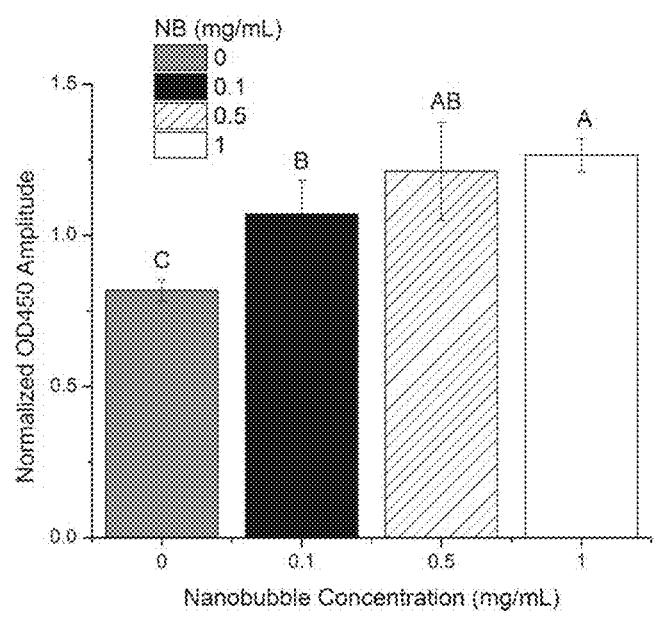
FIG. 15 is a graph showing 5mC methylation levels as measured against varying concentration of nanobubble treatments.
Figure 16:
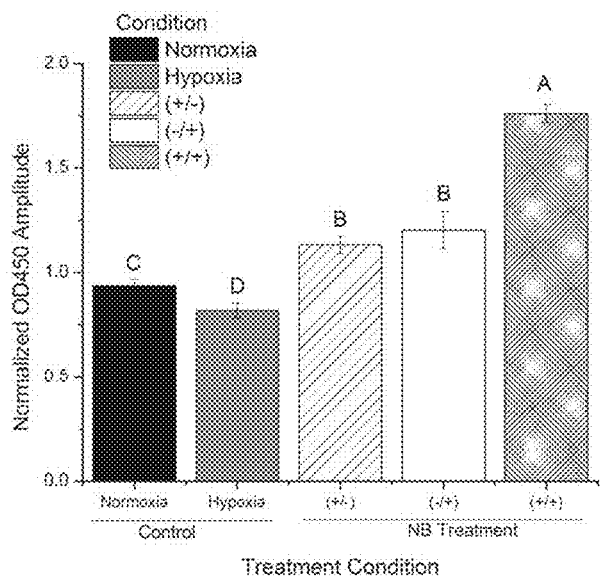
FIG. 16 is a graph showing 5mC methylation levels as measured for the varying treatments, and 0.5 mg/mL nanobubble concentration, to identify the relation between treatment frequency and the total time of incubation.
Figure 17:
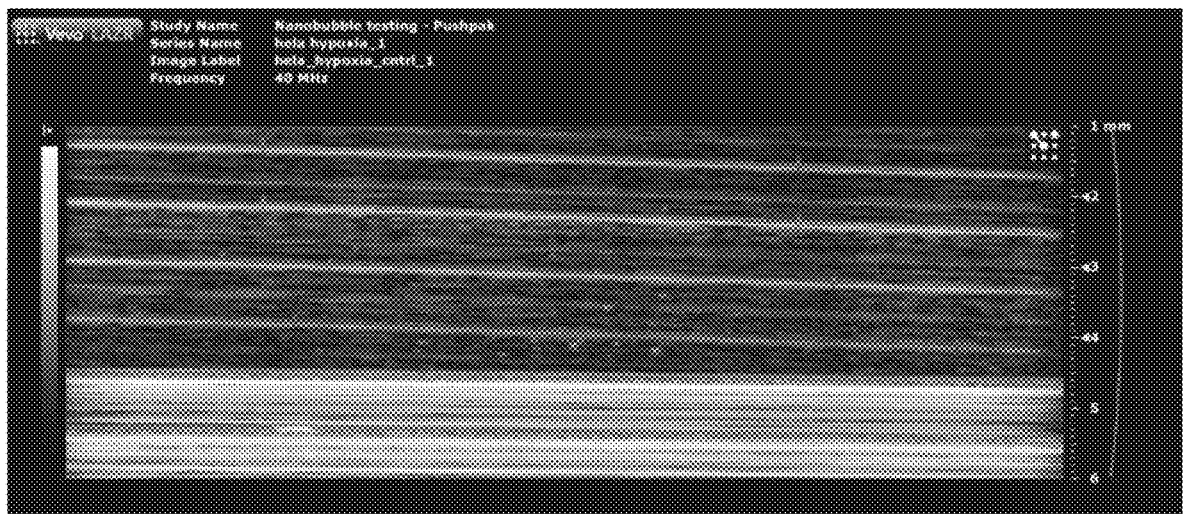
FIG. 17 is an image showing control ultrasound image on agarose base and D.I water. No nanobubbles were added for this image.
Figure 18:
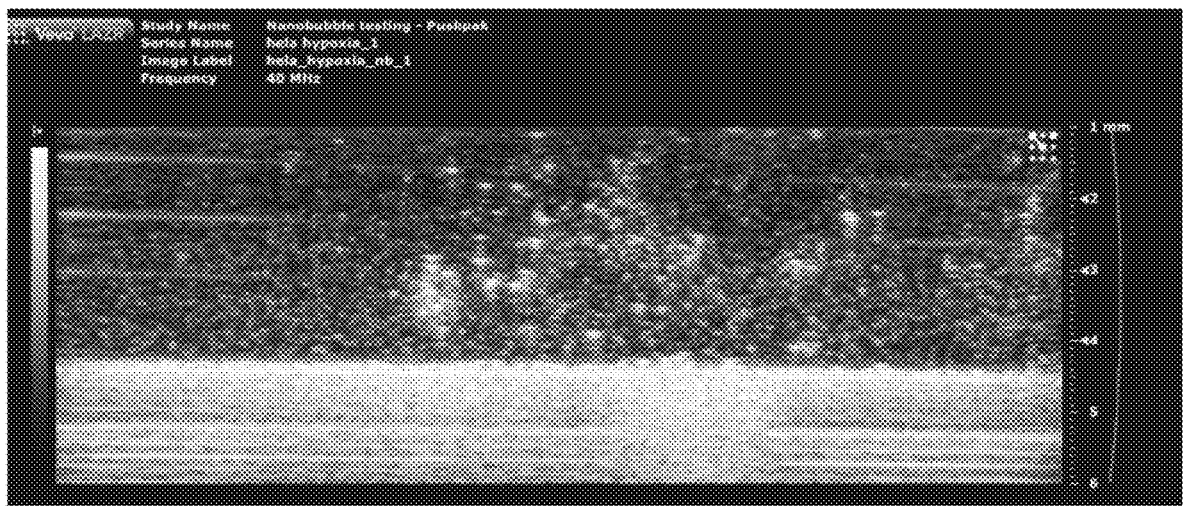
FIG. 18 is an image showing ultrasound image to visualize nanobubbles, wherein the contrast generated is because of the oxygen nanobubbles.

To synthesize the second batch of nanobubbles with drug and fluorophore, docetaxel (0.5 mg/ul in DMSO) and Alexa Fluor 647 (5 ug/mL) is injected into the NaCMC solution prior to crosslinking. Encapsulation of drug inside a contrast-enhancing nanobubble contrary to co-injection of the two is expected to reduce side-effects since it will prevent extravasation of the drug. The surface of the polymer is covalently conjugated with PSMA aptamers (PSMA A10, Integrated DNA Technologies Inc.) for targeting prostate specific membrane antigens (PSMA) which are overexpressed in over 80% of prostate carcinomas. Acidic pH of the nanobubbles before neutralization is expected to assist in conjugation of the aptamers to the nanobubbles. Our preliminary results indicate that aptamer conjugation was successful with ~70% conjugation efficiency determined using a Nanodrop spectrophotometer. The size of the nanobubbles in this example was less than 200 nm as evaluated using transmission electron microscopy (TEM) (FIG. 4 and FIG. 5) and dynamic light scanning (DLS) (FIG. 7). Washing steps were incorporated to ensure pH neutralization and the nanobubble was freeze dried and re-suspended in PBS to achieve the desired concentration.

To optimize the size of the nanobubble to achieve optimum ultrasound contrast intensity, a sequential factorial experiment design and response surface methodology is performed using temperature (0° C. to 37° C.), pH of solution (5 to 9), ultrasound intensity (40 MHz and 70 MHz), and concentration of crosslinker (0.1% to 1%) and NaCMC (0.1% to 2%) as parameters. The synthesis steps to produce oxygen nanobubbles with a range of sizes between about 10 nm and 250 nm that can be excited at specific intensities for imaging and burst release. The nanobubbles act as a contrast agent under low-intensity (40-70 MHz) ultrasound and burst collapse when subjected to resonant high intensity (1.1 MHz focused frequency) ultrasound. Thus, the nanobubbles can first locate a tumor by ultrasound imaging at a low-intensity and then can be selectively burst to release the drug at the tumor site via sonoporation.

Example 2 of Oxygen Nanobubbles as Imaging an Agent

Figure 19:
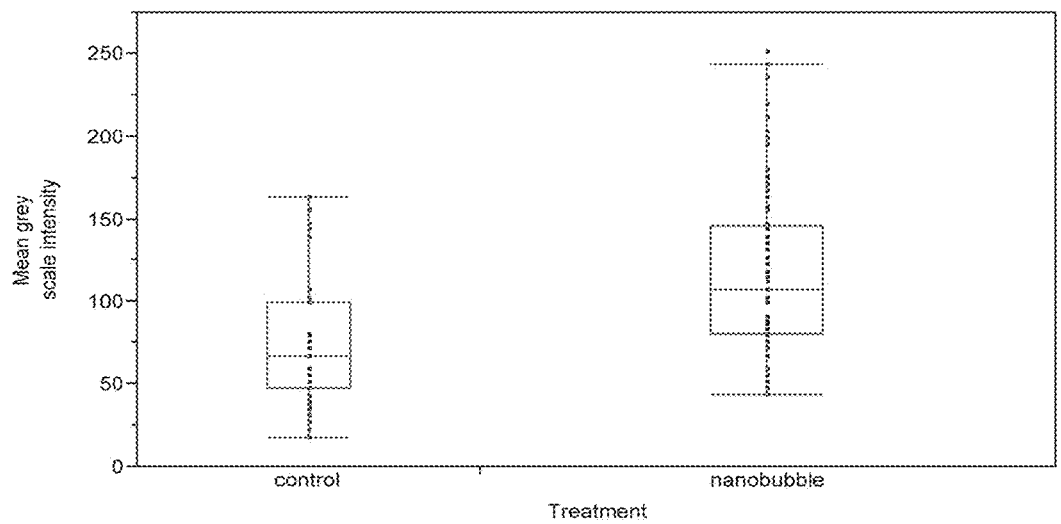
FIG. 19 is a graph depicting a graphical comparison of the mean grey scale intensities of control and nanobubble introduced samples, wherein the significant increase in the mean signal intensity is credited to the contrast generated by the nanobubbles.
Figure 22:
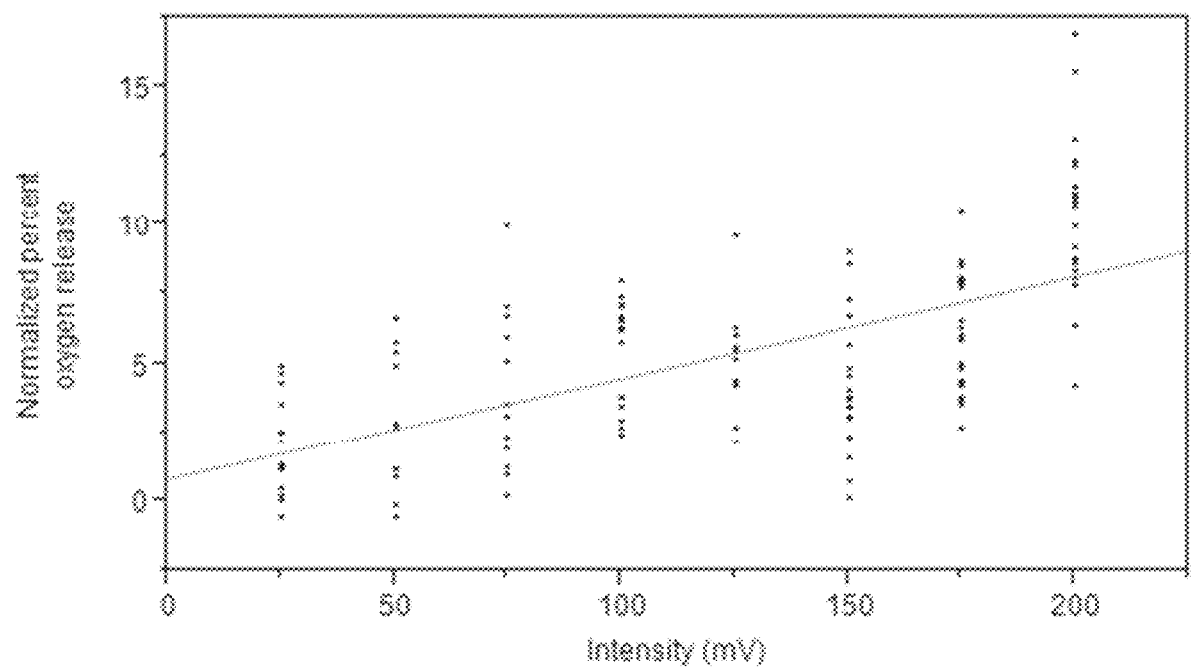
FIG. 22 is a graph depicting normalized percent oxygen release linearly increases upon increase in external ultrasound intensity ($p < 0.0001$), wherein the external ultrasound frequency is set at 1.1 MHz.
Figure 23:
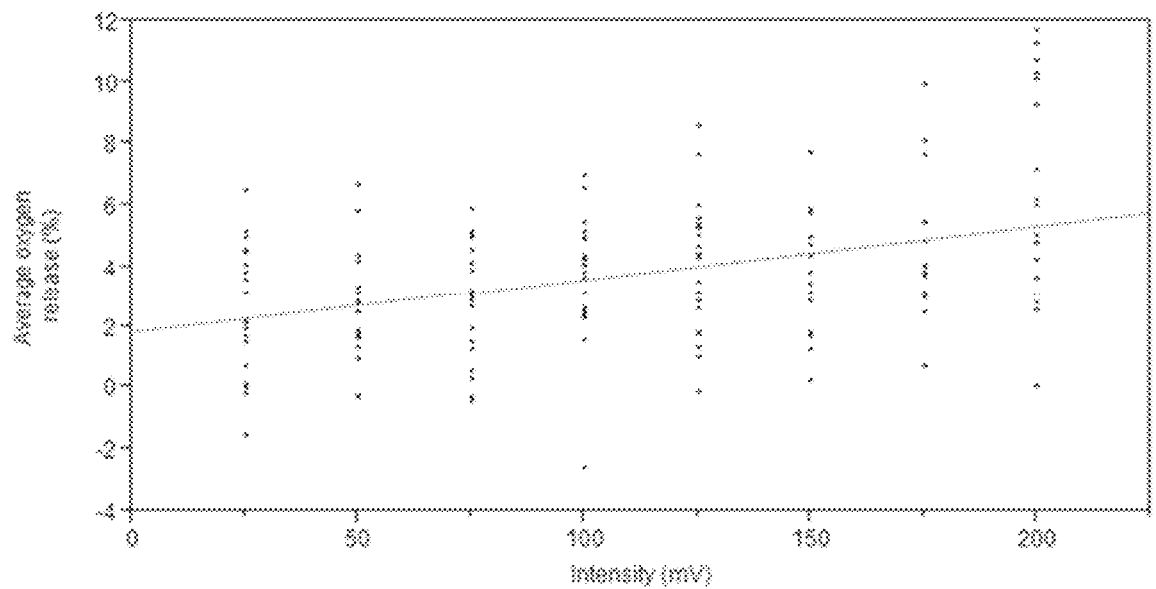
FIG. 23 is a graph depicting normalized percent oxygen release linearly increases upon increase in external ultrasound intensity ($p < 0.0001$), wherein the external ultrasound frequency is set at 2.2 MHz.
Figure 24:
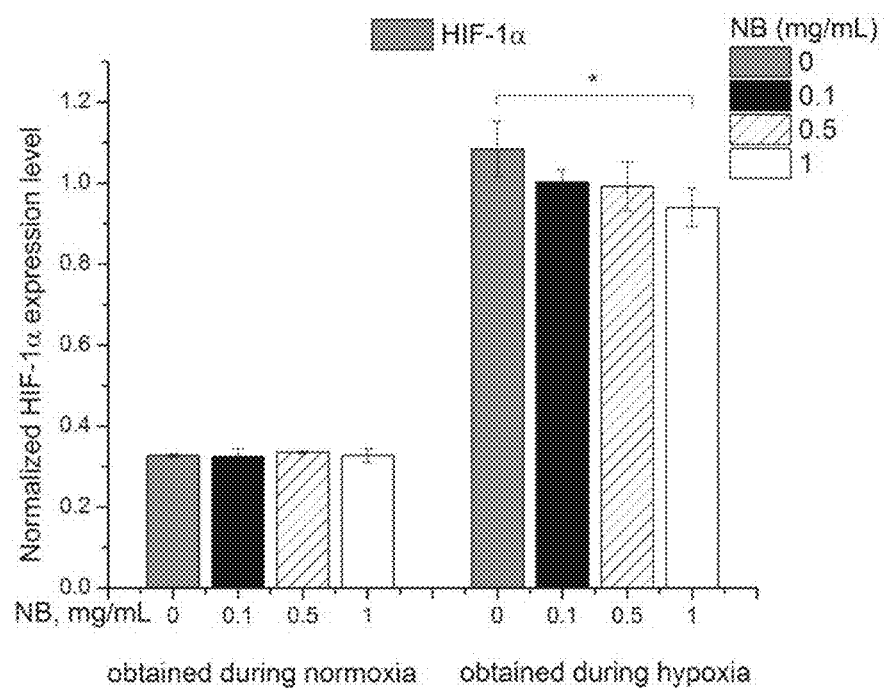
FIG. 24 is a graph denoting HIF-1A protein expression levels obtained for different treatment conditions and nanobubble (NB) concentrations (mg/mL)
Figure 25:
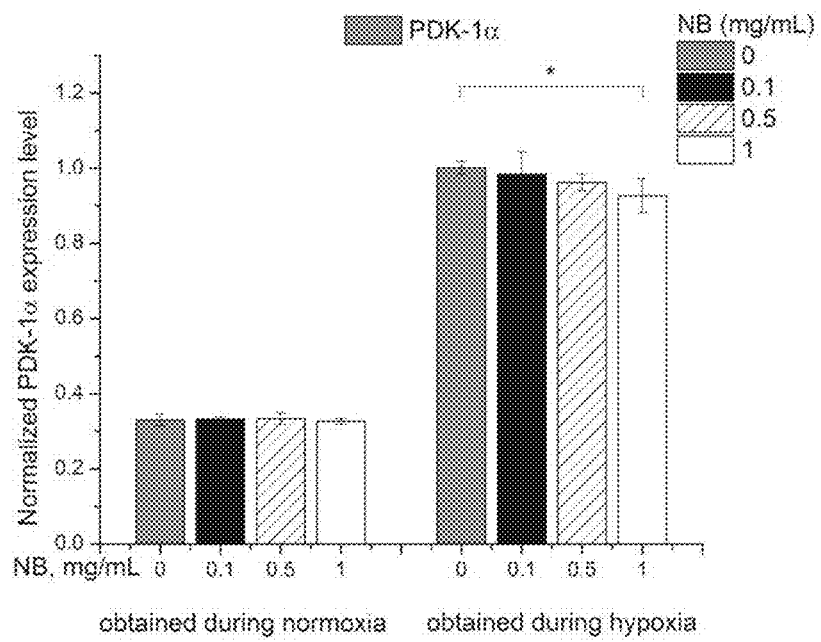
FIG. 25 is a graph denoting PDK1 protein expression levels obtained for different treatment conditions and nanobubble (NB) concentrations (mg/mL).

Ultrasound image of the signal generated from subcutaneous injection of equal volume of nanobubbles and saline. FIG. 19 is a graph displaying averaged mean grey scale intensity within the region of interest corresponding to the injected solutions. Note that there is significant difference between the two images suggesting a strong ultrasound contrast generated in vivo using the nanobubbles.

The approach is to inject the nanobubbles and saline control subcutaneously to nude male BALB/c mice without tumors and observe the ultrasound intensity, velocity, speed and direction of movement, strain rate, volume, and perfusion of the injected nanobubble. Mice are anesthetized and observed using Vevo 2100 ultrasound platform and Kodak whole animal fluorescence imaging system. Results show that nanobubbles have significantly greater ultrasound contrast compared to saline as illustrated in FIG. 9. Further, by using intravenous injections of the nanobubble one can evaluate the circulation and perfusion characteristics of the nanobubble.

The ultrasound trigger platform to burst the nanobubbles is generated by aligning the ultrasound trigger transducer to the subcutaneous injection site. Ultrasound imaging intensity is compared for different transducer frequencies and amplitudes employed and optimal settings are calculated. Finally, oxygen measurements are carried out using an optical sensor (NeoFox, Ocean Optics Inc., FL) and the data is correlated with the ultrasound contrast intensity. After completion of the time frame of observation, the mouse organs are harvested and histopathologically analyzed. Histopathological analysis provides a measure for quantifying nanobubble uptake and also shows cytotoxicity, if any.

Example 3 of Oxygen Nanobubbles Incorporating Oxygen and Using Oxygen as a Treatment Briefly, sodium carboxymethyl cellulose (Ac-Di-Sol, FMC Biopolymer, Philadelphia, PA) was dissolved in nanopure water to form a 0.1% (w/v) gel and homogenized and saturated with oxygen gas (UHP grade). The oxygen inlet was connected with an air nozzle (Nano Super Air Nozzle 1110SS, EXAIR Corporation) and a 20 nm membrane filter (Emflon II, Pall Corporation) to help generate oxygen nanobubbles. Further, the carboxymethyl cellulose solution was sonicated simultaneously with a probe horn (Ultrasonic Power Corporation Cell Disrupter) and a bath sonicator (Branson 2210) since ultrasonic energy helps sonic compression of oxygen microbubbles to produce oxygen nanobubbles in the solution. Fluorescin isothiocynate isomer I fluorophore (5 ug/mL) was injected into the sonicated NaCMC gel to enable fluorescence imaging. Finally, 1% aluminium chloride ($AlCl_3$) cross linking agent was added to form the encapsulation structure under continuous ultrasonication. Aluminium chloride is a trivalent crosslinker and helps decrease the drug release rate compared to bivalent crosslinkers. Aluminium chloride also serves as a strong electrolyte and increases the electrostatic repulsive force to balance out the size reduction forces of the nanobubble, thus stabilizing the nanobubble. The pH of the resulting nanobubble suspension was subsequently neutralized to pH 7 using 0.1% ammonium hydroxide ($NH_4OH$) solution added dropwise.

A new culture of HeLa cells was treated with 1.0 mg/mL of oxygenated nano-bubble (conjugated with Fluorescein isothiocyanate-FitC) solution. After incubation of 24 hours the cells were viewed and imaged under a confocal microscope. Epifluorescence images were obtained with an emission of 488 nm. Olympus IX71® Inverted Microscope with a 20× objective lens (Olympus UIS2) was used to view the cell sample. Images were captured through QCapture software.

Ultrasound imaging was carried out using Vevo 2100 ultrasound imaging system (FujiFilm isualSonics Inc., Toronto CA) equipped with a 22-55 MHz microscan transducer (MS550D, Vevo 2100) operated at 40 MHz. Imaging focal planes, brightness, and contrast were kept constant for all the experiments. Transducer tip was immersed 0.5 cm into the water. To observe the concentration dependence of ultrasound imaging intensity, different concentrations of nanobubbles (Table 1) were injected into 10 mL DI water placed on top of 5 cm 1% agarose gel phantoms. Images were processed using ImageJ (Research Services, National Institute of Health) software. To obtain in vitro ultrasound images, HeLa cells were incubated on 8 $cm^2$ (CLS3294-Sigma Aldrich) culture plates with 10 mL culture media for 24 h with and without nanobubbles.

Further, the culture plates were imaged using the same ultrasound imaging setup with the transducer tip immersed 0.5 mm into the media from above the plate. A region of interest was loaded onto each image and mean grey scale intensity was quantified. The data was exported to JMP software for statistical analysis.

In vitro oxygen measurements were conducted using the NeoFox Phase Measurement system (Ocean Optics). Oxygen flux was measured through the Fiber Optic Oxygen Sensor Probe "-R" (Ocean Optics); and the NeoFox Viewer Software was employed to record the oxygen measurements. The fluorescence based oxygen measurements were conducted in the culture flasks itself. The probe was calibrated using the two-point method with 0% Oxygen (Argon) and 20% Oxygen (Air) as the calibration points. In order to take the measurements, the probe was dipped into the cell culture media present in the experimental culture flasks. Oxygen measurements were recorded for two culture step ups: negative control; and culture treated with 500 uL of 0.5 mg/mL oxygenated nanobubble solution. Both the cell cultures were incubated under hypoxic conditions (hypoxic incubator) for 24 hours.

The nanobubble may be configured to carry therapeutics to a diseased location within a patient. The amount of therapeutic delivered will be an effective amount, which is known to those of skill in the art. The nanobubble configured to carry a therapeutic may be used to treat, inhibit, or reduce the symptoms of solid tumors, blood tumors, circulating tumor cells, bacterial infection, viral infection, inflammation, oxygen-starved environment, autoimmune disorders, diseases of the brain, spine, kidneys, stomach, lungs, eye including glaucoma, optic nerve, gastro-tract, intestines, colon, bladder, ovaries, prostate, lymphatic system, circulatory system, bone, muscle, liver, pancreas, heart, trachea, or inner ear. The therapeutic may be a small molecule, pharmaceutical agent, biomolecule, radiotherapeutic, large molecule, inhibitor, protease, antibiotic, antiviral, a combination product including a biomolecule and synthetic molecule, or siRNA, aptamers, DNA, antibodies, RNA depending on the disease being treated, inhibited, or symptoms reduced. The delivery mechanism of the therapeutic includes but is not limited to injection, inhalation, intravascular, intradermal, catheter, injection into a port, oral delivery, or transmucosal. The nanobubble configured to carry a therapeutic may comprise a continuous polymer outer shell including a targeting agent to direct the nanobubble and its cargo to a specific cell or tissue type. In other embodiments the nanobubble configured to carry a therapeutic comprises a continuous polymer outer shell and no targeting agent.

The nanobubble configured to carry a therapeutic is configured to burst at a specific frequency. The nanobubble may be delivered with a plurality of other nanobubbles which are configured to burst at around the same burst frequency or at different burst frequencies. A combination of burst frequencies is useful if delivering a combination therapy. For example a specific application may require at least two different drugs to be provided to a tissue for the desired effect. The first drug is carried by a first nanobubble configured to burst at a first burst frequency and a second drug is carried by a second nanobubble configured to burst at a second burst frequency. The first burst frequency does not overlap significantly with the second burst frequency which allows for selectively triggering the release of the first drug over the second drug localized near the tissue.

Example 4 Illustrating Therapeutic Delivery to an Animal Model

This example observes the nanobubble characteristics in mice xenografted with LNCaP tumors at multiple timepoints. Briefly, 8-10 week old male nude BALB/c mice (Jackson Labs, stock #002019) were xenografted with LNCaP cells in Matrigel (1:1 volume ratio). The tumor is imaged using the Vevo 2100 ultrasound imaging system every day after xenografting and serves as control for our experiments. 2D and 3D volumetric quantification of the tumors and monitoring of tumor development is repeatedly and longitudinally monitored in the same mouse using the ultrasound machine. One week after tumor inoculation, the nanobubble dose (mg/mg) is injected via the lateral tail vein with the mice under anesthesia. Further, the mice are divided randomly into two groups to evaluate the effect of the external ultrasound pulse trigger in bursting the nanobubbles. Ultrasound bursting pulse (0.1-2 $mW/cm^2$) using the single element transducer at the optimal frequency determined by the in vivo optimization results provides bursting of the nanobubbles and drug release. Tumor size is monitored and it is expected that tumor size will significantly reduce in the mice treated with the external bursting pulse. Burst release of the drug provided a first order drug release and efficient uptake of the nanobubble by the cells because of sonoporation. On the contrary, the mice group without external ultrasound trigger is expected to have a lower decrease in tumor size. Images are analyzed for mean grey scale intensity using ImageJ software. All imaging and analysis is carried out using the same focal planes, focal depth, and region of interest. Oxygen measurements in vivo are performed using optical fluorescence oxygen sensor (NeoFox) and the data is correlated with the ultrasound trigger frequency. Oxygen release data obtained is expected to provide confirmation for effectiveness of targeting of the nanobubble. Pharmacokinetic (PK) and pharmacodynamics (PD) of the drug is evaluated using HPLC/MS. Finally, the mice are euthanized and their organs are harvested for histopathological and fluorescence analysis.

The nanobubble may be configured to act as an imaging agent in vivo. The nanobubble may comprise a continuous outer shell, inner wall of the outer shell, and hollow inner core. The inner core of the nanobubble comprises a contrast agent which may be a liquid or a dye. These liquids are known in the art and some become gaseous at body temperature. Other examples include fluorinated compounds such as perfluorocarbon, perfluorohexane, tetradecafluorohexane or Fluorinert FC-72. The nanobubble may include a targeting agent to direct the nanobubble to a specific cell or tissue type.

The amount of contrast agent included in a nanobubble is dependent upon its size but may range in concentration between about 0 to about $5 \times 10^{-15}$ $cm^3$ concentration. The delivery mechanism of these nanobubbles configured to carry a contrast imaging agent include but are not limited to injection, inhalation, intravascular, intradermal, catheter, injection into a port, oral delivery, or transmucosal.

These nanobubbles configured to carry a contrast agent are configured to specifically not burst below the burst threshold. The burst threshold is set to a frequency higher than is needed to generate an image using an imaging device, specifically ultrasound. This threshold number will change depending on the application and location of the nanobubble comprising contrast agent. Applications of nanobubbles as an imaging agent include imaging a solid tumor, circulating tumor cells, liquid tumors, metastatic tumors, organs including heart, lungs, pancrease, prostate, kidneys, stomach, imaging pancreatic islets, imaging for the identification of a specific protein in a tissue or cell, imaging cholesterol in a tissue or cell, imaging lipids in a tissue or cell, or imaging the uptake of the nanobubble into a specific cell or tissue type for example by endocytosis.

Contrast imaging agent nanobubbles may be used to diagnose or detect where a diseased tissue or cell type is located in the body. The contrast imaging agent nanobubbles may also be used monitor how well a treatment is working by identifying any remaining diseased tissue or cell after treatment has been administered.

The nanobubble may be used for research purposes. Research purposes include imaging epigenetic changes within a cell, including changes to the number of methylated nucleic acids in the cell, and imaging changes to the DNA and histone organization. The nanobubbles may include fluorophores for imaging using an imaging device such as a spectrometer. Drug development assays may incorporate these nanobubbles to monitor changes within the cell given a particular small molecule. These assays include two dimensional (2D) and three dimensional (3D) culture techniques. The nanobubbles may be used to optimize drug delivery for certain agents which need to be protected prior to reaching the specific cell type or tissue type of interest.

Example 5 Illustrating Use of Nanobubbles in Research

The nanobubbles used were prepared as described in example 3. Different experimental set ups were utilized to best study the effects on nanobubble concentrations and treatment time on the target cells. Initial set up included a total treatment time of 48 hours with nanobubbles (0.5 mg/mL) being added at the start of incubation; after 24 hours of incubation; and both at the start and after 24 hours of incubation. A negative control was maintained in both normoxic and hypoxic environment which did not undergo any nanobubble treatment.

An experimental setup to measure the concentration dependence of the oxygenated nanobubble treatment upon the 5mC methylation levels in HeLa cells cultured in hypoxic conditions is described. The experimental set up involved the addition of 500 uL of oxygenated nanobubbles (0.1 mg/mL, 0.5 mg/mL, and 1.0 mg/mL) to the experimental cells cultures. The treatment took place every 8 hours while the cells were incubated in the incubator with hypoxic conditions.

After a total incubation time of 48 hours, the cell cultures were washed with 1×PBS buffer (Gibco by Life Technologies) and detached from the flask with 0.25% 1× Trypsin-EDTA (Gibco by Life Technologies). DNA was extracted from all the samples using the DNeasy Blood and Tissue Kit (Qiagen).

All the experimental as well as the control cell cultures were run in duplicate so as to increase the overall accuracy of the treatment experiments.

All extracted DNA samples were quantified using Nano-Drop ND100 Spectrophotometer. All DNA samples were diluted to 2 ng/μL with DI water. 100 μL of the diluted DNA from each experimental set up was added to individual wells in a 96-well plate with 100 uL of Reacti-Bind DNAcoating solution (Thermo Scientific). The plate was incubated at room temperature for 4 hours on a rocker agitator. After every incubation step, the wells were washed thrice with DI water.

After the first round of incubation and washing, 200 uL of 0.5% (w/v) Casein (Sigma Aldrich) prepared in PBS (10 mM PBS with 150 mM NaCl) was added with each well. Incubation at 37° C. was conducted for an hour. In order to globally tag the 5mC sites, 100 uL of 0.5 ug/mL of the primary mouse monoclonal anti 5-Methyl-cytosine (5-mC) antibody (Epigentek Group Inc., Farmingdale, NY) was added to each well. Incubation was carried at 37° C. for 2 hours. To tag the primary antibody, 100 uL of 1.0 ug/mL of the secondary antibody, goat anti-mouse IgG-Biotin conjugate (Pierce Thermo Fisher Scientific, Waltham, MA) was added to each well. Incubation was carried out at 37° C. for an hour. To form the HRP-streptavidin conjugate, 100 uL of 0.125 ug/mL of Pierce High sensitivity HRP-labelled streptavidin (Pierce Thermo Fisher Scientific, Waltham, MA) was added to each well. Final incubation was conducted at 37° C. The primary and the secondary anti body along with HRP-streptavidin were diluted in PBS (Life Technologies) containing 0.5% (w/v) Casein (Sigma Aldrich) and 0.1% (v/v) Tween 20 (Bio-Rad). In order to generate the color in the assay, each well received a final treatment of 100 uL of Step™ Ultra TMB-ELISA (Pierce Thermo Fisher Scientific, Waltham, MA). After 15 minutes of mild agitation on the rocker, 50 µL of 2M $H_2SO_4$ was added to each well in order to stop the color generating reaction. Spectrophotometer readings were taken at 450 nm using the ELISA endpoint model available on the SoftMax Pro 5.2 software pack. Each assay was performed in triplicate in order to improve the accuracy of the measurements.

Example 6 Illustrating a Use of Nanobubbles in Research

Pancreatic beta cell line MIN6 was cultured using cell culture media consisting of 25 mM glucose, 15% inactivated FBS, 1% penicillin/streptomycin, 2 mM glutamine, 100 µM 2ME, 15 mM HEPES and 5% CO2. Upon reaching confluency of ~80%, cells were trypsinized and encapsulated. For encapsulation, a 1% sodium carboxymethylcellulose solution was prepared. MIN6 cells were centrifuged and resuspended in PBS. Cells were added into the carboxymethylcellulose solution under gentle agitation. 0.1% aluminium chloride solution was added further to complete the encapsulation. Cells were washed in PBS at least 3 times and resuspended in MIN6 media. For scanning electron microscopy (SEM) imaging, cells were fixed in 2.5% glutaraldehyde and freeze dried before imaging.

Another application for the nanobubbles is to measure intraocular pressure in glaucoma. Glaucoma has increased ocular pressure as a primary risk factor. Further, oxygen supply (through a hyperbaric chamber) has been proven to reduce intraocular pressure and has been utilized as a therapy conventionally. There are also several drugs available for reducing any intraocular pressure (IOP). In some embodiments, oxygen comprising nanobubbles may be embedded in a hydrogel which is implanted near the vitreous tumor of an eye or between the conjunctiva and the sclera or at an appropriate position in the eye where oxygen release can provide therapeutic relief or decrease in intraocular pressure. This will aid quantification of intraocular pressure using ultrasound by measuring parameters including or not limited to gray scale imaging intensity, volume of implant, length/dimensions of implant/device. Further, upon bursting the bubbles at a tuned frequency or power or intensity, there will be oxygen and/or drug is released to aid in reducing the symptoms of glaucoma. Thus, the method is minimally invasive, reduces discomfort, and combines diagnosis and quantification of intraocular pressure and glaucoma along with therapy.

Nanobubbles of said invention can be used to enhance ultrasound backscatter. One of the non-limiting examples of an application wherein the ultrasound backscatter signal enhancement can be used is velocimetry of vascular and opaque flows. Velocity vectors can be determined to indicate the flow within the field using particle image velocimetry (PIV) or echo-PIV. The said nanobubbles can also be used to increase the image spatial resolution. The applications of the said nanobubbles are echo-PIV for carotid vascular imaging, blood flow condition monitoring, vortex formation in heart valves, heart diseases, cardiovascular diseases, cardiovascular hemodynamics, and echocardiography.

Images of 200 nm nanobubbles show significant optical scattering using dark field microscopy. These nanobubbles can also be used for signal enhancement in dark field microscopy or hyperspectral microscopy. Nanobubbles can be used to enhance optical scattering imaging and can be used as a tool for theragnostics. The nanobubble brightness, scattering, contrast, and signal enhancement can be tuned by changing the nanobubble properties including but not limited to size, shape, polymer layer thickness, ligands etc. It is also possible to obtain ultra-sharp spectra of the nanobubbles. Simultaneous excitation or nanobubble size specific excitation can be used to trigger the bubbles and obtain bursting of the nanobubbles using external energy source such as lasers, ultrasound etc. The nanobubbles of said invention can also be used for ablation of cells, tissues, or organs using external energy source such as ultrasound, microwave, or lasers. Ablation can be due to collapse of the nanobubble structure and generation of a mechanical pressure wave. The applications of nanobubble cavitation or ablation are, including but not limited to, heart diseases, Alzheimers, brain diseases, cancer, diabetes, removal of arterial clogs etc.

Oxygen nanobubbles have significant potential in targeted imaging and treatment in cancer diagnosis and therapy. Using single ONBs in hyperspectral dark-filed microscope (HSDFM) as a powerful platform, one can reveal the trajectories and quantities of ONBs in cells. The presence of ONBs in the nucleus with respect to an increase in incubation time may provide quantified uptake of ONBs in single cells in ex vivo tumor tissues. These results demonstrate that HSDFM can be a versatile platform to detect and measure cellulosic nanoparticles at the single-cell level and to assess the dynamics and trajectories of this delivery system.

A new intravesical treatment for bladder cancer is provided in this disclosure. Herein we used MB49 murine urothelial carcinoma model to evaluate oxygen encapsulated cellulosic nanobubbles as a novel agent for imaging and ultrasound guided drug delivery. In this study, we demonstrate that oxygen nanobubbles can be propelled and precisely guided in vivo to the tumor by an ultrasound beam. Nanobubble velocity can be controlled by altering the power of the ultrasound Doppler beam, while nanobubble direction can be adjusted to different desired angles by altering the angle of the beam. Precise ultrasound beam steering of oxygen nanobubbles was shown to enhance the efficacy of mitomycin-C, resulting in significantly lower tumor progression rates while using a 50% lower concentration of chemotherapeutic drug. Along with ultrasound contrast agent properties, oxygen nanobubbles possess tumor reoxygenating potential that can reverse hypoxia through targeted delivery of oxygen These results demonstrate the potential of an oxygen nanobubble drug encapsulated system to become a promising novel strategy in targeted drug delivery because of its multimodal (imaging and oxygen delivery) and multifunctional (targeting and hypoxia programming) properties.

Example 7. Oxygen Nanobubble Tracking by Light Scattering in Single Cells and Tissues In this study, we demonstrate the capability of the proposed light scattering method with hyperspectral dark-field imaging microscope for quantitative detection and tracking of ONB in single living cell and identification in tissues. Taking advantage of the ONB's strong light scattering signal due to its non-continuous refractive index, we can effectively identify the relationships between ONB and their size distribution, diffusion coefficients within a single cell, and biodistribution and pharmacokinetic distribution in ex vivo tissue. Our technique can effectively circumvent the common limits that conventional imaging techniques suffer from, to provide a better signal to noise ratio for high-resolution biological imaging with a simple hyperspectral dark-field imaging microscope and image analysis. Our approach demonstrates single nanobubble tracking in the field of nanoparticle localization and targeting in single cells. The proposed contrast agent can be expanded for ex vivo tissue histology and pharmacokinetic/pharmacodynamics studies, in clinical diagnosis and targeted therapy.

In this work, a fast and robust optical spectral imaging approach is demonstrated to quantitatively image and dynamically detect oxygen nanobubbles (ONBs) using HSDFM. ONBs are shown to have a significant effect in halting tumor progression and in altering the cellular dynamics and hypoxia-adaptive processes of the tumor cell. Nanobubbles are an ideal imaging agent in HSDFM due to their intense scattering signal. Combining nanobubbles with HSDFM will provide us with a tremendous opportunity to understand and image dynamic events of nanoprobes and biomolecules, at the single-cell level. Our method was successfully applied to characterize nanobubbles of different sizes and incubation times, within the cellular microenvironment, cytoplasm, as well as the nucleus. Using the established method, quantification of nanobubble distribution and diffusion coefficient within the cell was performed, both, in vitro in live cells, as well as ex vivo in mouse tumor tissues. These results evidently demonstrate our strategy for single nanobubble tracking in biomolecule detection and drug delivery, which is not easily accessible by other methods.

Material and Methods

Preparation of Nanobubbles

Oxygen nanobubbles were synthesized by crosslinking of sodium carboxymethylcellulose with oxygen entrapment. Size distribution of the nanobubbles was optimized using a fractional factorial design of experiments to screen for significant parameters followed by a full factorial design (Table 1) to obtain nanobubbles in the size range 400-800 nm. Briefly, sodium carboxymethylcellulose (Aqualon 7HF PH, Ashland Inc., Calumet City, IL) was dissolved in nanopure water to form a 0.1% (w/v) gel and homogenized and saturated with oxygen gas (UHP grade). The oxygen inlet was connected with an air nozzle (Nano Super Air Nozzle 1110SS, EXAIR Corporation) and a 20 nm membrane filter (Emflon II, Pall Corporation) to help generate ONBs. The carboxymethyl cellulose solution was sonicated simultaneously with a probe (Ultrasonic Power Corporation Cell Disrupter) and a bath sonicator (Branson 2210) for 30-120 sec since ultrasonic energy helps sonic compression of oxygen microbubbles to produce oxygen nanobubbles in the solution. Finally, 0.1-1% aluminum chloride ($AlCl_3$) cross-linking agent was added to form the encapsulation structure under continuous ultrasonication. Aluminum chloride is a trivalent cross linker and helps decrease the drug release rate compared to bivalent cross linkers. Aluminum chloride also serves as a strong electrolyte and increases the electrostatic repulsive force to balance out the size reduction forces of the nanobubble, thus stabilizing the nanobubble. The pH of the resulting nanobubble suspension was subsequently neutralized to a pH of 7 using 0.1-0.5% ammonium hydroxide ($NH_4OH$) solution added drop wise. Finally, the significant parameters were optimized using the prediction profile of the data in JMP (SAS Institute Inc.).

PC3 Cell Culture and Nanobubbles Uptake

Human epithelial prostate cancer cell line, PC3 (ATCC® CRL-1435), was used for in vitro experiments because of its widely studied biochemical profile in response to several chemotherapeutic agents across various experimental conditions. Cells were cultured in RPMI-1640 media (Gibco, Life Technologies) supplemented with 10% Fetal Bovine Serum (Atlanta Biologicals, Flowery Branch, GA) and 1% Penicillin (10,000 I.U./mL)-Streptomycin (10,000 µg/mL) (Mediatech Inc., Manassas, VA). The cells were routinely cultured at 37° C. in a humidified atmosphere with 5% $CO_2$. Cells were tested for mycoplasma contamination using Hoechst 33258 fluorescent indirect staining[30] before initiating the experiments. Briefly, cells were fixed using 4% paraformaldehyde (PFA) solution and stained with Hoechst 33258 fluorescent dye. Images were obtained using the confocal microscope. No small specks were observed surrounding the cells thus confirming the absence of mycoplasma. The cells were incubated with ONBs (0.1 mg/mL) in a 12-well plate and imaged at different time points.

Ex Vivo Quantification of Nanobubbles in MB49 Mouse Bladder Cancer Tissue.

Animals were cared for under the supervision of the Purdue Animal Care and Use Committee (PACUC). Briefly, MB49 cells ($5\times10^5$ cells/mouse) in the media were subcutaneously injected in female 6-8 weeks old C57Bl/6 mice since C57Bl/6 mice are a syngeneic model for MB49 cell line and are immunocompetent. Number of replicates required for the study was calculated using the power law analysis for in vitro and preliminary in vivo data using a desired power of test of 90% and alpha of 5%. After 3 weeks when tumors develop hypoxia and reach an approximate size of 1000 $mm^3$, the mice were randomly divided into two groups of five and six. Tumor-bearing mice were treated by intravenous injections of ONBs (100 µg/mL, 100 µL, n=6) or saline (100 µL, n=5). After dosing, the mice were monitored for weight and implanted tumor size daily. Four days following bolus injections, mice were euthanized via cardiac puncture and the blood and organs were harvested. Harvested tissues and tumors were fixed in formalin-free IHC Zinc Fixative (BD Pharmingen), embedded in paraffin, and sectioned into 5 µm slices. Histology slides were prepared at the Purdue Histology and Phenotyping Laboratory (PHPL).

Hyperspectral Image Acquisition.

HSDFM generates a 3D dataset of spatial and spectral information at each pixel. Hyperspectral data can be obtained by stacking the 1D spectra image along the x-coordinate (slit) by scanning the sample-stage along the y-axis. First, dark-field images were obtained to determine the region of interest (ROI). The detector was uniformly illuminated to acquire a flatfield file to exclude small non-uniformities in gain on a pixel-by-pixel basis for correction. Then pre-measurement was performed with 1D spectral imaging to set the light illumination level, which was optimized to have a maximum signal without saturation, critical for signal normalization. With these preset parameters, 1D spectral image was obtained by projecting the image onto a 10-μm slit, followed by dispersing the slit image with 300 g/mm grating to obtain a high spectral resolution of 0.5 nm. With a line-scanning stage of 40-nm step size, the spectral information of the 2D spatial dimension was collected over the wavelength range from 400 nm to 950 nm. Stabilized mounts guarantee the accurate position information for reconstruction of the images. Hyperspectral images spanning the entire ROI at each wavelength channel can then be constructed from the collected 1D spectral images with a data analysis algorithm.

Simulation of Scattering 3D finite-difference time-domain (FDTD) numerical simulation analysis was used to calculate the far-field angular scattering patterns of ONBs at one specific wavelength (FIG. 27B), and the scattering cross sections of GNPs and ONBs within different incident wavelength (FIG. 27C). To match actual experiment, our model was designed as a 40 nm GNP or a nanobubble sphere (RI=1.515 for shell, RI=1.0 for core) immersed in infinite background material with the RI value of 1.33. Drude model[31] was used to describe the dispersion of gold atoms. A plane wave incident source with linear polarization was applied to calculate the far field angular scattering pattern and scattering cross section. For calculating the far-field angular scattering pattern of ONBs, the frequency was set to 545 THz, the local surface plasmon resonance (LSPR) wavelength of a 40 nm GNP. The scattering cross sections of GNPs and ONBs of size 400 nm were simulated from 330 to 660 THz, corresponding to our experimental illumination source. A fast perfect boundary approximation mesh was used to eliminate staircase error at the interface for accurate simulation. A far-field monitor was used to obtain the 3D radar cross section which subsequently determined the far-field angular scattering pattern. The broadband scattering response was extracted by using a broadband far-field monitor in combination with the broadband far-field template, which allowed the direct extraction of the extinction cross section and scattering cross section. Since the simulation was calculated based on frequency, a "Mix 1D" result template was then used to convert the x-axis from frequency to wavelength domain in the plot.

HSDFM Instrumentation and Imaging Processing.

A home-built HSDFM system was used for imaging cells labeled with AgNPs and AuNPs. The HSDFM platform was installed based on an Olympus BX51 microscope fitted to a vibration-reducing optical breadboard (Thorlabs Inc.). A tungsten halogen source (3900, Illumination technologies Inc.) with highly stable light output (intensity fluctuation <0.1%) was coupled to a CytoViva dark-field condenser (NA 1.2-1.4) via a fiber optic light guide to minimize the thermal fluctuation of light intensity for accurate measurements. Pre-aligned Koehler illumination allowed the tungsten halogen source to focus precisely on the entrance slit of the condenser. Combining the pre-aligned Koehler, critical illumination and structured illumination into the dark-field condenser, high spatial resolution could be obtained. A motorized stepper Prior stage with a minimum step size of 40 nm (H101A, Prior Scientific Inc.) was used to obtain scanning hyperspectral data with high spatial resolution. The scattering light was collected with a 100× oil immersion objective with an iris, and then split into two light paths, one for real-time optical dark-field imaging and the other for hyperspectral measurement. For hyperspectral imaging mode, the scattering signal was passed through a narrow slit and was then dispersed by the gratings into the spectrograph and collected by the thermoelectrically cooled (air) CCD (PIXIS-400BR, Princeton Instruments). The spectrograph (SP2150, Princeton Instruments) includes dual indexable gratings (300 g/mm and 1200 g/mm) and a direct digital grating scanning mechanism with dual-grating imaging and full wavelength scanning capabilities. The fine grating of the spectrograph and the very low dark current of the CCD (0.03 at −75° C.) contributes to the high spectral resolution and SNR of the hyperspectral image.

In order to obtain spectrum of the nanobubbles at a specific location with high SNR, intensity and wavelength filters were needed for the removal of background noise, as well as noise from dust, glassware defects, and non-specific aggregates of nanoprobes. Acquiring spectrum from specific location comprises two main steps: (i) reconstruct hyperspectral image at specific wavelength with signal normalization and setting of spectral filter and intensity threshold; and (ii) locate the position in the reconstructed image and extract the spectrum from hyperspectral data. Since the intensity from the incident source was not constant over the whole range of wavelengths, the obtained signals should be normalized to a proper reference spectrum to extract the true scattering spectra. For in vitro and in vivo nanobubbles, the reference background was different: The in vitro nanobubble signal was normalized to the spectrum of halogen source, while the in vivo nanobubble signal was normalized to the spectrum of the cellular background. Ten representative scattering spectra from cellular compartments were averaged to facilitate signal normalization and intensity filtering. Scattering from the defects of optical glassware and dusts can also be filtered out by setting appropriate intensity thresholds and spectral filters. For image reconstruction, with the preset wavelength range and intensity threshold, the collected 1D spectral data was stacked and a 2D image at the desired wavelength channel was generated. From this image, the spatial distribution and quantity of can be determined. Based on the hyperspectral data set, spectrum of scattering at each pixel can be extracted.

Algorithm for Quantification and Diffusion Coefficient

The quantification and diffusion coefficient of nanobubbles in live cell was analyzed from trajectories and mean squared displacement. The quantification of nanobubbles in one cell can be derived from movement of nanobubbles in live cells. Generating trajectories of each nanobubble comprises two main steps: (i) Identifying each nanobubble; (ii) Linking all these points in each frame into trajectories. Approximate radius of the nanobubbles was set for image restoration and refinement of the point locations to identify each nanobubble. Intensity percentile and cut-off intensity threshold were acquired to determine which bright spots are accepted as nanobubble. After identifying each nanobubble in every frame, the nanobubble positions be connected to a trajectory. The diffusion coefficient is calculated with regression method based on trajectories. For 2D dimensions, the mean squared displacement $<d^2>$ of nanobubble for different time lags ($\tau_j = j\Delta t$) can be expressed as:

$$<d^2>_j = 4D\tau_j \quad (1)$$

The diffusion coefficient is calculated by the slope of a regression line fitting a specific number of data points.

Algorithm for Quantification of NB in Tissue

Figures 30A, 30B, 30C, 30D:
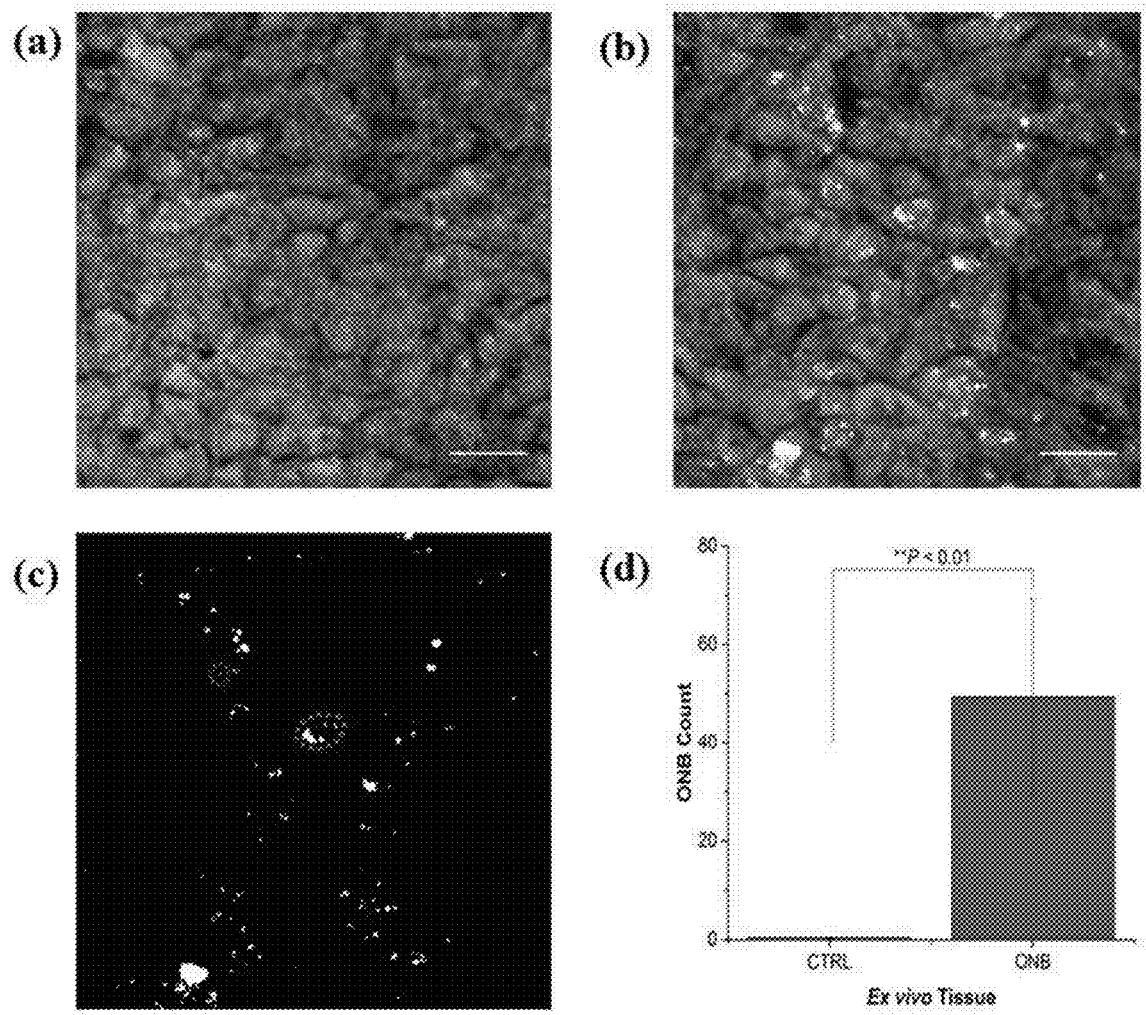
(FIG. 30A) Representative dark-field optical image of MB49 mouse bladder cancer tissue treated with saline (control) (FIG. 30B) Representative dark-field optical images of Mb49 mouse bladder cancer tissue with ONBs. Single ONB used as reference was circled with red dotted lines, while cell was circled with ellipse red dotted line (FIG. 30C) Representative grey scale image of ONBs with intensity threshold filter processing.
(FIG. 30D) Number of ONBs in single cell in ex vivo tissues treated with saline (CTRL) or nanobubbles (ONB) (N=9, P<0.01).

Hyperspectral data analysis was used to decide nanobubbles and their location. According to the calculated results (FIGS. 33A, 33B and 33C), the scattering cross section is same with different gap distance between two nanobubbles, which means no nonlinear coupling was generated from nanobubbles aggregates. Hence, the ratio between the sum of intensity from some specific area and single nanobubble can be exploited to derive the number of nanobubbles in this specific area. This algorithm needs to set the intensity of pixels that has no nanobubble as zero to determine the precision of the method. Due to stronger scattering from nanobubbles than that from Mb49 mouse bladder cancer tissue organelles (FIG. 30B), intensity threshold was used to filter the scattering intensity from tissue. In images, pixels with intensity lower than intensity threshold were set to zero for generating an accurately quantitative algorithm (FIG. 30C). The intensity from one nanobubble was established from the analysis of intensity from all the pixels that have nanobubbles. Based on random distribution, it is reasonable to set the weakest intensity of some area as the intensity of one nanobubble, as shown in FIG. 5c. The number of nanobubble from one cell in tissue can be obtained with this intensity from one nanobubble as reference (FIG. 30D).

Nanobubble Synthesis and Optimization

A full factorial design (Table 1) was used to optimize the nanobubble size using sodium carboxymethylcellulose concentration (CMC concentration), aluminum chloride concentration (Crosslinker concentration), and ultrasound homogenizer power (ultrasound power) as the three optimization variables (Table 1). We found that CMC concentration was highly significant ($P<0.05$) and crosslinker concentration was weakly significant ($P<0.1$) in explaining nanobubble size. Ultrasound power was not significant in influencing the size of nanobubbles. The interactions of none of the parameters were significant. Further, using the prediction profiler (FIG. 34), 400 nm nanobubbles were obtained using "low" concentrations of crosslinker and CMC whereas 800 nm nanobubbles were obtained using "high" concentrations of both, crosslinker and CMC.

FIG. 31 illustrates dark-field optical images of nanobubble of different size (FIGS. 31A-B) and PC3 cell without nanobubble (FIG. 31C) and spectra of nanobubbles and cell organelle in PC3 cell were extracted from hyperspectral data (FIG. 31D)

FIG. 32 illustrates the simulated far-field scattering with CST studio suite 2014 software. (FIG. 32A) Far-field scattering cross section of nanobubble dimer with different gap distance. (FIG. 33A) Electronic field intensity distribution with difference gap distance at 545 THz. A plane wave incident source with linear polarization in the range of 330 to 660 THz was used for calculation FIG. 33 illustrates dark-field optical images of 40 nm AuNp (FIG. 33A) and 400 nm oxygen nanobubble (FIG. 33B) in vitro. ONBs have a significantly higher signal to noise (SNR) ratio compared to AuNp (FIG. 33C)

FIG. 34 is a prediction profile for the optimization of nanobubble size. Crosslinker and CMC concentration were significant in influencing the size of nanobubbles;

DLS size distribution for 400 nm nanobubbles is shown in FIG. 35 and for 800 nm nanobubbles is shown in FIG. 36. Therapeutic potential of ONB for PC3 cell line with 24 h incubation time is shown in FIG. 37; Therapeutic potential of ONB for PC3 cell line with 48 h incubation time is shown in FIG. 38.

FIG. 39 illustrates 400 nm nanobubble quantification using dark-field imaging for in vitro assays. FIG. 40 illustrates 800 nm nanobubble quantification using dark-field imaging for in vitro assays (PDF).

Optical Scattering from Nanobubbles

Figures 26, 26A, 26B, 26C, 26D, 26E, 26F, 26G:
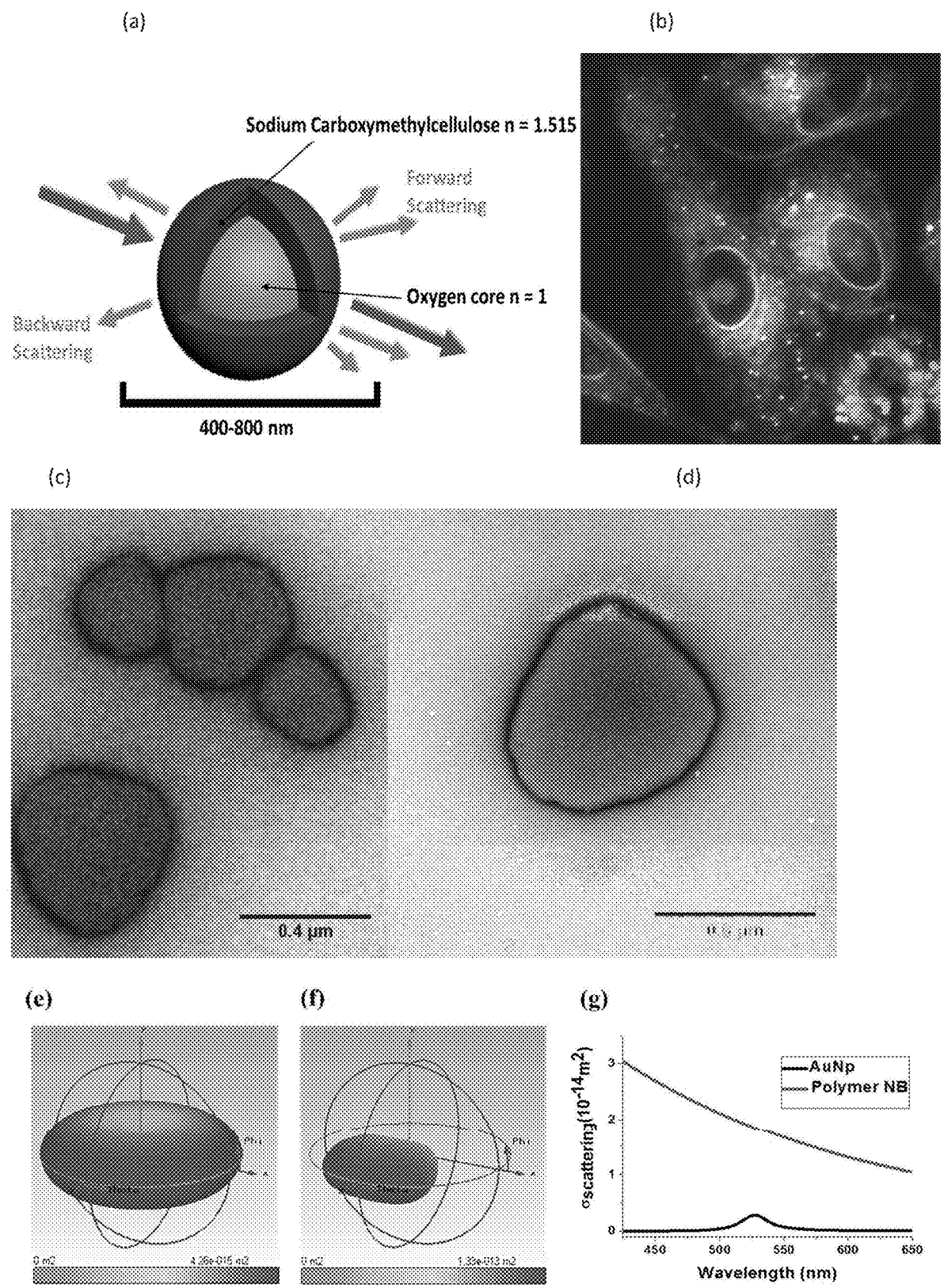
FIG. 26 Illustration of quantitative detection of ONBs in cells with high signal to noise ratio and simulation results of far-field scattering.
(FIG. 26A) Schematic illustrating the principle of dark field imaging using ONBs for optical contrast enhancement. Refractive index of different components is provided.
(FIG. 26B) Dark-field optical image of 400 nm ONBs in PC3 cells. Transmission electron microscopy images showing 400 nm (FIG. 26C) and 800 nm (FIG. 26D) ONBs.
(FIG. 26E) Angular scattering pattern of 40 nm AuNp in PBS.
(FIG. 26F) Angular scattering pattern of 400 nm nanobubble in PBS.
(FIG. 26G) Far-field scattering cross section of AuNp and nanobubble with different wavelengths. A plane wave incident source with linear polarization in the range of 330 to 660 THz was used in calculations.

The synthesized ONBs consist of a gaseous molecular oxygen core surrounded by a cellulosic polymer shell (FIG. 26A). This core-shell structure of the nanobubble causes non-uniformity of refractive index that is expected to force light to deviate from its linear trajectory to generate light scattering. The intensity and angular distribution of light scattering has a strong relation with the localized non-uniformities.[9] For scattering imaging, it is necessary to design nanomaterials with large non-uniformities in the refractive index range to obtain a high scattering signal from the probes to ensure a high signal to noise ratio. As depicted in FIGS. 26A-26B, the refractive index of gas filled in an ONB is 1.0, while the refractive index of shell made of sodium carboxymethylcellulose is 1.515, and that of background medium is 1.3345 (phosphate buffered saline). ONB with a large difference in refractive index between the shell and the core was designed for this study to enable quantitative detection and tracking with single particle resolution. Two different sizes of nanobubbles i.e. 400 nm and 800 nm were synthesized using factorial design of experiments (Table 1) and optimized using response surface design FIGS. 26C-26D show transmission electron microscopy (TEM) images of ONBs with a size of 400 nm and 800 nm respectively. The nanobubble shell was approximately 20 nm in thickness whereas the gaseous core was approximately 350 nm in diameter. We found that the nanobubbles of both sizes were monodisperse (Z average of 325.8 d-nm and 787.8 d-nm for 400 and 800 nm nanobubbles respectively) and the polydispersity index was 0.374 for 400 nm and 0.632 for the 800 nm nanobubbles respectively (FIG. 35, 36). No multimodal peaks were obtained in either 400 nm or 800 nm nanobubbles and the cumulants fit error was less than 0.001 for both samples, indicating that the samples were monodisperse. The delivery of ONBs into the cell is expected to produce a large light scattering signal due to the large refractive index difference of ONB (FIG. 26B) for molecular reporting. Further, theoretical calculations of far field angular scattering pattern and scattering cross section were also performed to illustrate the mechanics of ONB scattering. Furthermore, ONBs radiate light out in all directions in the XZ plane (FIG. 26F), whereas gold nanoparticles (FIG. 26E) radiate light in a localized angular range. The narrower scattering angle of ONBs helps concentrate the scattering intensity within a confined space. The directional scattering of ONBs will help increase the collected signal intensity by the microscope objective. FIG. 26G shows that the scattering cross section of ONB is much larger than that of a gold nanoparticle.

Single Nanobubble Tracking and Quantification in Cancer Cell Lines

The number of ONBs and individual nanobubble tracking were determined using the scattering spectral signature with HSDFM. First, in vitro single ONB tracking was performed to evaluate the tracking efficiency. As illustrated in FIG. 27, the trajectories of each ONB were obtained by linking ONB positions in the image stacks for each frame of time. The spectra obtained from the cellular organelles and nanobubbles were used to further distinguish the two materials. We found that the spectras of 400 nm nanobubbles are reproducible with minor differences in peak positions and spectral width (FIG. 27B). The diffusion coefficient of ONB in PBS buffer was found to be 0.75 $\mu m^2/s$ (FIG. 27C) derived using regression analysis based on trajectories. This set of in vitro characterization of ONBs demonstrates the optical validity of our method for the detection of specific nanobubbles in cells and tissues.

Estimation of the diffusion coefficient is very important for studying the dynamics of ONBs as a drug carrier in cells and to understand the mechanism of drug delivery. The size of ONB is a crucial factor in determining its interaction with cells and distribution in the biological system. The ability of nanoparticles to extravasate from the vasculature and also their clearance from circulation depends on their size. This is an important consideration for ONB drug carriers since longer circulating ONBs will have a higher chance of reaching their target, resulting in improved treatment outcome. Our first set of experiment was thus performed to evaluate the number and diffusion coefficient of ONBs with different size in single cells. PC3 human prostate cancer cell lines were incubated with 400 nm and 800 nm ONBs for 2 hours. Dark-field optical images sequences were obtained with 100 ms frame interval. Since cellular organelles were stationary compared to ONBs, the bubbles were located in the cells by tracking their movement in each frame, as shown in FIG. 28. Cellular uptake efficiency was calculated using NanoTrackJ plugin[16] in ImageJ software. The number of nanobubbles per cell were counted using the plugin with the mean filter and tolerance levels adjusted to be the same for all the images. We found that the cellular uptake efficiency for 400 nm ONBs was ~88% higher than the 800 nm nanobubbles ($P<0.01$). Further, the intranuclear uptake efficiency was ~56% higher for the 400 nm nanobubbles compared to the 800 nm nanobubbles ($P<0.01$) possibly due to enhanced uptake of the smaller sized nanoparticles via endocytosis compared to fluid-phase pericytosis of larger sized nanoparticles. Literature supports our findings in that the efficiency of nanoparticle uptake is indirectly proportional to the size of the nanoparticle.

Further, we calculated the diffusion coefficients of ONBs based on trajectory tracking, linear fitting of mean square displacement, and 2D mean square displacement equation. The linear model was found to be an appropriate fit for the data obtained ($R^2>92\%$). It was observed that as the size of ONB increases, the diffusion coefficient decreases (FIG. 28). Diffusion coefficient can be expressed as $$D=(1/f)*k*T \tag{1}$$

where f is the frictional coefficient, k is Boltzmann constant, and T is the absolute temperature. Frictional coefficient has a direct relation with viscosity and diameter of nanobubble.[21] When the size of ONB increases, the frictional coefficient increases due to larger surface area of the ONB, and this results in an increase in the diffusion coefficient. These results support the identification and tracking capability of our optical scattering method.

Figure 29:
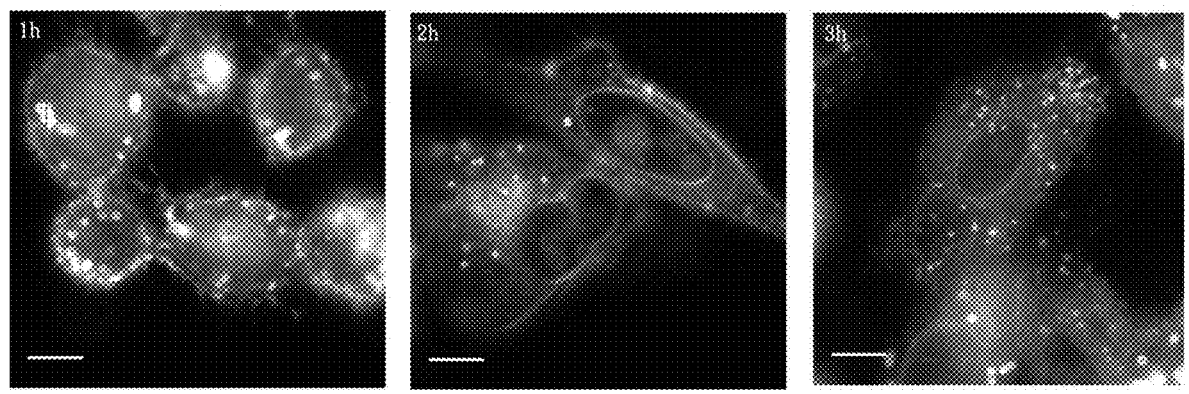
FIG. 29 Dark field optical images of PC3 cells incubated with 400 nm ONBs with different incubation time. Nucleus highlighted using red dotted line. ONB uptake into the nucleus increases over the time period evaluated (3 h). Scale bar=5 µm.

Efficient delivery of drug loaded nanoparticles to the nucleus of tumor cells is critical for enhancing the efficacy of targeted drug delivery. The ONB is expected to significantly enhance drug delivery to the nucleus of the cells due to its size. To study the cellular and nuclear uptake efficiency of ONBs, we performed in vitro experiments using prostate cancer cells (PC3) with 400 nm ONBs and different incubation time. As shown in FIG. 29, no ONBs were observed inside the cells after 1 hour of incubation. As the incubation time increased to 2 hours, some ONBs were observed in the cytoplasm of the cells due to endocytosis. However, no ONBs were observed in the nucleus after 2 hours. Further, ONBs gradually penetrated the nuclear membrane, and entered the nucleus as incubation time increased to 3 hours. Our results indicate that the light scattering approach using dark field microscopy to characterize the biophysical properties of ONBs s is a promising approach for use as both, an optical imaging agent as well as a drug delivery enhancer.

Single Nanobubble Quantification in Bladder Tumor Tissue

We further studied the potential of ONBs and HSDFM for ex vivo quantitative analysis of biodistribution in different tissues. In vitro, the diffusion of ONBs within the cell and its environment can be utilized to distinguish them from static intracellular organelles. However, for ex vivo analysis of ONBs in paraffin embedded or cryosectioned tissue samples, hyperspectral information analysis was used to distinguish ONBs from static cellular organelles instead of movement analysis since the motion of ONBs is hindered in the paraffin embedded slides. According to Mie scattering, some intracellular organelles with size on the same order of the wavelength of incident light have large scattering, and the scattering color is white due to the broad spectrum. The scattering color of ONBs was found to be white, making it difficult to differentiate ONBs from intracellular organelles with dark-field optical images (FIG. 32). Nevertheless, the spectrum information was utilized to distinguish ONBs from the intracellular organelles. Different sized ONBs have unique scattering spectrums; the spectrum 'red shifts' as the nanoparticle size increases. As illustrated in FIG. 32, experiments in this study were performed with 400 nm ONBs, which have a different spectrum than the cell organelles in the cytoplasm.

To validate our technique ex vivo, MB49 mouse bladder cancer cell line was implanted subcutaneously into mice and treated with ONBs (see methods). The tumors were excised in formalin, embedded in paraffin, and sectioned at a thickness of 10 μm. Negative control experiments were also performed to prove the specificity of the ONB. From FIGS. 30A-30B, it is evident that ONBs have a strong scattering signal, and results in optical dark-field images with high signal to noise ratio. Using intensity threshold filter, gray scale images of ONBs were obtained (FIG. 30C). After excluding the background noise with intensity threshold, improved quantification information can be obtained. Further, we quantified the number of nanobubbles in ex vivo mouse tumor tissue treated with either saline (CTRL) or ONB (FIG. 30D) using MTrackJ plugin in ImageJ. We found that ONBs could be accurately detected using our technique in ex vivo tumor tissues.

Our experiments point to the key advantages of high-resolution imaging and tracking of ONBs using HSDFM. The major advantage of our technique is the strong signal from single ONB due to the large light scattering cross-section, which makes the quantification and tracking of ONB with high SNR at the single-cell level possible. As evident from FIG. 34, the SNR of ONB is much higher than that of gold nanoparticle, which has been extensively utilized as imaging nanoprobes due to their strong localized surface plasmon resonance scattering cross-section. Owing to the dipole resonance from the interaction with incident photons, the large scattering cross-section of plasmonic NPs can generate a ten- to million-fold stronger signal than conventional fluorophores. Nevertheless, compared to gold nanoparticles with size of 40 nm, ONBs have larger light scattering, as demonstrated in our in vitro results (FIG. 34).

Our work demonstrates the feasibility of HSDFM for tracking and visualization of ONBs in single cells based on light scattering. By fabricating the ONBs to have a high refractive index difference between core and shell, the scattering cross section can be significantly enhanced, which constitutes the scientific base of our strategy. We applied this method to analyze the relation between the size of ONB and its diffusion characteristics, quantification of ONBs in single cell, and uptake of ONB by cells with time and to assess its distribution in the cell cytoplasm and nucleus. The methods developed can be utilized to count ONBs in ex vivo bladder tumor tissue. Our technique is broad and can be applied to a range of systems to track drug-loaded ONB's in tissue cultures, assess its endocytosis mechanisms and distribution ex vivo in various tissues. Further, the dynamics and kinetics of cellular uptake and the role of the cytoskeleton, in vitro and ex vivo can be effectively studied using the developed tools. Finally, fundamental molecular mechanisms in living cells can also be revealed by utilizing the power of HSDFM and ONBs.

Example 8. Ultrasound Beam Steering of Oxygen Nanobubbles for Enhanced Bladder Cancer Therapy In this study we have shown oxygen loaded nanobubbles have the potential to act as ultrasound guided and powered drug delivery systems for reverting hypoxia in non-muscle invasive bladder cancer (NMIBC) tumors. Similarly, other chemotherapeutic-targeting drug delivery systems to treat hypoxic tumors could be developed using ONBs. We have demonstrated image guided steering (~100 µm resolution) of particles, and a Doppler ultrasound beam was utilized to steer and guide nanoscale oxygen bubbles to a desired location both in vitro and in vivo using ultrasound image guidance. The ability to precisely steer nanobubbles loaded with a payload using non-invasive and safe image-guided ultrasound offers considerable promise for designing precise cargo delivery and hypoxia reprogramming for a wide range of biomedical applications.

Materials and Methods

Cell Culture

The mouse urothelial carcinoma cell line MB49 was used for in vitro and in vivo experiments because it is a widely used and well-studied mouse bladder cancer model. Cells were cultured in DMEM/F-12 media with addition of 10% Fetal Bovine Serum and 1% Penicillin (10,000 I.U/ml)-Streptomycin (10,000 µg/ml). The cells were cultured at 37° C. in a humidified atmosphere with 5% $CO_2$. Cells were tested for mycoplasma contamination using Hoechst 33258 fluorescent indirect staining[44] before initiating the experiments. Briefly, cells were fixed using 4% paraformaldehyde (PFA) solution and stained with Hoechst 33258 fluorescent dye. Images were obtained using a confocal microscope. No small specks were observed surrounding the cells thus confirming the absence of mycoplasma.

Intravesical Tumor Instillation

All experiments were performed per our protocol approved by Purdue Animal Care and Use (PACUC) committee (approval #1404001052). Study was performed with blinding for all researchers collecting data except the first author PB for whom blinding was not possible. Female C57BL/6 mice were anesthetized by 1-2% isoflurane gas inhalation at 2 L/min. Electrocauterization technique was used to create a minor injury on the wall of the bladder for MB49 cells to adhere to. A 24 gauge Teflon catheter (Terumo Surflo PTFE I.V. Catheters, Fisher Scientific) was inserted into the bladder through the urethra. Minor pressure was applied onto the bladder area to release the urine from the bladder. A wire, connected to the electrocautery unit was then instilled into the bladder through the catheter. $1 \times 10^4$ MB49 cells were then instilled into the bladder; dwelling time was approximately 20 minutes to allow the cells to adhere to the injured bladder wall.

Synthesis of Oxygen Nanobubbles and Mitomycin Encapsulation

ONBs were synthesized by modifying our previously published protocol.[28] Briefly, sodium carboxymethyl cellulose (NaCMC) hydrogel (FMC Biopolymer) an FDA-approved excipient was cross-linked while encapsulating the oxygen inside the gel using a layer-by-layer (LBL) approach. NaCMC (Ac-Di-Sol, FMC Biopolymer, Philadelphia, PA) was dissolved in nanopure water to form a 0.1% (w/v) gel and homogenized and saturated with gaseous oxygen (UHP grade) with a nanosize air nozzle (EXAIR Corporation) and a 20 nm filter (Emflon II, Pall Corporation) to help generate oxygen NBs. After sonication,[46] 1% aluminum chloride ($AlCl_3$), a trivalent cross-linking agent which provides exquisite stability, was added to form the encapsulation under continuous ultrasonication and adjusted to a neutral pH, washed, freeze-dried and re-suspended in PBS for further use. To synthesize ONB-MMC, required amounts of mitomycin-C (LKT Laboratories) was dissolved in nanopure water before beginning the ONB synthesis process. The concentration and encapsulation of MMC was measured using LC-MS/MS.

Cell Count and Cell Viability

Cell count and cell viability measurements were performed before and after the experimental procedure for initiation and completion respectively. To approximate the number of live and dead cells in the sample the Countess® Automated cell counter (Invitrogen, Life Technologies) was used. The original sample dilution was carried out in 0.4% trypan blue (Sigma Aldrich) and further diluted by a factor of 2. The prepared samples were deposited onto the punter slides and were used for cell counting.

In Vivo Ultrasound Imaging and Beam Steering

Vevo 2100 ultrasound imaging system (Fujifilm VisualSonics Inc., Toronto CA) equipped with a 22-55 MHz microscan transducer (MS550D, Vevo2100, VisualSonics Inc.) with a center frequency of 40 MHz. Imaging focal zones, brightness, and contrast were kept constant throughout the experiments. Mice were anesthetized using 1-2% isoflurane in 2 L/min of medical air and restrained on a heated platform. B-mode and 3D image were collected every other day for each mouse.

After the bubbles were injected intravesically, a pulsed wave Doppler beam was applied for five minutes and B-mode images were recorded. 100% percent power was consistently used, since it was shown to result in the highest average nanobubble velocity.

ONB-MMC and MMC Treatment Regimens

Mice were randomized into three groups: ONB-MMC (Mitomycin-C encapsulated in the oxygen nanobubble), MMC only, and saline (CTRL) (N=8). The mice were imaged 48 hours after the instillation of the tumors and treatment was administered every other day based on previously established protocols. ONB-MMC, MMC only, and saline (CTRL) group mice then received 100 µL injections with optimized concentrations, every other day.

Tumor Volume Analysis 3D images of bladder tumor were taken every other day using the Vevo 2100 ultrasound imaging system (Fujifilm VisualSonics Inc., Toronto CA). Vevo Lab software was used to manually segment given 3D images in 2D slices, with step sizes that can be as small as 10 µm. Segmentation of a 3D image allowed accurate volume measurements to be taken from each 3D image. Manual segmentation was used to outline the tumor for each 2D image segment, which were then lofted together to reconstruct the tumor and estimate its volume.

Oxygen Release Measurement

Oxygen content in the mouse bladder was measured using OxyLite oxygen probe (Oxford Optronix Ltd). The SUR-FLO® ETFE I.V. 24 Gauge Teflon Catheter was instilled into the bladder and slight pressure was applied on the bladder to release the urine. Oxygen probe was then instilled into the bladder through the catheter and 10 measurements of oxygen partial pressure were recorded.

Histology Analysis

Histology slides were prepared and immunohistochemistry was performed at Immunohistochemistry Laboratory at IU Health Pathology. Harvested organ tissue and bladder tumors were fixed in formalin-free IHC Zinc Fixative, embedded in paraffin, and sectioned into 5 µm slices. HIF-1 and VEGF immunohistochemistry was performed using buffered zinc formalin fixed tumor section. Blocking, antigen retrieval, and primary and secondary antibody staining were performed simultaneously. The tissue sections were imaged using Leica DMi1 inverted microscope, and image processing was performed using ImageJ software (Research Services, National Institute of Health). Each tissue section was imaged under ×20 and ×40 magnification, composite images were converted to RGB stacks and integrated density of staining was calculated.

Cryosectioning

Mouse bladders were cryosectioned prior to dark-field imaging using a published protocol. First, the mouse bladder was dissected immediately after euthanizing the mouse. The entire bladder was frozen in a cryomold cassette (Fisher Scientific, NC9969692) with OCT compound (Fisher Scientific, 23-730-571). The bladder orientation was maintained by staining the bladder with tissue ink (Davidson Marking System, Bradley Products, #1101). Further, bladder tissue sections of 10 µm thickness were cut using a cryotome (Cryotome FE, ThermoFisher Sci.) with a spacing of 100 µm between every section. The tissue sections were imaged using dark-field microscopy.

Dark-Field Microscopy

Dark-field imaging of the cryosectioned tissues were performed using a previously published protocol. Briefly, a home-built hyperspectral dark-field microscope (HSDFM) was used for imaging the tissue sections. The samples were illuminated using a tungsten halogen source (3900, Illumination technologies Inc.) and a CytoViva dark-field condenser (NA 1.2-1.4) with a fiber optic light guide. The scattering light was collected with either a 10× or 100× oil immersion objective. The tissue orientation was maintained by observing the samples first at low magnification ×10 and identifying the tissue ink on the bladder wall. Once the tumor was located, the ×100 magnification was used to obtain hyperspectral images.

Quantification of ONB in HSDFM Images

The ONBs in the HSDFM images were quantified with ImageJ software (NIH) per our previously published protocol.[28] The maxima function on ImageJ was used to obtain the raw integrated density of ONBs per area. The baseline was obtained by quantifying the signal in mouse tissue treated with saline (CTRL).

Statistical Data Analysis

Statistical data analysis was performed using JMP Statistical Software (SAS Institute Inc., Cary, NC). Sample size was calculated using power law analysis. Assumptions for the tests were checked using normal probability plots and residual plot analysis in JMP software. Two sampled student's unpaired t-test and Fisher's least significant difference (LSD) test were used to determine the level of significance at 5% unless mentioned otherwise.

Bladder cancer is the fourth most common cancer in men and tenth most common in women. In the U.S., nearly 74,000 new cases of bladder cancer were expected to be diagnosed in 2015. Approximately 70% of patients with early stage non-muscle invasive bladder cancer (NMIBC) suffer disease recurrence after initial surgical treatment. Hypoxia has been shown to significantly correlate with an unfavorable prognosis in bladder cancer. Similarly, the efficacy of radiation therapy and chemotherapy can be significantly hampered by hypoxia in bladder cancer. The contribution of hypoxia to chemoresistance, radioresistance, alteration of vasculature, chaotic blood flow, and genomic instability are well documented. Normoxic malignant cells are 2 to 3 times more sensitive to cell death from radiation and chemo therapy than hypoxic malignant cells.[18] It is well known that targeting hypoxia enhances the efficacy of chemotherapy and radiation therapy.

While image guided-methods based on MRI exist for guided drug delivery, these require expensive and extensive instrumentation. We hypothesize that an ultrasound (US) beam mediated approach to steer oxygen nanobubbles (ONB) to the tumor site will not only increase the localization of ONBs at the tumor, but will also aid in oxygenation and possible penetration of the bubbles into the tumor vasculature based on sonoporation. We also expect oxygenation will sensitize hypoxic cells to subsequent chemotherapy because normal cells are two to three times more receptive to subsequent therapies compared to hypoxic cells.

The adjuvant chemotherapy of choice for NMIBC is intravesical instillation of bacillus Calmette-Guérin (BCG) or mitomycin-C (MMC) While mitomycin-C delays disease progression of NMIBC in most patients, long-term follow-up reveals a high recurrence rate (approximately 30-70% in over 10 years). Retreatment with BCG or MMC can be efficacious, but often is limited by increased localized or systemic toxicity, leading to cessation of treatment. Furthermore, the development of resistance to BCG therapy is common. Treatment of advanced stage, muscle invasive cancers localized to the bladder with BCG is not effective, thus cystectomy is often performed, which dramatically impacts a patient's quality of life.

In this study, we report that nanosize cellulose-based oxygen bubbles can be used for drug encapsulation and precise drug delivery by propelling the nanobubbles using an ultrasound Doppler beam. Re-oxygenation of the hypoxic tissue was shown to destabilize hypoxia driven pathways and significantly suppress tumor progression. Here, we show that ONBs can be propelled along the ultrasound Doppler beam while being imaged in real time in vivo. For intravesical therapy, first, the nanobubbles (NBs) were injected via a catheter in the bladder of a mouse (FIG. 41A). Upon confirmation of ONB localization using B-mode ultrasound, pulsed wave Doppler ultrasound was employed to precisely steer the ONBs to the hypoxic regions of the tumor (FIG. 41B). Precise drug delivery by means of beam steering allows us to guide the nanobubbles directly onto hypoxic tumor region, thus, making the nanobubbles permeate the tumor tissue and efficiently deliver the desired drug. In this study, we show that the amount of chemotherapeutic drug can be decreased by 50% and significantly lower tumor progression rates can be achieved. Consequently, our novel approach provides an injectable, nanoscale delivery system that significantly enhances the efficacy of chemotherapeutic by effective precise drug delivery and targeted re-oxygenation of hypoxic tumor regions.

Synthesis and Optimization of ONB Efficacy In Vitro

Oxygen nanobubbles (ONBs) with a size of 200 nm were synthesized using crosslinking chemistry to encapsulate nanosized oxygen within a sodium carboxymethylcellulose shell. First, cell cytotoxicity assays were carried out with MB49 cell line to evaluate the effect of ONB (0.02-20 mg/mL) and MMC (0.05-50 µg/mL) (FIG. 41C). We found that both treatments had a significant effect on cell viability compared to control (no treatment). MMC had the most pronounced effect on cell viability with 0.5 µg/mL MMC concentration resulting in ~30% cell viability. ONB's were significant in reducing cell viability to ~50% at the highest synthesized concentration of 20 mg/mL. Oxygen concentrations in the culture media increased significantly upon addition of ONBs indicating that the therapeutic effect may be a result of perturbation in the hypoxia-adaptive pathways.

Next, we hypothesized that the oxygenation due to ONBs can synergistically increase the effectiveness of MMC. We prepared MMC-ONB drug combinations by crosslinking MMC within the ONB shell (See Methods) and observed the viability of MB49 cells. It was found that a dose consisting of 17 µg/ml MMC and 1 mg/mL ONB yielded complete cell death (FIG. 41C). The ONB dose of 1 mg/mL contributed to halving of the dose of MMC while still yielding complete cell death. Thus, we found that the simultaneous effect of MMC and ONB resulted in a significant increase in cell death and can help reduce the concentration, and thus, the toxicity and side effects of MMC.

In Vitro Beam Steering Optimization

The effect of beam steering on cell viability was studied using a factorial design of experiments and response surface methodology using MMC (0.05-5 µg/mL), ONB (0.2-20 mg/mL) and beam steering (ON/OFF) as variables (Table 2). Both, MMC and ONB were significant in decreasing cell viability and we found that beam steering had a significant effect in decreasing cell viability when MMC (0.5 µg/mL) and ONB (2 mg/mL) were at 'medium' concentration (FIG. 47). The ultrasound beam steering was only significant in increasing the efficiency of the ONB-MMC combination therapy. No significant effect of the beam was observed on the MB49 cells treated individually with ONB or MMC. We hypothesize that oxygen nanobubbles have an improved effect when they are uptaken by cells compared to only oxygenating the cellular microenvironment. Previously, we demonstrated the uptake of ONB without beam steering in prostate cancer cells using darkfield microscopy. Thus, from in vitro experiments, we concluded that the combination of ONB-MMC was found to be highly significant in reducing the cell viability of MB49 bladder cancer cells and the effect of beam steering was found to have a pronounced effect on the combinatorial treatment, compared to the individual ONB or MMC treatments. Further, we investigated the parameters influencing nanobubble velocity under the Doppler ultrasound beam by conducting a two level factorial design (Table 3) with four parameters: bubble size (400 nm and 800 nm), ultrasound power (20% and 100%), ultrasound frequency (32 MHz and 40 MHz) and beam angle (0° and 15°). We found that both, beam power and beam frequency were significant in increasing the velocity of the nanobubble ($P<0.01$). The beam angle did not appear to be significant in changing the velocity of the nanobubble.

In Vivo Characterization of Beam Steering

Beam steering experiments were performed in vivo in mice in the absence of tumors to investigate how the ultrasound beam power influences nanobubble velocity. The average velocity of ONB was observed to significantly increase as the power was increased from 5% to 100%, making it possible to propel nanobubbles at desired velocities by tuning the power of the ultrasound Doppler beam (FIG. 48). Using these results, we utilized 100% of the transducer's power for future experiments to achieve highest nanobubble velocities and more dynamic beam steering. We expect that the higher the velocity of the nanobubble, the higher the probability and distance of ONB penetration into the tumor.

Beam Steering of ONB in Bladder Cancer Mouse Model

Next, the parameters established in vitro and in vivo were utilized to scale up the evaluation of oxygen nanobubbles (ONB) in mouse models and to explore enhanced localization using beam steering. B-mode ultrasound clearly outlined the heterogeneous MB49 tumor implanted in the bladder wall (FIG. 42A). The treatment groups for our experiments were: (a) saline (CTRL); (b) mitomycin-C (MMC, 1 µg/mL), and (c) oxygen nanobubbles encapsulated with mitomycin-C (ONB-MMC, 0.5 µg/mL MMC and 2 mg/mL ONB). Based on our in vitro experiments, the concentration of MMC in ONB-MMC group was chosen to be 50% lower compared to the MMC group, since we hypothesized that beam steering can enhance the efficacy of the ONB-MMC group and results in significant tumor reduction, in vivo.

Upon intravesical injection, the ONBs can be visualized in the bladder lumen (yellow highlight, FIG. 42B). Briefly, enhanced localization of beam steering was demonstrated in vivo in syngeneic orthotopic solid bladder tumor (FIG. 42C). Tumors were established in C57BL/6J mice by intravesical instillation of MB49 cells. 2D (FIG. 42D) and 3D (FIG. 43A) volumetric quantification of the tumors and monitoring of tumor development was repeatedly and longitudinally evaluated in mice using the Vevo 2100 Ultrasound Imaging System (FujiFilm VisualSonics Inc., Toronto CA), equipped with segmentation tool for 3D images.[30] For intravesical therapy, the treatment groups (CTRL, MMC, ONB-MMC) were injected via a catheter in the mouse bladder every other day. Ultrasound Doppler Beam was then applied to each group every other day to induce beam steering and 0° beam angle was used to guide the nanobubbles. The nanobubbles were propelled along the beam and were precisely guided towards the tumor (FIG. 42C).

3D tumor reconstructions were performed for each representative mouse from ONB-MMC, MMC, and CTRL groups. A 3D ultrasound video of the tumor was broken down into individual 2D slices. The tumor contour was drawn for each 2D slice; all the 2D images were then lofted to create a 3D volume. 3D ultrasound image reconstruction from 2D images is not only an excellent visualization toolkit, but also offers accurate measurements of tumor volumes for comparison across ONB-MMC, MMC, and CTRL groups.

Further, we found that ONB-MMC group showed significantly slower tumor progression rate compared to the MMC-only group (FIG. 43B). Both, MMC and ONB-MMC groups were significant in reducing the tumor volume compared to CTRL. ONB-MMC also showed prolonged survival compared to MMC-only and CTRL groups (FIG. 43C). No adverse effects were observed in the mice treated with ONB-MMC whereas two acute toxicity events were recorded in mice treated with MMC only which necessitated the mice to be euthanized. This shows that the ONB treatment reduces the toxicity of MMC. Further, the average mouse body weights were significantly lower for MMC and CTRL group mice compared to ONB-MMC groups indicating the reduced toxicity obtained because of the lower dose of MMC and reduction in systemic toxicity by ONB (FIG. 43D). Oxygen measurements were performed to evaluate the extent of oxygenation obtained in the mouse bladder. Oxygen content in the mouse bladder was measured in control mice and in ONB-MMC mice before and after the injection of ONB-MMC. The results show that ONB-MMC oxygen content before the injection of ONB is significantly higher than that of the CTRL group, indicating that ONB can provide a steady oxygen release and continuous oxygenation of the hypoxic regions of the tumor (FIG. 43E). These results demonstrate the ability of ONB in enhancing the performance of MMC, allowing the use of significantly lower concentration of chemotherapeutic drug, and prolonging survival rates in MB49 bladder cancer mice.

We further characterized the reversal of chronic hypoxia due to oxygen nanobubbles in the ex vivo mouse bladder by quantifying and visualizing the expression of VEGF, HIF, and CD31 using established protocols. We found that control tumors stained positive (brown coloration highlighted with arrows show positive cytoplasmic staining) for both, VEGF (FIG. 44A) and HIF-1 (FIG. 44B), consistent with previous reports in literature, indicating that hypoxia is a critical stimulus for angiogenesis via up-regulation of the expression of VEGF and HIF. Angiogenesis and high density of blood vessels has been correlated with poor prognosis, metastasis, and bladder cancer invasion in clinical studies. Compared to control, the VEGF and HIF-1 levels were significantly lower in bladder tissues of mice treated with ONB-MMC and MMC. The effect was more pronounced in ONB-MMC treated mice compared to only MMC since oxygenation because of ONB is probably due to significant reversal of hypoxia in the tissue. The significantly lower expression of HIF and VEGF in ONB-MMC samples indicates that the lower tumor volumes observed could be because of the anti-angiogenesis and hypoxia targeting potential of ONB s. Overall, the different staining presented here indicate the different anti-angiogenesis mechanisms triggered because of the reversal of hypoxia obtained using ONB.

Validation of ONB Localization Using Hyperspectral Dark-Field Microscopy

To confirm the localization of the ONBs inside the tumors because of beam steering, dark-field images of cryosectioned tumor tissues were obtained and the ONBs at successive layers were quantified using ImageJ. First, the mouse bladder was stained with tissue marker dye to maintain orientation during dissection post-euthanasia (FIG. 45A). Further, the tissues were cryopreserved and sectioned using a cryotome. Successive sections were obtained every 100 μm from the bladder wall. Next, the tissue sections were imaged with a dark-field microscope using a previously published protocol.[28] The bladder orientation was maintained using the tissue ink applied during dissection that was observed at ×10 magnification (FIG. 45B). We found that ONBs were clearly visible up to 500 μm sections from the tumor periphery (FIG. 45C, top image). Thus, the nanobubbles can easily penetrate through the tumor tissue without much hindrance. The amount of nanobubbles decreased with distance from the tumor periphery indicating that the Doppler penetration had limitations on the distance of penetration obtained (FIG. 45D). The mechanical force of the ultrasound Doppler beam can be tuned by changing beam power, frequency, and time of insonation, to obtain desired depth of localization of the nanobubbles.

A theoretical model was developed to predict the velocity profile of nanobubbles through the media (urine inside the bladder) and to comprehensively approximate the pressure profile inside the bladder and, finally, outline the significant forces acting on the bubble (FIG. 46). The forces taken into account were Bjerkens force (results from out of phase bubble oscillations and ultrasound wave oscillations),[40] buoyancy force (the weight of the liquid displaced by the bubble), and drag force (force, acting opposite to the direction of the bubble movement in the liquid). Gravitational force was neglected due to nanobubble's insignificant mass in comparison to other contributing forces. It is known that ultrasound pressure wave can be represented as a harmonic plane wave. Bjerkens force is acting downward on the bubble, and is represented by the product of the volume of the bubble and the gradient of the pressure wave. The average Reynold's number was calculated to be $3.75 \times 10^{-3}$, indicating a laminar flow and linear dependence of Drag force on the bubble velocity. The objective was to derive the velocity profile of ONB as it is propelled by the transduced pressure wave in the lumen. The defining differential of Newton's law was coupled with the expression of the net force acting on the bubble and was further integrated with respect to time to yield the velocity profile presented in equation (2).

$$v(t) = A \cdot \cos(\omega t) - B \cdot \sin(\omega t) + C \cdot e^{\alpha t} \quad (2)$$

where A, B, C, and α are constants that depend on the mass, volume and radius of the bubble, urine viscosity and density and gravitational acceleration. ω is the angular frequency of the pressure wave.

FIG. 46 shows the velocity data and a theoretical model for the ONBs' ultrasound propelled motion. The obtained model shows the nanobubble velocity profile as it moves from the top to the bottom of the bladder (bladders with no tumor were used for data collection). As the bubble moves further away from the transducer and the intensity of the pressure wave deteriorates, the ONB velocity progressively decreases. It can also be noticed that the maximum velocity increases as the ultrasound power is increased from 30% (FIG. 46A) to 70% (FIG. 46B). It should be noted that the intravesical treatments and beam steering were performed at 100% power (FIG. 46C), where the nanobubble velocity is highest. Further, since the traveling distance to the tumor is much shorter than the distance travelled in an empty bladder, the velocity of bubble penetration in the tissue would be much higher that the terminal velocity of the nanobubbles in the empty bladder (FIG. 46A, point C).

Overall, we have demonstrated enhanced efficacy and reduced toxicity of MMC using ONB to revert hypoxia. We show that ONB-MMC were precisely guided and powered into the tumor using ultrasound image-based Doppler beam steering. We have optimized nanobubbles' velocity, magnitude of accumulation, and distance traversed in response to ultrasound frequency, power, and beam angle. Finally, the changes in the hypoxia-adaptive pathways and in the orthotopic mouse bladder tumors because of MMC and ONB were studied.

We have demonstrated that oxygen nanobubble carrier for mitomycin-C can be precisely guided to hypoxic bladder tumors and can enhance the effectiveness and reduce the toxicity of conventional chemotherapy. The ONBs were guided using an ultrasound Doppler beam to the tumor and the acoustic 'bombardment' of the nanoparticles enhances its uptake by the tumor cells. This new concept was illustrated using MB49 bladder tumors syngenically grown in mouse bladders. Efficient steering of the nanobubbles was demonstrated with a velocity of over 30 mm/s in the mouse bladder. The mitomycin-C dose was reduced by half for a similar efficacy in therapy. Further, ultrasound Doppler beam parameters such as angle, acoustic power, and frequency and their effects on the nanobubble velocity and acceleration were investigated using a theoretical model.

Those skilled in the art will recognize that numerous modifications can be made to the specific implementations described above. The implementations should not be limited to the particular limitations described. Other implementations may be possible.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

What is claimed is:

1. A synergistic treatment regimen for a non-muscle invasive bladder cancer (NMIBC) tumor, comprising administering synthesized oxygen nanobubbles (ONBs) to a site of bladder tumor, wherein said ONBs each comprises a gaseous molecular oxygen core surrounded by a cellulosic polymer shell, wherein said core-shell structure is capable to force a light to deviate from its linear trajectory to generate light scattering, wherein said synthesized ONBs are sized between about 400 nm to about 800 nm, the cellulosic polymer shell comprises a reaction product of a crosslinker and carboxymethyl cellulose (CMC) material, and the crosslinker has a concentration of 0.1% to 1.0%, and the carboxymethyl cellulose (CMC) material has a concentration of 0.1% to 1.0%, the ONBs further encapsulate at least one of a therapeutic drug and a florescence imaging agent, and the synthesized ONBs with drug encapsulation are guided by applying ultrasound beam and precisely steering the encapsulated drug to hypoxia regions of the NMIBC tumor.

2. The treatment regimen according to claim 1, wherein the therapeutic drug is Mitomycin-C (MMC), and the dose of therapeutic drug (MMC) encapsulated in ONBs is reduced to about half compared to MMC treatment alone to the bladder tumor.

3. The treatment regimen according to claim 1, wherein the ONBs travel to hypoxia regions of the bladder tumor with maximum velocity about 30 mm/s to about 40 mm/s.

4. The treatment regimen according to claim 1, wherein the synthesized ONBs reverts hypoxia condition in said NMIBC tumors.

5. The treatment regimen for NMIBC of claim 1, wherein said therapeutic drug is bacillus Calmette-Guerin (BCG), or mitomycin-C (MMC), and said therapeutic drug is encapsulated within said ONBs.

6. The treatment regimen for NMIBC of claim 1, wherein the carboxymethyl cellulose (CMC) material comprises sodium carboxymethylcellulose, and the crosslinker comprises aluminum chloride.

* * * * *